US009902765B2

(12) United States Patent
Doranz et al.

(10) Patent No.: US 9,902,765 B2
(45) Date of Patent: Feb. 27, 2018

(54) ANTIBODIES AGAINST CHIKUNGUNYA VIRUS AND USES THEREOF

(71) Applicants: Integral Molecular, Inc., Philadelphia, PA (US); Blood Systems Research Institute, San Francisco, CA (US)

(72) Inventors: Benjamin Doranz, Philadelphia, PA (US); Kimberly-Anne Mattia, Philadelphia, PA (US); Kristen Kahle, Philadelphia, PA (US); Graham Simmons, San Francisco, CA (US); Rachel Hua-Ning Fong, Philadelphia, PA (US); Soma Banik Banerjee, Philadelphia, PA (US)

(73) Assignees: INTEGRAL MOLECULAR, INC., Philadelphia, PA (US); BLOOD SYSTEMS RESEARCH INSTITUTE, San Francisco, CA (US)

( * ) Notice: Subject to any disclaimer, the term of this patent is extended or adjusted under 35 U.S.C. 154(b) by 0 days.

(21) Appl. No.: 14/441,867

(22) PCT Filed: Jul. 21, 2014

(86) PCT No.: PCT/US2014/047443
§ 371 (c)(1),
(2) Date: May 11, 2015

(87) PCT Pub. No.: WO2015/010125
PCT Pub. Date: Jan. 22, 2015

(65) Prior Publication Data

US 2016/0145323 A1 May 26, 2016

Related U.S. Application Data

(60) Provisional application No. 61/856,311, filed on Jul. 19, 2013.

(51) Int. Cl.
*C07K 16/10* (2006.01)

(52) U.S. Cl.
CPC ...... *C07K 16/1081* (2013.01); *C07K 2317/21* (2013.01); *C07K 2317/24* (2013.01); *C07K 2317/34* (2013.01); *C07K 2317/76* (2013.01); *C07K 2317/92* (2013.01); *C12N 2740/10023* (2013.01); *C12N 2770/36123* (2013.01); *C12N 2770/36134* (2013.01)

(58) Field of Classification Search
None
See application file for complete search history.

(56) References Cited

U.S. PATENT DOCUMENTS

2007/0196369 A1 8/2007 Hoogenboom et al.
2011/0104198 A1 5/2011 Weiner et al.
2011/0143333 A1 6/2011 Brehin et al.

FOREIGN PATENT DOCUMENTS

EP 2374816 A1 10/2011

OTHER PUBLICATIONS

Rudikoff et al., PNAS USA, 1982, 79:1979-1983.*
Colman, P.M., Research in Immunology, 1994, 145: 33-36.*
Kam et al., Early neutralizing IgG response to Chikungunya virus in infected patients targets a dominant linear epitope the E2 glycoprotein, EMBO Mol Med. 2012 4:330-343.
Lee et al., Chikungunya virus neutralization antigens and direct cell-to-cell transmission are revelaed by human antibody-escape mutants, PLoS Pathog. 2011 7(12):1-15 e1002390.
Pal et al., Development of a highly protective combination monoclonal antibody therapy against Chikungunya virus, PLoS Pathog. 2013 9(4):1-16 e1003312.
Sun et al., Structural analyses at pseudo atomic resultion of Chikungunya virus and antibodies show mechanisms of neutrilization, Elife 2013 2:1-27 e00435.
Voss et al., Gycoprotein organization of Chikungunya virus particles revealed by X-ray crystallography, Nature 2010 468:709-712 and supplementary information 1-65.
Written Opinion of the ISA for PCT/US2014/047443 dated Dec. 10, 2014.
ISR for PCT/US2014/047443 dated Dec. 10, 2014.
Brehin et al., Production and characterization of mouse monoclonal antibodies reactive to Chikungunya envelope E2 glycoprotein, Virology 2007 371(1):185-195.
Fric et al., Use of human monoclonal antibodies to treat Chikungunya virus infection, Journal of Infectious Diseases 2012 207(2):319-322.
Goh et al., Neutralizing monoclonal antibodies to the E2 protein of Chikungunya virus protects against disease in a mouse model, Clin. Immuno. 2013 149(3):487-497.

* cited by examiner

*Primary Examiner* — Stacy B Chen
(74) *Attorney, Agent, or Firm* — Pepper Hamilton LLP

(57) ABSTRACT

Embodiments disclosed herein provide for antibodies, including neutralizing antibodies, against Chikungunya virus, uses thereof, and methods of identifying antibodies, including neutralizing antibodies, against Chikungunya virus. In some embodiments, antibodies that binds to a CHIKV antigen, wherein the antigen is the CHIKV E1, E2, E3 protein, or any heterocomplex thereof are provided. In some embodiments, the antibody is an isolated antibody, a neutralizing antibody, a recombinant antibody, or any combination thereof. In some embodiments, the antibodies described herein bind to an epitope of E2 Domain A, E2 Domain B, or E1 Domain II of the CHIKV antigen. In some embodiments, the antigen is E2 protein.

3 Claims, 20 Drawing Sheets

| Location | Residue | CNP2B-H12 | IM-CKV061 | IM-CKV062 | CAP4A-E7 | CAP5A-F6 | IM-CKV066 | CAP1A-B3 | C9 | Surface Expression (rPAb) | Infectivity | % Sequence Identity |
|---|---|---|---|---|---|---|---|---|---|---|---|---|
| Neutralizing | | No | No | No | Yes | Yes | No | No | Yes | - | - | - |
| Epitope | | E1 FL | E1 FL, E2 Arch 2 | E1 FL, E2 Arch 2 | E2 DA | E2 DA&B, Arch1&2 | E1 FL&DII, E2 Arch 1 | E1 FL | E2 Arch 1 | - | - | - |
| Alphavirus reactivity | | Broad | Broad | Broad | CHIKV & SFV | CHIKV | CHIKV | Broad | CHIKV & SFV | - | - | - |
| Panning Reagent | | CHIKV VLPs | Retroviral VLPs | Retroviral VLPs | Retroviral VLPs | Retroviral VLPs | CHIKV VLPs (A226V) | CHIKV VLPs (A226V) | - | - | - | - |
| E2 Domain A (E2DA) | E24A | N.D. | N.D. | N.D. | 15 (13) | 53 (25) | 68 (35) | 57 (19) | N.D. | N.D. | 40 (6) | 14 |
| | G55A | 123 (13) | 79 (9) | 112 (9) | 12 (12) | 42 (9) | 53 (17) | 74 (14) | 90 (7) | 122 (11) | 26 (39) | 100 |
| | W64A | 95 (2) | 64 (23) | 61 (4) | 1 (4) | 33 (1) | 89 (49) | 43 (3) | 29 (24) | 93 (1) | 162 (224) | 21 |
| | K66T | 88 (16) | 81 (1) | 62 (10) | 15 (9) | 38 (2) | 59 (31) | 43 (37) | 72 (46) | 106 (28) | 43 (62) | 71 |
| | H73A | 151 (5) | 91 (8) | 184 (68) | 91 (66) | 0 (1) | 119 (41) | 43 (7) | 133 (29) | 70 (3) | 34 (54) | 64 |
| | I74A | 62 (1) | 86 (59) | 78 (28) | 123 (17) | 0 (0) | 82 (24) | 82 (48) | 89 (9) | 76 (9) | 123 (24) | 0 |
| | R80A | 70 (5) | 78 (71) | 65 (22) | 3 (2) | 58 (5) | 94 (43) | 82 (51) | 59 (21) | 75 (33) | 104 (103) | 57 |
| | H99A | 99 (52) | 75 (36) | 62 (42) | 81 (51) | 14 (8) | 156 (2) | 69 (23) | 73 (23) | 90 (39) | 6 (12) | 64 |
| | I121A | 93 (10) | 123 (3) | 66 (21) | 2 (3) | 96 (24) | 127 (42) | 109 (18) | 89 (24) | 107 (52) | 79 (107) | 14 |
| E2 Arch 1 | Q146A | 98 (31) | 60 (9) | 95 (39) | 53 (19) | 56 (2) | 19 (5) | 51 (31) | 68 (12) | 50 (1) | 51 (104) | 14 |
| | A162S | 110 (26) | 94 (24) | 74 (8) | 37 (3) | 187 (14) | 161 (2) | 106 (29) | 12 (16) | 117 (24) | 105 (97) | 14 |
| | M171A | 125 (64) | 158 (24) | 115 (17) | 151 (28) | 0 (2) | 175 (52) | 106 (24) | 128 (15) | 154 (47) | 32 (36) | 29 |
| E2 Domain B (E2DB) | Q195A | 29 (4) | N.D. | N.D. | 114 (34) | 1 (1) | 119 (4) | 126 (37) | N.D. | N.D. | N.D. | 14 |
| | T196A | 125 (31) | 106 (26) | 111 (22) | 156 (53) | 0 (1) | 122 (7) | 121 (47) | 99 (44) | 120 (4) | 40 (116) | 50 |
| | Y199A | 58 (3) | 59 (5) | 99 (21) | 50 (13) | 12 (2) | 61 (9) | 77 (21) | 65 (46) | 64 (5) | 68 (64) | 86 |
| | C201A | 23 (3) | N.D. | N.D. | 52 (14) | 3 (2) | 57 (36) | 37 (29) | N.D. | N.D. | N.D. | 93 |
| | G209A | 61 (53) | 69 (10) | 54 (6) | 36 (29) | 8 (9) | 56 (3) | 43 (74) | 49 (34) | 73 (25) | 47 (44) | 79 |
| | T212A | 57 (4) | 39 (3) | 47 (13) | 51 (13) | 3 (3) | 50 (7) | 72 (52) | 67 (9) | 86 (42) | 25 (33) | 50 |
| | N231A | 66 (7) | N.D. | N.D. | 47 (8) | 7 (0) | 78 (9) | 29 (4) | N.D. | N.D. | N.D. | 21 |
| E2 Arch 2 | K233A | 136 (42) | 135 (25) | 105 (14) | 123 (54) | 3 (4) | 123 (17) | 122 (12) | 108 (19) | 144 (24) | 56 (102) | 29 |
| | M267A | 129 (16) | 2 (1) | 8 (2) | 31 (8) | 46 (6) | 135 (33) | 39 (2) | 80 (43) | 104 (26) | 27 (24) | 14 |
| E1 Fusion Loop (E1FL) | G83A | 94 (10) | 81 (0) | 56 (35) | 67 (21) | 68 (20) | -1 (1) | 59 (12) | 71 (32) | 81 (26) | 8 (5) | 93 |
| | Y85A | 39 (5) | 46 (9) | 70 (2) | 119 (20) | 87 (8) | 2 (7) | 86 (55) | 115 (3) | 91 (2) | 1 (2) | 100 |
| | F87A | 87 (42) | 53 (34) | 67 (20) | 27 (13) | 104 (5) | -2 (4) | 140 (95) | 47 (0) | 99 (15) | 1 (2) | 93 |
| | W89A | 6 (10) | 16 (0) | 7 (4) | 163 (10) | 274 (26) | 189 (55) | 8 (1) | 119 (104) | 112 (23) | 1 (0) | 100 |
| | D97A | 104 (21) | N.D. | N.D. | 87 (32) | 91 (28) | 1 (3) | 63 (4) | N.D. | N.D. | N.D. | 93 |
| | N100A | 1 (2) | 10 (4) | 4 (2) | 53 (35) | 55 (16) | 29 (27) | 8 (7) | 92 (39) | 122 (16) | 1 (2) | 100 |
| E1 Domain II (E1DII) | T228A | 103 (11) | 137 (11) | 78 (24) | 100 (50) | 167 (119) | 15 (5) | 82 (22) | 83 (59) | 116 (6) | 99 (38) | 21 |

ANTIBODIES AGAINST CHIKUNGUNYA VIRUS AND USES THEREOF

CROSS-REFERENCE TO RELATED APPLICATIONS

This application is a 35 U.S.C. § 371 national phase application of PCT Application No. PCT/US2014/047443, filed Jul. 21, 2014, which claims priority to U.S. Provisional Application No. 61/856,311, filed Jul. 19, 2013, each of which is incorporated herein by reference in its entirety.

GOVERNMENT INTERESTS

This invention was made with U.S. Government support (NIH Contract No. HHSN272200900055C) and the U.S. Government may therefore have certain rights in the invention.

BACKGROUND

Chikungunya virus (CHIKV) is a mosquito borne alphavirus, first isolated in Tanzania in 1952 that has caused sporadic outbreaks of predominantly rheumatic disease every 2-50 years, primarily in Africa and Asia. The largest epidemic of CHIKV disease ever recorded took place during 2004-2011, and involved an estimated 1.4 to 6.5 million cases and the first autochthonous CHIKV infections in Europe (Italy in 2007 and France in 2010). Imported cases were also reported in nearly 40 countries, including European countries, Japan, and the USA. The epidemic was associated with the emergence of a new clade of viruses, which were efficiently transmitted by *Aedes albopictus*, a mosquito vector that has seen a dramatic global expansion in its geographic distribution. CHIKV disease is characterized by acute and chronic polyarthritis/polyarthralgia, which is usually symmetric and often incapacitating and occasionally protracted. Other symptoms, such as fever, rash, myalgia, and/or fatigue, are often also present during the acute phase. The recent epidemic was also associated with atypical and severe clinical forms of CHIKV disease and some fatalities, which appeared to be restricted to the very young and elderly patients with comorbidities.

CHIKV particles contain three major structural proteins: glycosylated E1 and E2 envelope (env) proteins embedded in the viral membrane, and a non-glycosylated nucleocapsid protein. Based on similarity to other alphaviruses, E2 mediates receptor attachment, while E1 is a class II viral fusion protein. A third glycoprotein, E3, is associated with mature virions in some alphaviruses, but not others, while 6K protein, a membrane-associated peptide created by cleavage of the polyprotein to release E2 and E1, is incorporated into particles at a low level.

The organization of the alphavirus surface glycoproteins in particles has been defined using cryo-electron microscopy (cryo-EM), while the atomic structure of CHIKV glycoproteins was recently solved by x-ray crystallography both for mature particles and for immature p62 Env precursor polyprotein prior to furin cleavage. 240 copies each of three glycoproteins (E3/E2/E1) come together to form a protein coat with icosahedral symmetry and containing 80 spikes. The folding, transport to the surface and function of these glycoproteins relies on their correct interactions with each other. E1 consists of three β-sheet domains, termed I, II and III, while E2 contains three immunoglobulin-like domains (A, B and C, with A being at the N-terminus). In the complex, domain B lies at the membrane distal end and contacts E3, domain C is closest to the viral membrane, and domain A is in the center. E1 interacts laterally with E2 all along domain II, along with additional points of contact from other regions of E1. E1 contains an internal fusion loop at the tip of domain II, which in the mature structure exists as a β-hairpin lodged in a groove between domains A and B of E2. E3 also plays a role in protecting the fusion loop from premature exposure.

Treatment of CHIKV rheumatic disease usually involves non-steroidal anti-inflammatory drugs (NSAIDs) and/or simple analgesics, which can provide relief, but is often inadequate. Although a number of vaccine strategies have been, or are being, explored, there are currently no licensed human vaccines for any alphavirus. Nevertheless, it is clear that CHIKV neutralizing antibodies from infected humans or vaccinated monkeys can mediate protection prophylactically, or soon after exposure. Polyclonal immunoglobulins derived from humans recovered from CHIKV infection, when passively transferred into neonatal and interferon α/β receptor deficient ($IFNAR^{-/-}$) mice protected these animals from CHIKV-induced viremia and mortality. Purified total IgG from monkeys immunized three times with a CHIKV virus-like-particle vaccine (containing E1 and E2) similarly protected $IFNAR^{-/-}$ mice from CHIKV viremia and mortality. A recent study described two monoclonal antibodies 5F10 and 8B10, which were isolated from CHIKV infected individuals. These antibodies specifically neutralized CHIKV and o'nyong'nyong virus (ONNV, a virus closely related to CHIKV), but none of the other alphaviruses tested. The 5F10 and 8B10 antibodies, when used in escape mutant studies were shown to recognize key residues in E2 (V216) and E1 (T101), respectively. The combination of 5F10 and 8B10 monoclonal antibodies were also shown to significantly delay CHIKV-driven lethality in mice deficient in IFNα/β and IFNγ receptors, and mature B and T cells.

Accordingly, there is a need for further treatments including, antibody treatments against CHIKV.

The present embodiments fulfill other needs as well and will be evident from the description contained herein.

SUMMARY OF THE INVENTION

In some embodiments, antibodies that binds to a CHIKV antigen, wherein the antigen is the CHIKV E1, E2, E3 protein, or any heterocomplex thereof are provided. In some embodiments, the antibody is an isolated antibody, a neutralizing antibody, a recombinant antibody, or any combination thereof.

In some embodiments, the antibody is a human or humanized antibody.

In some embodiments, the antibodies described herein bind to an epitope of E2 Domain A, E2 Domain B, or E1 Domain II of the CHIKV antigen. In some embodiments, the antigen is E2 protein.

In some embodiments, the antibody comprises a sequence at least 90% identical to a sequence selected from the group consisting of SEQ ID NOs: 1-26 or an antigen binding fragment thereof. In some embodiments, the antibody comprises a $V_L$ sequence at least 90% identical to a sequence of SEQ ID NOs: 2, 4, 6, 8, 10, 12, 14, 16, 18, 20, 22, 24, or 26 or an antigen binding fragment thereof. In some embodiments, the antibody comprises a $V_H$ sequence at least 90% identical to a sequence of SEQ ID NOs: 1, 3, 5, 7, 9, 11, 13 15, 17, 19, or 21, 23, or 25, or an antigen binding fragment thereof. In some embodiments, the antibody comprises a sequence at least 90% identical to a sequence SEQ ID NOs: 1 and 2, SEQ ID NOs: 3 and 4, SEQ ID NOs: 5 and 6, SEQ ID NOs: 7 and 8, SEQ ID NOs: 9 and 10, SEQ ID NOs: 11 and 12, SEQ ID NOs: 13 and 14, SEQ ID NOs: 15 and 16, SEQ ID NOs: 17 and 18, SEQ ID NOs: 19 and 20, SEQ ID NOs: 21 and 22, SEQ ID NOs: 23 and 24, or SEQ ID NOs: 25 and 26.

In some embodiments, pharmaceutical compositions comprising one or more antibodies described herein are provided. In some embodiments, the composition is free of antibodies that do not bind to a CHIKV antigen.

In some embodiments, methods of treating, inhibiting or ameliorating a CHIKV infection comprising administering an antibody described herein or a pharmaceutical composition described herein are provided. In some embodiments, the method reduces a pathology associated with CHIKV infection.

In some embodiments, methods of detecting the presence or absence of a CHIKV antigen in a sample are provided. In some embodiments, the methods comprise contacting a sample with an antibody, such as those described herein, and detecting the binding to a CHIKV antigen by the antibody, wherein the detection of the binding indicates the presence of CHIKV antigen; or the absence of the detection of the binding to the CHIKV antigen indicates the absence of the CHIKV antigen.

In some embodiments, methods of identifying an antibody that binds to an epitope, wherein the epitope comprises residues: E2-G95; E2-A162; E2-159-171; E2-A164, E2-E165, E2-E166 and/or E2-I167; E2-Y69, E2-F84, E2-V113, E2-G114, E2-T116, and/or E2-D117; at least one of Subunit I-E2-E24 and Subunit I-E2-I121 and at least one of: Subunit II-E2-G55, Subunit II-E2-W64, Subunit II-E2-K66, Subunit II-E2-R80; any combination thereof are provided. In some embodiments, the methods comprises contacting a test antibody with the epitope and determining whether the test antibody binds to the epitope.

In some embodiments, methods of inducing an immune response against a CHIKV antigen fragment are provided. In some embodiments, the methods comprises administering a CHIKV antigen fragment to a subject under conditions sufficient to induce an immune response. In some embodiments, the antigen comprises residues: E2-G95; E2-A162; E2-159-171; E2-A164, E2-E165, E2-E166 and/or E2-I167; E2-Y69, E2-F84, E2-V113, E2-G114, E2-T116, and/or E2-D117; at least one of Subunit I-E2-E24 and Subunit I-E2-I121 and at least one of: Subunit II-E2-G55, Subunit II-E2-W64, Subunit II-E2-K66, Subunit II-E2-R80; or any combination thereof.

In some embodiments, compositions including isolated compositions are provided. In some embodiments, the composition comprises an antibody bound to a CHIKV protein, wherein the antibody is bound to an epitope comprises residues: E2-G95; E2-A162; E2-159-171; E2-A164, E2-E165, E2-E166 and/or E2-I167; E2-Y69, E2-F84, E2-V113, E2-G114, E2-T116, and/or E2-D117; at least one of Subunit I-E2-E24 and Subunit I-E2-I121 and at least one of: Subunit II-E2-G55, Subunit II-E2-W64, Subunit II-E2-K66, Subunit II-E2-R80; or any combination thereof. In some embodiments, the antibody is a neutralizing antibody.

BRIEF DESCRIPTION OF DRAWINGS

FIG. 6. Protection against arthritis and viremia in a CHIKV mouse model. C57BL/6 mice (n=4 mice per group) were injected with (i) PBS; (ii) purified C9 mAb or (iii) purified control human mAb at 0.5 mg/mouse by the intraperitoneal route one day (day −1) prior to infection on day 0 with CHIKV (isolate LR2006-OPY1). (A) Peripheral blood viremia ($CCID_{50}$/ml). X-axis represents days post-CHIKV inoculation; (B) Foot swelling over time presented as a group average of the percentage increase in foot height×width (in the metatarsal region) for each foot compared with the same foot on day 0 (n=8 feet).

FIG. 9. CHIKV MAb reactivity with alphavirus envelopes, VLP surfaces, and cell surface E2/E1. (A) MAbs isolated against CHIKV E2/E1 were tested by flow cytometry for immunoreactivity with envelope proteins of alphaviruses CHIKV, SFV, RRV, and SINV expressed on HEK-293T cells. Cells were either fixed with 4% paraformaldehyde to test immunoreactivity with select MAbs (CNP2B-H12, IM-CKV061, IM-CKV062, CAP1A-B3, and V5) or left unfixed (for MAbs CAP4A-E7, CAP5A-F6, CAP1A-B5, and C9). As a control, cells were permeabilized for immunodetection of the V5 epitope tag engineered onto the C-terminus of each envelope. Cells transfected with pUC19 empty vector were used as a negative control ('No Env'). The data shown represent the mean and standard deviation of four data points, and data is representative of at least two independent experiments. (B) MAb reactivities against E2/E1 were tested on retroviral VLPs, CHIKV VLPs, and CHIKV E2/E1 expressed on HEK-293T cells. VLP reactivity was detected using ELISA, while cell surface reactivity was detected by flow cytometry. Samples were either fixed with 4% paraformaldehyde or left unfixed, as in panel A. Bars represent the mean and standard deviation of three data points for VLP reactivity and four data points for cell surface reactivity. All data is representative of at least two independent experiments. MAbs showed negligible reactivity with controls that included DENV VLPs (Control VLPs') and mock transfected HEK-293T cells ('Control Cells').

FIG. 20. Residues critical for CHIKV MAb binding. Summary data for CHIKV E2/E1 MAbs is shown with detailed information for epitope residues including reactivity, surface expression, pseudovirus infectivity, and sequence conservation. Activities are expressed as percent wild-type with ranges (maximum-minimum values) in parentheses. Values are shaded in grey for critical residues. For CAP4A-E7, immunoreactivity for the Fab is shown. At least two replicate values were obtained for each experiment. Either CHIKV VLPs (S27 strain with or without an A226V mutation) or retroviral VLPs ('Lipoparticles', made with murine leukemia virus Gag) were used for phage panning to isolate MAbs. Surface expression was determined by immunoreactivity with a rabbit polyclonal antibody (rPAb, a gift from IBT Bioservices). Percent sequence identity at individual residues was determined by comparing the sequences of 14 different alphaviruses (Voss J E, Vaney M C, Duquerroy S, Vonrhein C, Girard-Blanc C, et al. (2010) Glycoprotein organization of Chikungunya virus particles revealed by X-ray crystallography. Nature 468: 709-712). N.D. indicates not done.

DETAILED DESCRIPTION

Figure 1:
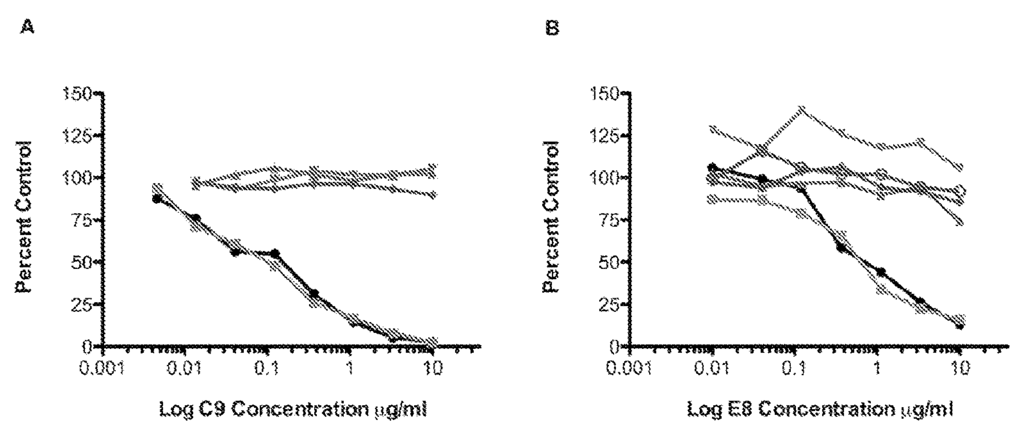
FIG. 1. Human mAbs C9 and E8 neutralize CHIKV pseudovirions. Neutralization of pseudovirus bearing CHIKV S27 wild-type (black); CHIKV A226V mutant (light blue); SFV (red); SINV (magenta); RRV (green) and VSV (dark blue) envelope by (A) C9 or (B) E8 mAbs. Antibody concentration is shown on the x-axis. The results are expressed as the percentage of no antibody control and represent mean of triplicate wells, and is representative of three experiments.

The term "antibody" as used herein is meant in a broad sense and includes immunoglobulin or antibody molecules including polyclonal antibodies, monoclonal antibodies including murine, human, humanized and chimeric monoclonal antibodies and antibody fragments. In some embodiments, the antibody is a neutralizing antibody. A neutralizing antibody is an antibody that can inhibit the infection of a virus, such as Chikungunya virus. Examples of neutralizing antibodies are provided herein.

The term "humanized antibody", "engineered antibody", "human framework adapted", and "HFA" as used herein, is intended to include antibodies having variable region frameworks derived from sequences of human origin. Furthermore, if the antibody contains a constant region, the constant region can be derived from such human sequences, e.g., human germline sequences, or naturally occurring (e.g., allotypes) or mutated versions of human germline sequences. The humanized antibodies may include amino acid residues not encoded by human sequences (e.g., mutations introduced by random or site-specific mutagenesis in vitro or by somatic mutation in vivo). It is routine to convert a non-human antibody to a humanized antibody based upon a given sequence. Accordingly, any non-human antibody disclosed herein also describes a humanized antibody because it can be converted to the humanized antibody using well known methods and protocols.

In general, antibodies are proteins or polypeptides that exhibit binding specificity to a specific antigen. Intact antibodies are heterotetrameric glycoproteins, composed of two identical light chains and two identical heavy chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain and the light chain variable domain is aligned with the variable domain of the heavy chain. Antibody light chains of any vertebrate species can be assigned to one of two clearly distinct types, namely kappa and lambda, based on the amino acid sequences of their constant domains. Immunoglobulins can be assigned to five major classes, namely IgA, IgD, IgE, IgG and IgM, depending on the heavy chain constant domain amino acid sequence. IgA and IgG are further sub-classified as the isotypes $IgA_1$, $IgA_2$, $IgG_1$, $IgG_2$, $IgG_3$ and $IgG_4$.

The term "antibody fragment" means a portion of an intact antibody, generally the antigen binding or variable region of the intact antibody. Examples of antibody fragments include Fab, Fab', $F(ab')_2$ and Fv fragments, diabodies, single chain antibody molecules and multispecific antibodies formed from at least two intact antibodies.

The term "antigen" as used herein means any molecule that has the ability to generate antibodies either directly or indirectly. Included within the definition of "antigen" is a protein-encoding nucleic acid.

As used herein, "specific binding" or "immunospecific binding" or "binds immunospecifically" refer to antibody binding to a predetermined antigen or epitope present on the antigen. In some embodiments, the antibody binds with a dissociation constant ($K_D$) of $10^{-7}$ M or less, and binds to the predetermined antigen with a $K_D$ that is at least two-fold less than its $K_D$ for binding to a non-specific antigen (e.g., BSA, casein, or another non-specific polypeptide) other than the predetermined antigen. The phrases "an antibody specific for CHIKV protein" is used interchangeably herein with the term "an antibody which binds immunospecifically to CHIKV protein."

"CDRs" are defined as the complementarity determining region amino acid sequences of an antibody which are the hypervariable regions of immunoglobulin heavy and light chains. See, e.g., Kabat et al., Sequences of Proteins of Immunological Interest, 4th ed., U.S. Department of Health and Human Services, National Institutes of Health (1987). There are three heavy chain and three light chain CDRs or CDR regions in the variable portion of an immunoglobulin. Thus, "CDRs" as used herein refers to all three heavy chain CDRs, or all three light chain CDRs or both all heavy and all light chain CDRs, if appropriate.

CDRs provide the majority of contact residues for the binding of the antibody to the antigen or epitope. CDRs of interest in this invention are derived from donor antibody variable heavy and light chain sequences, and include analogs of the naturally occurring CDRs, which analogs also share or retain the same antigen binding specificity and/or neutralizing ability as the donor antibody from which they were derived.

The term "homolog" means protein sequences having between 40% and 100% sequence identity to a reference sequence. Percent identity between two peptide chains can be determined by pair wise alignment using the default settings of the AlignX module of Vector NTI v.9.0.0 (Invitrogen Corp., Carlsbad, Calif.). In some embodiments, the an antibody or fragment thereof has at least 50, 60, 70, 80, 90, 91, 92, 93, 94, 95, 96, 97, 98, or 99% identity to a sequence described herein. In some embodiments, the sequence is a $V_L$ sequence or a $V_H$ sequence. The sequence can also be considered similar if it has a conservative substitution. In some embodiments, the antibody has conservative substitutions as compared to a sequence described herein. Examples of conservative substitutions include the following:

TABLE

| Exemplary Conservative Substitutions: | |
|---|---|
| Original Residue | Exemplary Conservative Substitutions |
| Ala | Val, Leu, Ile, Ser |
| Arg | Lys, Gln, Asn |
| Asn | Gln |
| Asp | Glu |
| Cys | Ser, Ala |
| Gln | Asn |
| Gly | Pro, Ala |
| His | Asn, Gln, Lys, Arg |
| Ile | Leu, Val, Met, Ala, Phe |
| Leu | Ile, Val, Met, Ala, Phe |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

In some embodiments, the conservative substitution can be made according to the following criteria:

| | |
|---|---|
| Basic: | arginine |
| | lysine |
| | histidine |
| Acidic: | glutamic acid |
| | aspartic acid |
| Uncharged Polar: | glutamine |
| | asparagine |
| | serine |
| | threonine |
| | tyrosine |
| Non-Polar: | phenylalanine |
| | tryptophan |
| | cysteine |
| | glycine |
| | alanine |
| | valine |
| | praline |
| | methionine |
| | leucine |
| | isoleucine |

Other variants can consist of less conservative amino acid substitutions, such as selecting residues that differ more significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. The substitutions that in general are expected to have a more significant effect on function are those in which (a) glycine and/or proline is substituted by another amino acid or is deleted or inserted; (b) a hydrophilic residue, e.g., seryl or threonyl, is substituted for (or by) a hydrophobic residue, e.g., leucyl, isoleucyl, phenylalanyl, valyl, or alanyl; (c) a cysteine residue is substituted for (or by) any other residue; (d) a residue having an electropositive side chain, e.g., lysyl, arginyl, or histidyl, is substituted for (or by) a residue having an electronegative charge, e.g., glutamyl or aspartyl; or (e) a residue having a bulky side chain, e.g., phenylalanine, is substituted for (or by) one not having such a side chain, e.g., glycine. Other variants include those designed to either generate a novel glycosylation and/or phosphorylation site(s), or those designed to delete an existing glycosylation and/or phosphorylation site(s). Variants include at least one amino acid substitution at a glycosylation site, a proteolytic cleavage site and/or a cysteine residue. Variants also include proteins and peptides with additional amino acid residues before or after the protein or peptide amino acid sequence on linker peptides. The term "variant" also encompasses polypeptides that have the amino acid sequence of the proteins/peptides of the present invention with at least one and up to 25 (e.g., 1, 2, 3, 4, 5, 6, 7, 8, 9, 10, 15, 20) additional amino acids flanking either the 3' or 5' end of the amino acid sequence or both.

The term "in combination with" as used herein means that the described agents can be administered to an animal together in a mixture, concurrently as single agents or sequentially as single agents in any order.

Polyclonal antibodies are heterogeneous populations of antibody molecules derived from the sera of animals immunized with an antigen. A monoclonal antibody contains a substantially homogeneous population of antibodies specific to antigens, which population contains substantially similar epitope binding sites. MAbs may be obtained by methods known to those skilled in the art. See, for example Kohler and Milstein, Nature 256:495 497 (1975); U.S. Pat. No. 4,376,110; Ausubel et al., eds., Current Protocols in Molecular Biology, Greene Publishing Assoc. and Wiley Interscience, N.Y., (1987, 1992); and Harlow and Lane ANTIBODIES: A Laboratory Manual Cold Spring Harbor Laboratory (1988); Colligan et al., eds., Current Protocols in Immunology, Greene Publishing Assoc. and Wiley Interscience, N.Y., (1992, 1993), the contents of which references are incorporated entirely herein by reference. Such antibodies may be of any immunoglobulin class including IgG, IgM, IgE, IgA, GILD and any subclass thereof. A hybridoma producing a mAb of the present invention may be cultivated in vitro, in situ or in vivo. Production of high titers of mAbs in vivo or in situ makes this the presently preferred method of production.

Chimeric antibodies are molecules, different portions of which are derived from different animal species, such as those having variable region derived from a murine mAb and a human immunoglobulin constant region, which are primarily used to reduce immunogenicity in application and to increase yields in production, for example, where murine mAbs have higher yields from hybridomas but higher immunogenicity in humans, such that human/murine chimeric mAbs are used. Chimeric antibodies and methods for their production are known in the art (Cabilly et al., Proc. Natl. Acad. Sci. USA 81:3273 3277 (1984); Morrison et al., Proc. Natl. Acad. Sci. USA 81:6851 6855 (1984); Boulianne et al., Nature 312:643 646 (1984); Cabilly et al., European Patent Application 125023 (published Nov. 14, 1984); Neuberger et al., Nature 314:268 270 (1985); Taniguchi et al., European Patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Morrison et al., European Patent Application 173494 (published Mar. 5, 1986); Sahagan et al., J. Immunol. 137:1066 1074 (1986); Robinson et al., International Patent Publication #PCT/US86/02269 (published May 7, 1987); Liu et al., Proc. Natl. Acad. Sci. USA 84:3439 3443 (1987); Sun et al., Proc. Natl. Acad. Sci. USA 84:214 218 (1987); Better et al., Science 240:1041 1043 (1988); and Harlow and Lane Antibodies. a Laboratory Manual Cold Spring Harbor Laboratory (1988)). These references are entirely incorporated herein by reference.

An anti-idiotypic (anti-Id) antibody is an antibody which recognizes unique determinants generally associated with the antigen-binding site of an antibody. An Id antibody can be prepared by immunizing an animal of the same species and genetic type (e.g., mouse strain) as the source of the mAb with the mAb to which an anti-Id is being prepared. The immunized animal will recognize and respond to the idiotypic determinants of the immunizing antibody by producing an antibody to these idiotypic determinants (the anti-Id antibody). See, for example, U.S. Pat. No. 4,699,880, which is herein entirely incorporated by reference. The anti-Id antibody may also be used as an "immunogen" to induce an immune response in yet another animal, producing a so-called anti-anti-Id antibody. The anti-anti-Id may be epitopically identical to the original mAb which induced the anti-Id. Thus, by using antibodies to the idiotypic determinants of a mAb, it is possible to identify other clones expressing antibodies of identical specificity.

The term "monoclonal antibody" (mAb) as used herein means an antibody (or antibody fragment) obtained from a population of substantially homogeneous antibodies. Monoclonal antibodies are highly specific, typically being directed against a single antigenic determinant. The modifier "monoclonal" indicates the substantially homogeneous character of the antibody and does not require production of the antibody by any particular method. For example, murine mAbs can be made by the hybridoma method of Kohler et al., Nature 256:495-497 (1975). Chimeric mAbs containing a light chain and heavy chain variable region derived from a donor antibody (typically murine) in association with light and heavy chain constant regions derived from an acceptor antibody (typically another mammalian species such as human) can be prepared by the method disclosed in U.S. Pat. No. 4,816,567. Humanized mAbs having CDRs derived from a non-human donor immunoglobulin (typically murine) and the remaining immunoglobulin-derived parts of the molecule being derived from one or more human immunoglobulins, optionally having altered framework support residues to preserve binding affinity, can be obtained by the techniques disclosed in Queen et al., Proc. Natl. Acad. Sci. (USA), 86:10029-10032 (1989) and Hodgson et al., Bio/Technology, 9:421 (1991).

In addition to the antibodies described herein, exemplary human framework sequences useful for humanization are disclosed at, e.g., www.ncbi.nlm.nih.gov/entrez/query.fcgi; www.ncbi.nih.gov/igblast; www.atcc.org/phage/hdb.html; www.mrc-cpe.cam.ac.uk/ALIGNMENTS.php; www.kabatdatabase.com/top.html; ftp.ncbi.nih.gov/repository/kabat; www.sciquest.com; www.abcam.com; www.antibodyresource.com/onlinecomp.html; www.public.iastate.edu/.about.pedro/research_tools.html; www.whfreeman.com/immunology/CH05/kuby05.htm; www.hhmi.org/grants/lectures/1996/vlab; www.path.cam.ac.uk/.about.mrc7/mikeimages.html; mcb.harvard.edu/BioLinks/Immunology.html; www.immunologylink.com; pathbox.wustl.edu/.about.hcenter/index.html; www.appliedbiosystems.com; www.nal.usda.gov/awic/pubs/antibody; www.m.chime-u.acjp/.about.yasuhito/Elisa.html; www.biodesign.com; www.cancerresearchuk.org; www.biotech.ufl.edu; www.isac-net.org; baserv.uci.kun.nl/.about.jraats/links1.html; www.recab.unihd.de/immuno.bme.nwu.edu; www.mrc-cpe.cam.ac.uk; www.ibt.unam.mx/vir/V_mice.html; http://www.bioinf.org.uk/abs; antibody.bath.ac.uk; www.unizh.ch; www.cryst.bbk.ac.uk/.about.ubcg07s; www.nimr.mrc.ac.uk/CC/ccaewg/ccaewg.html; www.path.cam.ac.uk/.about.mrc7/humanisation/TAHHP.html; www.ibt.unam.mx/vir/structure/stat_aim.html; www.biosci.missouri.edu/smithgp/index.html; www.jerini.de; imgt.cines.fr; and Kabat et al., Sequences of Proteins of Immunological Interest, U.S. Dept. Health (1987), each entirely incorporated herein by reference.

Anti-CHIKV antigen antibodies can include, but are not limited to, at least one of a heavy chain constant region ($H_c$), a heavy chain variable region ($H_v$), a light chain variable region ($L_v$) and a light chain constant region ($L_c$), wherein a polyclonal Ab, monoclonal Ab, fragment and/or regions thereof include at least one heavy chain variable region ($H_v$) or light chain variable region ($L_v$) which binds a portion of a CHIKV antigen (e.g., ENV, E1, E2, E3, 6K protein) and can be used to detect the antigen. The sequences for the CHIKV proteins are known and can be also be found herein. SEQ ID NOs: 27 (ENV), 29 (E1), 31 (E2), 33 (E3), and 35 (6K) provide amino acid sequences for the proteins and SEQ ID NOs: 28 (ENV), 30 (E1), 21 (E2), 34 (E3), and 36 (6K) provide nucleotide sequences encoding the same.

Methods for determining mAb specificity and affinity by competitive inhibition can be found in Harlow, et al., Antibodies: A Laboratory Manual, Cold Spring Harbor Laboratory Press, Cold Spring Harbor, N.Y., 1988), Colligan et al., eds., Current Protocols in Immunology, Greene Publishing Assoc. and Wiley Interscience, N.Y., (1992, 1993), and Muller, Meth. Enzymol. 92:589 601 (1983), which references are entirely incorporated herein by reference.

The techniques to raise antibodies to small peptide sequences that recognize and bind to those sequences in the free or conjugated form or when presented as a native sequence in the context of a large protein are well known in the art. Such antibodies include murine, murine-human and human-human antibodies produced by hybridoma or recombinant techniques known in the art. Antibodies can also be produced in goats, rabbits, chickens, llamas, or other small animals.

As used herein, the term "antigen binding region" refers to that portion of an antibody molecule which contains the amino acid residues that interact with an antigen (e.g. CHIKV proteins) and confer on the antibody its specificity and affinity for the antigen. The antibody region includes the "framework" amino acid residues necessary to maintain the proper conformation of the antigen-binding residues. In some embodiments, the antigen binding region will be of murine origin. In some embodiments, the antigen binding region can be derived from other animal species, in particular rodents such as rabbit, rat or hamster. It has been shown that the antigen-binding function of an antibody can be performed by fragments of a full-length antibody. Examples of binding fragments encompassed within the term "antigen-binding portion" of an antibody include a Fab fragment, a monovalent fragment having the VL, VH, CL and CH1 domains; a $F(ab)_2$ fragment, a bivalent fragment comprising two Fab fragments linked by a disulfide bridge(s) at a hinge region; a Fd fragment having the VH and CH1 domains; a Fv fragment having the VL and VH domains of a single arm of an antibody; a domain antibody or dAb fragment (Ward et al., 1989 Nature 341:544-546), which consists of a VH domain; and an isolated complementarity determining region (CDR), especially a CDR3 (See for example the WO03/025019, the contents of which are incorporated herein by reference).

The term "Complementarity Determining Regions (CDRs)" is based on sequence variability (Wu and Kabat, J. Exp. Med. 132:211-250, 1970). There are six CDRs—three in the variable heavy chain, or VH, and are typically designated H-CDR1, H-CDR2, and H-CDR3, and three CDRs in the variable light chain, or VL, and are typically designated L-CDR1, L-CDR2, and L-CDR3 (Kabat et al., Sequences of Proteins of Immunological Interest, 5th Ed. Public Health Service, National Institutes of Health, Bethesda, Md., 1991). "Hypervariable region", "HVR", or "HV" refer to the regions of an antibody variable domain which are variable in structure as defined by Chothia and Lesk (Chothia and Lesk, Mol. Biol. 196:901-917, 1987). There are six HVRs, three in VH (H1, H2, H3) and three in VL (L1, L2, L3). Chothia and Lesk refer to structurally conserved HVs as "canonical structures." Another method of describing the regions that form the antigen-binding site has been proposed by Lefranc (Lefranc et al., Developmental & Comparative Immunology 27:55-77, 2003) based on the comparison of V domains from immunoglobulins and T-cell receptors (Lefranc et al., Developmental & Comparative Immunology 27:55-77, 2003). The antigen-binding site can also be delineated based on "Specificity Determining Residue Usage (SDRU)", according to Almagro (Almagro, Mol. Recognit. 17:132-43, 2004), where SDRU refers to amino acid residues of an immunoglobulin that are directly involved in antigen contact.

Furthermore, although the two domains of the Fv fragment, VL and VH, are encoded by separate genes naturally, they can be joined, using recombinant methods, by a synthetic linker that enables them to be made as a single protein chain in which the VL and VH regions pair to form monovalent molecules (known as single chain Fv (scFv); see e.g., Bird et al., 1988 Science 242:423-426; and Huston et al., 1988 Proc. Nat. Acad. Sci. 85:5879-5883). Such single chain antibodies are encompassed by the term "antigen-binding portion" of an antibody. These antibody fragments are obtained using conventional techniques known to those of skill in the art, and can be used in the same manner as intact antibodies.

An "isolated antibody," as used herein, refers to an antibody that is substantially free of other antibodies having different antigenic specificities (e.g., an isolated antibody that specifically binds CHIKV proteins and is substantially free of antibodies that specifically bind antigens other than CHIKV proteins). Moreover, an isolated antibody may be substantially free of other cellular material and/or chemicals. An isolated antibody can also be sterile or pyrogen free or formulated as injectable pharmaceutical as described herein. In some embodiments, the antibody cross-reacts with other viruses of the same family, such as other alphaviruses, including, but not limited to the alphaviruses described herein.

In some embodiments, the source for the DNA encoding a non-human antibody includes cell lines which produce the antibody, such as hybrid cell lines commonly known as hybridomas.

An "antigen" is a molecule or a portion of a molecule capable of being bound by an antibody which is additionally capable of inducing an animal to produce antibody capable of binding to an epitope of that antigen. An antigen can have one or more than one epitope. The specific reaction referred to above is meant to indicate that the antigen will react, in a highly selective manner, with its corresponding antibody and not with the multitude of other antibodies which can be evoked by other antigens. In some embodiments, antigens that bind antibodies, fragments and regions of anti-CHIKV antigen antibodies include at least 5 amino acids. In some embodiments, the antigen is present on the surface of a CHIKV virus particle. In some embodiments, the antigen is presented on a virus-like particle that has a CHIKV Envelope pseudotyped onto the particle. The particle can be, for example, a MLV-based virus-like particle. In some embodiments, the antibody can be isolated by isolating the antibody from a naturally infected patient. In some embodiments, B-cells from an infected patient are isolated and grown. The MAbs produced by these B-cells are isolated to identify reactive MAbs. In some embodiments, the RNA from the B-cells is extracted (e.g. isolated) from the B-cells and used to create cDNAs. The cDNAs can then be inserted into a display library (e.g. phage display) and used to screen CHIKV virus particles and/or CHIKV Envelope pseudotyped onto MLV-based virus-like particles to isolate and identify reactive MAbs.

Figure 3:
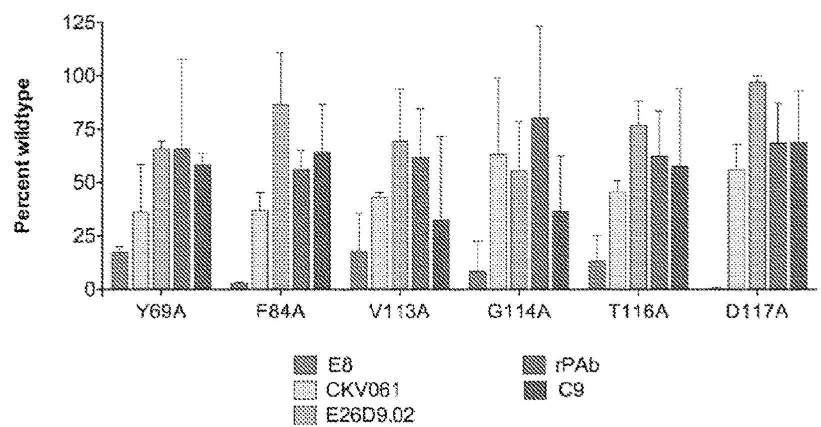
FIG. 3: Critical Residues and Predicted E8 Binding Site. (A) HEK-293 cells expressing mutant CHIKV envelope proteins were immunostained with E8 antibody. Clones with reactivity<20% relative to wild-type CHIKV env were identified as critical for E8 binding. Mutation of six individual E2 residues to alanine (Y69, F84, V113, G114, T116, and D117) significantly reduced E8 binding (red bars) but did not affect binding of C9 (green bar) or other control antibodies (gray bars). Residues are numbered according to E2 in the PDB entry #3N41 (Voss J E, Vaney M C, Duquerroy S, Vonrhein C, Girard-Blanc C, et al. (2010) Glycoprotein organization of Chikungunya virus particles revealed by X-ray crystallography. Nature 468: 709-712). (B) Critical binding residues for E8 (shown in green) were visualized on the CHIKV env crystal structure. The E1, E2, and E3 envelope protein subunits in the monomer (PDB Entry #3N41) are depicted in FIG. 4, as yellow, red, and blue, respectively and the fusion loop is shown in silver (left panel). In the side-view and top-down trimeric representations (center, and right panels, PDB entry #2XFC), E3 is not in the structure. In the side view trimeric representation (center panel), the viral membrane is positioned at the bottom of the figure.
Figure 3:
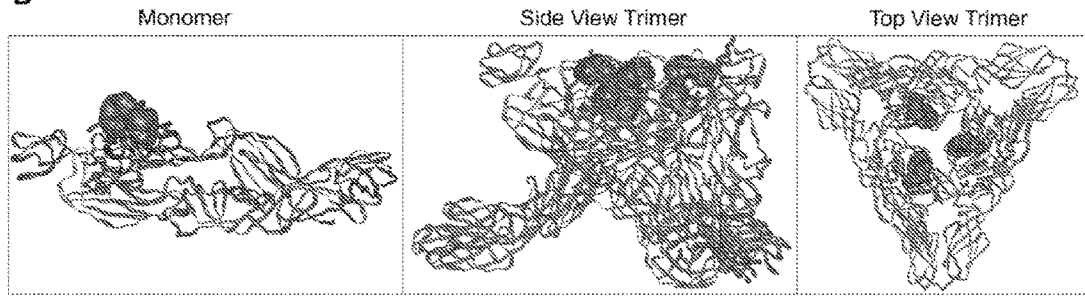

The term "epitope" is meant to refer to that portion of any molecule capable of being recognized by and bound by an antibody at one or more of the Ab's antigen binding regions. Epitopes usually consist of chemically active surface groupings of molecules such as amino acids or sugar side chains and have specific three dimensional structural characteristics as well as specific charge characteristics. Example of epitopes include, but are not limited to, those shown in FIGS. 3 and 4.

As used herein, the term "chimeric antibody" includes monovalent, divalent or polyvalent immunoglobulins. A monovalent chimeric antibody is a dimer (HL) formed by a chimeric H chain associated through disulfide bridges with a chimeric L chain. A divalent chimeric antibody is tetramer ($H_2L_2$) formed by two HL dimers associated through at least one disulfide bridge. A polyvalent chimeric antibody can also be produced, for example, by employing a $C_H$ region that aggregates (e.g., from an IgM H chain, or μ. chain). In some embodiments, murine and chimeric antibodies, fragments and regions of the present invention comprise individual heavy (H) and/or light (L) immunoglobulin chains.

Antibodies, fragments or derivatives having chimeric H chains and L chains of the same or different variable region binding specificity, can also be prepared by appropriate association of the individual polypeptide chains, according to known method steps, e.g., according to Ausubel infra, Harlow infra, and Colligan infra, the contents of which references are incorporated entirely herein by reference. With this approach, hosts expressing chimeric H chains (or their derivatives) are separately cultured from hosts expressing chimeric L chains (or their derivatives), and the immunoglobulin chains are separately recovered and then associated. Alternatively, the hosts can be co-cultured and the chains allowed to associate spontaneously in the culture medium, followed by recovery of the assembled immunoglobulin, fragment or derivative.

The hybrid cells are formed by the fusion of a non-human antibody-producing cell, typically a spleen cell of an animal immunized against either natural or recombinant antigen, or a peptide fragment of the antigen protein sequence. Alternatively, the non-human antibody-producing cell can be a B lymphocyte obtained from the blood, spleen, lymph nodes or other tissue of an animal immunized with the antigen.

The second fusion partner, which provides the immortalizing function, can be a lymphoblastoid cell or a plasmacytoma or myeloma cell, which is not itself an antibody producing cell, but is malignant. Fusion partner cells include, but are not limited to, the hybridoma SP2/0-Ag14, abbreviated as SP2/0 (ATCC CRL1581) and the myeloma P3×63Ag8 (ATCC TIB9), or its derivatives. See, e.g, Ausubel infra, Harlow infra, and Colligan infra, the contents of which references are incorporated entirely herein by reference.

Murine hybridomas which produce mAb specific for the antigen can be formed by the fusion of a mouse fusion partner cell, such as SP2/0, and spleen cells from mice immunized against purified antigen, recombinant antigen, natural or synthetic antigen derived peptides, including peptides including 5 or more amino acids selected from residues from the antigen or other biological preparations containing the antigen. To immunize the mice, a variety of different conventional protocols can be followed. For example, mice can receive primary and boosting immunizations of the antigen.

The antibody-producing cell contributing the nucleotide sequences encoding the antigen-binding region of the chimeric antibody of the present invention can also be produced by transformation of a non-human, such as a primate, or a human cell. For example, a B lymphocyte which produces the antibody can be infected and transformed with a virus such as Epstein-Barr virus to yield an immortal antibody producing cell (Kozbor et al., Immunol. Today 4:72 79 (1983)). Alternatively, the B lymphocyte can be transformed by providing a transforming gene or transforming gene product, as is well-known in the art. See, e.g, Ausubel infra, Harlow infra, and Colligan infra, the contents of which references are incorporated entirely herein by reference.

The cell fusions are accomplished by standard procedures well known to those skilled in the field of immunology. Fusion partner cell lines and methods for fusing and selecting hybridomas and screening for mAbs are well known in the art. See, e.g, Ausubel infra, Harlow infra, and Colligan infra, the contents of which references are incorporated entirely herein by reference.

The antigen-specific murine or chimeric mAb can be produced in large quantities by injecting hybridoma or transfectoma cells secreting the antibody into the peritoneal cavity of mice and, after appropriate time, harvesting the ascites fluid which contains a high titer of the mAb, and isolating the mAb therefrom. For such in vivo production of the mAb with a non-murine hybridoma (e.g., rat or human), hybridoma cells are preferably grown in irradiated or athymic nude mice. Alternatively, the antibodies can be produced by culturing hybridoma or transfectoma cells in vitro and isolating secreted mAb from the cell culture medium or recombinantly, in eukaryotic or prokaryotic cells.

In some embodiments, the antibody is a MAb which binds amino acids of an epitope of the CHIKV antigen. In some embodiments, the CHIKV antigen is the E1 protein, E2 protein, 6k protein, or E3 protein. The CHIKV antigen can also be referred to as the CHIKV protein. Non-limiting examples of CHIKV antigens are provided herein. For example, SEQ ID NOs: 27-36 provide amino acid sequences of CHIKV antigens and nucleotide sequences encoding the same.

In some embodiments, the antibody comprises a sequence at least 91%, 92%, 93%, 94%, 95%, 96%, 97%, 98%, or 99% identical to a sequence selected from the group consisting of SEQ ID NOs:1-26 or an antigen binding fragment thereof. In some embodiments, the antibody comprises a sequence selected from the group consisting of SEQ ID NOs:1-26 or an antigen binding fragment thereof. In some embodiments, the antibody comprises a sequence at least 91%, 92%, 93%, 94%, 95%, 96%, 97%, 98%, or 99% identical to SEQ ID NOs: 1 and 2, SEQ ID NOs: 3 and 4, SEQ ID NOs: 5 and 6, SEQ ID NOs: 7 and 8, SEQ ID NOs: 9 and 10, SEQ ID NOs: 11 and 12, SEQ ID NOs: 13 and 14, SEQ ID NOs: 15 and 16, SEQ ID NOs: 17 and 18, SEQ ID NOs: 19 and 20, SEQ ID NOs: 21 and 22, SEQ ID NOs: 23 and 24, or SEQ ID NOs: 25 and 26. In some embodiments, the antibody comprises SEQ ID NOs: 1 and 2, SEQ ID NOs: 3 and 4, SEQ ID NOs: 5 and 6, SEQ ID NOs: 7 and 8, SEQ ID NOs: 9 and 10, SEQ ID NOs: 11 and 12, SEQ ID NOs: 13 and 14, SEQ ID NOs: 15 and 16, SEQ ID NOs: 17 and 18, SEQ ID NOs: 19 and 20, SEQ ID NOs: 21 and 22, SEQ ID NOs: 23 and 24, or SEQ ID NOs: 25 and 26. In some embodiments, the variable light chain or variable heavy chain comprises or consists of a sequence described herein alone or in combination, such as the combinations described herein.

In some embodiments, the antibody is an antibody that binds to an epitope on the E2 protein of CHIKV. In some embodiments, the antibody binds to E2-A162, or an epitope formed by residues E2-G95, E2-A162, E2-A164, E2-E165, E2-E166 and/or E2-I167, or any combination thereof. In some embodiments, the antibody binds to an epitope formed by residues E2-Y69, E2-F84, E2-V113, E2-G114, E2-T116, and/or E2-D117, or any combination thereof. In some embodiments, the epitope comprises E2-G95.

In some embodiments, the antibody is an antibody that binds to at least one of: Subunit I-E2-E24 and Subunit I-E2-I121 and at least one of: Subunit II-E2-G55, Subunit II-E2-W64, Subunit II-E2-K66, Subunit II-E2-R80. In some embodiments, the antibody binds to Subunit I-E2-E24 and Subunit I-E2-I121 and at least one of: Subunit II-E2-G55, Subunit II-E2-W64, Subunit II-E2-K66, Subunit II-E2-R80. In some embodiments, the antibody binds to at least two of Subunit II-E2-G55, Subunit II-E2-W64, Subunit II-E2-K66, Subunit II-E2-R80. In some embodiments, the antibody binds to at least three of Subunit II-E2-G55, Subunit II-E2-W64, Subunit II-E2-K66, Subunit II-E2-R80. In some embodiments, the antibody binds to at least three of Subunit II-E2-G55, Subunit II-E2-W64, Subunit II-E2-K66, and Subunit II-E2-R80. In some embodiments, the antibody binds to Subunit II-E2-G55, Subunit II-E2-W64, Subunit II-E2-K66, and Subunit II-E2-R80.

In some embodiments, the antibody binds to the membrane distal region of a CHIKV E1/E2 trimer. In some embodiments, the antibody binds to the exterior face of the E1/E2 heterocomplex. The exterior face refers to the portion of the E1/E2 heterocomplex that is exposed when the E1/E2 hetero-protein is in its native form on the virion surface, such as in its trimeric form.

In some embodiments, the antibodies provided herein bind to the CHIKV antigen with a $K_D$apparent of about 0.1 to about 2 nM. In some embodiments, antibody binds to the CHIKV antigen with a $K_D$apparent of about 0.1 to about 1.5 nM, about 0.1 to about 1.0 nM, about 0.1 to about 0.5 nM, about 0.1 to about 0.4 nM, about 0.2 to about 2 nM, about 0.2 to about 1.5 nM, about 0.2 to about 1.0 nM, about 0.2 to about 0.5 nM, about 0.2 to about 0.4 nM, about 0.3 to about 2 nM, about 0.3 to about 1.5 nM, about 0.3 to about 1.0 nM, or about 0.3 to about 0.5 nM, about 0.3 to about 0.4 nM. As described herein, in some embodiments, the antibody is a neutralizing antibody.

As used herein, the term "neutralizing" refers to neutralization of biological activity of a target protein, bacteria, or virus when a binding protein (e.g. antibody) binds the target protein. Neutralizing may be the result of different ways of binding of said binding protein to the target.

In some embodiments, the antibodies provided herein bind to the CHIKV antigen with a $K_D$ of about 300 picomolar to 10 nanomolar. In some embodiments, the antibodies provided herein bind to the CHIKV antigen with a $K_D$ of about 10 picomolar to 10 nanomolar. In some embodiments, the antibodies provided herein bind to the CHIKV antigen with a $K_D$ of about 20 picomolar to 10 nanomolar. In some embodiments, the antibodies provided herein bind to the CHIKV antigen with a $K_D$ of about 30 picomolar to 10 nanomolar. In some embodiments, the antibodies provided herein bind to the CHIKV antigen with a $K_D$ of about 40 picomolar to 10 nanomolar. In some embodiments, the antibodies provided herein bind to the CHIKV antigen with a $K_D$ of about 50 picomolar to 10 nanomolar. In some embodiments, the antibodies provided herein bind to the CHIKV antigen with a $K_D$ of about 60 picomolar to 10 nanomolar. In some embodiments, the antibodies provided herein bind to the CHIKV antigen with a $K_D$ of about 70 picomolar to 10 nanomolar. In some embodiments, the antibodies provided herein bind to the CHIKV antigen with a $K_D$ of about 80 picomolar to 10 nanomolar. In some embodiments, the antibodies provided herein bind to the CHIKV antigen with a $K_D$ of about 90 picomolar to 10 nanomolar. In some embodiments, the antibodies provided herein bind to the CHIKV antigen with a $K_D$ of about 100 picomolar to 10 nanomolar. In some embodiments, the antibodies provided herein bind to the CHIKV antigen with a $K_D$ of about 150 picomolar to 10 nanomolar. In some embodiments, the antibodies provided herein bind to the CHIKV antigen with a $K_D$ of about 200 picomolar to 10 nanomolar. In some embodiments, the antibodies provided herein bind to the CHIKV antigen with a $K_D$ of about 250 picomolar to 10 nanomolar. In some embodiments, the antibodies provided herein bind to the CHIKV antigen with a $K_D$ of about 5, 10, 15, 20, 25, 30, 40, 50, 60, 70, 80, 90, 100, 110, 120, 130, 140, 150, 160, 170, 180, 190, 200, 225, 250, 275 or 300 picomolar. In some embodiments, the antibodies provided herein bind to the CHIKV antigen with a $K_D$ of about 1, 2, 3, 4, 5, 6, 7, 8, 9, or 10 nanomolar.

In some embodiments, the antibody binds the CHIKV antigen with a $k_{on}$, of about $6\times10^4$ to about $3\times10^5$ $M^{-1}sec^{-1}$. In some embodiments, the antibody binds the CHIKV antigen with a $k_{on}$ of about $6\times10^4$ to about $5\times10^6$ $M^{-1}sec^{-1}$. In some embodiments, the antibody binds the CHIKV antigen with a $k_{on}$ of about $6\times10^4$ to about $1\times10^6$ $M^{-1}sec^{-1}$. In some embodiments, the antibody binds the CHIKV antigen with a $k_{on}$ of about $6\times10^4$ to about $2\times10^6$ $M^{-1}sec^{-1}$. In some embodiments, the antibody binds the CHIKV antigen with a $k_{on}$ of about $6\times10^4$ to about $3\times10^6$ $M^{-1}sec^{-1}$. In some embodiments, the antibody binds the CHIKV antigen with a $k_{on}$ of about $6\times10^4$ to about $4\times10^6$ $M^{-1}sec^{-1}$. In some embodiments, the antibody binds the CHIKV antigen with a $k_{on}$ of about $6\times10^4$ $M^{-1}sec^{-1}$, $1\times10^5$ $M^{-1}sec^{-1}$, $2\times10^5$ $M^{-1}sec^{-1}$, $3\times10^5$ $M^{-1}sec^{-1}$, $4\times10^5$ $M^{-1}sec^{-1}$, $5\times10^5$ $M^{-1}sec^{-1}$, $6\times10^5$ $M^{-1}sec^{-1}$, $7\times10^5$ $M^{-1}sec^{-1}$, $8\times10^5$ $M^{-1}sec^{-1}$, $9\times10^5$ $M^{-1}sec^{-1}$, $1\times10^6$ $M^{-1}sec^{-1}$, $2\times10^6$ $M^{-1}sec^{-1}$, $3\times10^6$ $M^{-1}sec^{-1}$, $4\times10^6$ $M^{-1}sec^{-1}$, $5\times10^6$ $M^{-1}sec^{-1}$ or $6\times10^6$ $M^{-1}sec^{-1}$,.

In some embodiments, the antibody binds to the CHIKV antigen with a $k_{off}$ of about $7\times10^{-5}$ to about $1\times10^{-3}$ $sec^{-1}$. In some embodiments, the antibody binds to the CHIKV antigen with a $k_{off}$ of about $1\times10^{-6}$ to about $1\times10^{-3}$ $sec^{-1}$.

As described herein the production of antibodies with a known sequence is routine and can be done by any method. Accordingly, in some embodiments, a nucleic acid encoding an antibody or fragment thereof is provided. In some embodiments, the nucleic acid encodes a sequence selected from the group consisting of SEQ ID NOs: 1-26.

The antibodies described herein can also be modified to be chimeric antibodies. The antibodies can also be used in injectable pharmaceutical compositions. As also described herein, the antibodies can be isolated antibodies or engineered antibodies. The antibodies can also be modified to be conjugated to a toxin or other chemical that can inhibit the replication or other aspect of the life cycle of the virus.

In some embodiments, the present invention provides for "derivatives" of the antibodies, fragments, regions or derivatives thereof, which term includes those proteins encoded by truncated or modified genes to yield molecular species functionally resembling the immunoglobulin fragments. The modifications include, but are not limited to, addition of genetic sequences coding for cytotoxic proteins such as plant and bacterial toxins. The modification can also include a reporter protein, such as a fluorescent or chemiluminescent tag. The fragments and derivatives can be produced in any manner.

Fragments include, for example, Fab, Fab', $F(ab')_2$ and Fv. These fragments lack the Fc fragment of intact antibody, clear more rapidly from the circulation, and can have less non-specific tissue binding than an intact antibody (Wahl et al., J. Nucl. Med. 24:316 325 (1983)). These fragments are produced from intact antibodies using methods well known in the art, for example by proteolytic cleavage with enzymes such as papain (to produce Fab fragments) or pepsin (to produce F(ab').sub.2 fragments).

The identification of these antigen binding regions and/or epitopes recognized by mAbs of the present invention provides the information necessary to generate additional monoclonal antibodies with similar binding characteristics and therapeutic or diagnostic utility that parallel the embodiments of this application.

The nucleic acid sequence encoding an antibody described herein can be genomic DNA or cDNA, or RNA (e.g. mRNA) which encodes at least one of the variable regions described herein. A convenient alternative to the use of chromosomal gene fragments as the source of DNA encoding the V region antigen-binding segment is the use of cDNA for the construction of chimeric immunoglobulin genes, e.g., as reported by Liu et al. (Proc. Natl. Acad. Sci., USA 84:3439 (1987) and J. Immunology 139:3521 (1987), which references are hereby entirely incorporated herein by reference. The use of cDNA requires that gene expression elements appropriate for the host cell be combined with the gene in order to achieve synthesis of the desired protein. The use of cDNA sequences is advantageous over genomic sequences (which contain introns), in that cDNA sequences can be expressed in bacteria or other hosts which lack appropriate RNA splicing systems.

For example, a cDNA encoding a V region antigen-binding segment able to detect, bind, to or neutralize a CHIKV antigen can be provided using known methods based on the use of the amino acid sequences provided herein. Because the genetic code is degenerate, more than one codon can be used to encode a particular amino acid (Watson, et al., infra). Using the genetic code, one or more different oligonucleotides can be identified, each of which would be capable of encoding the amino acid. The probability that a particular oligonucleotide will, in fact, constitute the actual encoding sequence can be estimated by considering abnormal base pairing relationships and the frequency with which a particular codon is used to encode a particular amino acid in eukaryotic or prokaryotic cells expressing an antibody or fragment. Such "codon usage rules" are disclosed by Lathe, et al., J. Molec. Biol. 183:1 12 (1985). Using the "codon usage rules" of Lathe, a single oligonucleotide, or a set of oligonucleotides, that contains a theoretical "most probable" nucleotide sequence capable of encoding an antibody variable or constant region sequences is identified.

The variable regions described herein can be combined with any type of constant region including a human constant region or murine constant region. Human genes which encode the constant (C) regions of the antibodies, fragments and regions of the present invention can be derived from a human fetal liver library, by known methods. Human C region genes can be derived from any human cell including those which express and produce human immunoglobulins. The human $C_H$ region can be derived from any of the known classes or isotypes of human H chains, including gamma, μ, α, δ or ϵ, and subtypes thereof, such as G1, G2, G3 and G4. Since the H chain isotype is responsible for the various effector functions of an antibody, the choice of $C_H$ region will be guided by the desired effector functions, such as complement fixation, or activity in antibody-dependent cellular cytotoxicity (ADCC). Preferably, the $C_H$ region is derived from gamma 1 (IgG1), gamma 3 (IgG3), gamma 4 (IgG4), or μ (IgM). The human $C_L$ region can be derived from either human L chain isotype, kappa or lambda.

Genes encoding human immunoglobulin C regions can be obtained from human cells by standard cloning techniques (Sambrook, et al. (Molecular Cloning: A Laboratory Manual, 2nd Edition, Cold Spring Harbor Press, Cold Spring Harbor, N.Y. (1989) and Ausubel et al., eds. Current Protocols in Molecular Biology (1987 1993)). Human C region genes are readily available from known clones containing genes representing the two classes of L chains, the five classes of H chains and subclasses thereof. Chimeric antibody fragments, such as $F(ab')_2$ and Fab, can be prepared by designing a chimeric H chain gene which is appropriately truncated. For example, a chimeric gene encoding an H chain portion of an $F(ab')_2$ fragment would include DNA sequences encoding the $CH_1$ domain and hinge region of the H chain, followed by a translational stop codon to yield the truncated molecule.

Generally, the murine, human or murine and chimeric antibodies, fragments and regions of the antibodies described herein are produced by cloning DNA segments encoding the H and L chain antigen-binding regions of a CHIKV antigen specific antibody, and joining these DNA segments to DNA segments encoding $C_H$ and $C_L$ regions, respectively, to produce murine, human or chimeric immunoglobulin-encoding genes.

Thus, in some embodiments, a fused chimeric gene is created which comprises a first DNA segment that encodes at least the antigen-binding region of non-human origin, such as a functionally rearranged V region with joining (J) segment, linked to a second DNA segment encoding at least a part of a human C region.

Therefore, cDNA encoding the antibody V and C regions, the method of producing the chimeric antibody according to some of the embodiments described herein involve several steps, as exemplified below: 1. isolation of messenger RNA (mRNA) from the cell line producing an anti-CHIKV antigen antibody and from optional additional antibodies supplying heavy and light constant regions; cloning and cDNA production therefrom; 2. preparation of a full length cDNA library from purified mRNA from which the appropriate V and/or C region gene segments of the L and H chain genes can be: (i) identified with appropriate probes, (ii) sequenced, and (iii) made compatible with a C or V gene segment from another antibody for a chimeric antibody; 3. Construction of complete H or L chain coding sequences by linkage of the cloned specific V region gene segments to cloned C region gene, as described above; 4. Expression and production of L and H chains in selected hosts, including prokaryotic and eukaryotic cells to provide murine-murine, human-murine, human-human or human murine antibodies.

One common feature of all immunoglobulin H and L chain genes and their encoded mRNAs is the J region. H and L chain J regions have different sequences, but a high degree of sequence homology exists (greater than 80%) among each group, especially near the C region. This homology is exploited in this method and consensus sequences of H and L chain J regions can be used to design oligonucleotides for use as primers for introducing useful restriction sites into the J region for subsequent linkage of V region segments to human C region segments.

C region cDNA vectors prepared from human cells can be modified by site-directed mutagenesis to place a restriction site at the analogous position in the human sequence. For example, one can clone the complete human kappa chain C ($C_k$) region and the complete human gamma-1 C region (Cγ-1). In this case, the alternative method based upon genomic C region clones as the source for C region vectors would not allow these genes to be expressed in bacterial systems where enzymes needed to remove intervening sequences are absent. Cloned V region segments are excised and ligated to L or H chain C region vectors. Alternatively, the human Cγ-1 region can be modified by introducing a termination codon thereby generating a gene sequence which encodes the H chain portion of an Fab molecule. The coding sequences with linked V and C regions are then transferred into appropriate expression vehicles for expression in appropriate hosts, prokaryotic or eukaryotic.

Two coding DNA sequences are said to be "operably linked" if the linkage results in a continuously translatable sequence without alteration or interruption of the triplet reading frame. A DNA coding sequence is operably linked to a gene expression element if the linkage results in the proper function of that gene expression element to result in expression of the coding sequence.

Expression vehicles include plasmids or other vectors. Preferred among these are vehicles carrying a functionally complete human $C_{.H}$ or $C_L$ chain sequence having appropriate restriction sites engineered so that any $V_H$ or $V_L$ chain sequence with appropriate cohesive ends can be easily inserted therein. Human $C_H$ or $C_L$ chain sequence-containing vehicles thus serve as intermediates for the expression of any desired complete H or L chain in any appropriate host.

A chimeric antibody, such as a mouse-human or human-human, will typically be synthesized from genes driven by the chromosomal gene promoters native to the mouse H and L chain V regions used in the constructs; splicing usually occurs between the splice donor site in the mouse J region and the splice acceptor site preceding the human C region and also at the splice regions that occur within the human C region; polyadenylation and transcription termination occur at native chromosomal sites downstream of the human coding regions.

As used herein and unless otherwise indicated, the term "about" is intended to mean±5% of the value it modifies. Thus, about 100 means 95 to 105.

In some embodiments, the antibodies described herein are used to detect the presence of the antigen. The present antibody can be used in any device or method to detect the presence of the antigen.

The term "purified" with referenced to an antibody refers to an antibody that is substantially free of other material that associates with the molecule in its natural environment. For instance, a purified protein is substantially free of the cellular material or other proteins from the cell or tissue from which it is derived. The term refers to preparations where the isolated protein is sufficiently pure to be analyzed, or at least 70% to 80% (w/w) pure, at least 80%-90% (w/w)

pure, 90-95% pure; and, at least 95%, 96%, 97%, 98%, 99%, or 100% (w/w) pure. In some embodiments, the antibody is purified.

The terms "specific binding," "specifically binds," and the like, mean that two or more molecules form a complex that is measurable under physiologic or assay conditions and is selective. An antibody or antigen binding protein or other molecule is said to "specifically bind" to a protein, antigen, or epitope if, under appropriately selected conditions, such binding is not substantially inhibited, while at the same time non-specific binding is inhibited. Specific binding is characterized by a high affinity and is selective for the compound, protein, epitope, or antigen. Nonspecific binding usually has a low affinity. Binding in IgG antibodies for example is generally characterized by an affinity of at least about $10^{-7}$ M or higher, such as at least about $10^{-8}$ M or higher, or at least about $10^{-9}$ M or higher, or at least about $10^{-10}$ or higher, or at least about $10^{-11}$ M or higher, or at least about $10^{-12}$ M or higher. The term is also applicable where, e.g., an antigen-binding domain is specific for a particular epitope that is not carried by numerous antigens, in which case the antibody or antigen binding protein carrying the antigen-binding domain will generally not bind other antigens. In some embodiments, the capture reagent has a $K_D$ equal or less than $10^{-9}$M, $10^{-10}$ M, or $10^{-11}$ M for its binding partner (e.g. antigen). In some embodiments, the capture reagent has a Ka greater than or equal to $10^9M^{-1}$ for its binding partner.

Intact antibodies, also known as immunoglobulins, are typically tetrameric glycosylated proteins composed of two light (L) chains of approximately 25 kDa each, and two heavy (H) chains of approximately 50 kDa each. Two types of light chain, termed lambda and kappa, exist in antibodies. Depending on the amino acid sequence of the constant domain of heavy chains, immunoglobulins are assigned to five major classes: A, D, E, G, and M, and several of these may be further divided into subclasses (isotypes), e.g., IgG1, IgG2, IgG3, IgG4, IgA1, and IgA2. Each light chain is composed of an N-terminal variable (V) domain (VL) and a constant (C) domain (CL). Each heavy chain is composed of an N-terminal V domain (VH), three or four C domains (CHs), and a hinge region. The CH domain most proximal to VH is designated CH1. The VH and VL domains consist of four regions of relatively conserved sequences named framework regions (FR1, FR2, FR3, and FR4), which form a scaffold for three regions of hypervariable sequences (complementarity determining regions, CDRs). The CDRs contain most of the residues responsible for specific interactions of the antibody or antigen binding protein with the antigen. CDRs are referred to as CDR1, CDR2, and CDR3. Accordingly, CDR constituents on the heavy chain are referred to as H1, H2, and H3, while CDR constituents on the light chain are referred to as L1, L2, and L3. CDR3 is the greatest source of molecular diversity within the antibody or antigen binding protein-binding site. H3, for example, can be as short as two amino acid residues or greater than 26 amino acids. The subunit structures and three-dimensional configurations of different classes of immunoglobulins are well known in the art. For a review of the antibody structure, see Antibodies: A Laboratory Manual, Cold Spring Harbor Laboratory, Eds. Harlow et al., 1988. One of skill in the art will recognize that each subunit structure, e.g., a CH, VH, CL, VL, CDR, and/or FR structure, comprises active fragments. For example, active fragments may consist of the portion of the VH, VL, or CDR subunit that binds the antigen, i.e., the antigen-binding fragment, or the portion of the CH subunit that binds to and/or activates an Fc receptor and/or complement.

In addition to the fragments described herein, non-limiting examples of binding fragments encompassed within the term "antigen-specific antibody" used herein include: (i) an Fab fragment, a monovalent fragment consisting of the VL, VH, CL and CH1 domains; (ii) an F(ab')2 fragment, a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated CDR. Furthermore, although the two domains of the Fv fragment, VL and VH, are coded for by separate genes, they may be recombinantly joined by a synthetic linker, creating a single protein chain in which the VL and VH domains pair to form monovalent molecules (known as single chain Fv (scFv)). The most commonly used linker is a 15-residue $(Gly4Ser)_3$ peptide, but other linkers are also known in the art. Single chain antibodies are also intended to be encompassed within the terms "antibody or antigen binding protein," or "antigen-binding fragment" of an antibody. The antibody can also be a polyclonal antibody, monoclonal antibody, chimeric antibody, antigen-binding fragment, Fc fragment, single chain antibodies, or any derivatives thereof.

These antibodies can be obtained using conventional techniques known to those skilled in the art and described herein, and the fragments are used in the same manner as intact antibodies. Antibody diversity is created by multiple germline genes encoding variable domains and a variety of somatic events. The somatic events include recombination of variable gene segments with diversity (D) and joining (J) gene segments to make a complete VH domain, and the recombination of variable and joining gene segments to make a complete VL domain. The recombination process itself is imprecise, resulting in the loss or addition of amino acids at the V(D)J junctions. These mechanisms of diversity occur in the developing B cell prior to antigen exposure. After antigenic stimulation, the expressed antibody genes in B cells undergo somatic mutation. Based on the estimated number of germline gene segments, the random recombination of these segments, and random VH-VL pairing, up to $1.6\times10^7$ different antibodies may be produced (Fundamental Immunology, 3rd ed. (1993), ed. Paul, Raven Press, New York, N.Y.). When other processes that contribute to antibody diversity (such as somatic mutation) are taken into account, it is thought that upwards of $1\times10^{10}$ different antibodies may be generated (Immunoglobulin Genes, 2nd ed. (1995), eds. Jonio et al., Academic Press, San Diego, Calif.). Because of the many processes involved in generating antibody diversity, it is unlikely that independently derived monoclonal antibodies with the same antigen specificity will have identical amino acid sequences.

Antibody or antigen binding protein molecules capable of specifically interacting with the antigens, epitopes, or other molecules described herein may be produced by methods well known to those skilled in the art. For example, monoclonal antibodies can be produced by generation of hybridomas in accordance with known methods. Hybridomas formed in this manner can then be screened using standard methods, such as enzyme-linked immunosorbent assay (ELISA) and Biacore analysis, to identify one or more hybridomas that produce an antibody that specifically interacts with a molecule or compound of interest.

As an alternative to preparing monoclonal antibody-secreting hybridomas, a monoclonal antibody to a polypeptide of the present invention may be identified and isolated by screening a recombinant combinatorial immunoglobulin library (e.g., an antibody phage display library) with a polypeptide of the present invention to thereby isolate immunoglobulin library members that bind to the polypeptide. Techniques and commercially available kits for generating and screening phage display libraries are well known to those skilled in the art. Additionally, examples of methods and reagents particularly amenable for use in generating and screening antibody or antigen binding protein display libraries can be found in the literature. Thus, the epitopes described herein can be used to screen for other antibodies that can be used therapeutically, diagnostically, or as research tools.

Administration, Compositions, and Kits Comprising the Antibodies

Whereas, an isolated antibody of the present invention binds an epitope on a CHIKV protein and displays in vitro and/or in vivo CHIKV inhibiting or therapeutic activities, the antibodies or antigen binding fragments thereof, capable of inhibiting CHIKV infection and symptoms, are suitable both as therapeutic and prophylactic agents for treating or preventing CHIKV-associated conditions in humans and animals.

In general, use will comprise administering a therapeutically or prophylactically effective amount of one or more monoclonal antibodies or antigen binding fragments of the antibodies described herein to a susceptible subject or to one exhibiting a condition in which CHIKV is known to have caused the pathology observed. Any active form of the antibody can be administered, including, but not limited to Fab and F(ab')2 fragments.

In some embodiments, the antibodies used are compatible with the recipient species such that the immune response to the MAbs does not result in an unacceptably short circulating half-life or induce an immune response to the MAbs in the subject. In some embodiments, the MAbs administered exhibit some secondary functions such as binding to Fc receptors of the subject and activation of antibody dependent cell mediated cytotoxicity (ADCC) mechanisms.

Treatment of individuals may comprise the administration of a therapeutically effective amount of the antibodies described herein. The antibodies can be provided in a kit as described below. The antibodies can be used or administered alone or in admixture with another therapeutic, analgesic, or diagnostic agent. In providing a patient with an antibody, or fragment thereof, capable of binding to a CHIKV protein, or an antibody capable of protecting against CHIKV pathology in a recipient patient, the dosage of administered agent will vary depending upon such factors as the patient's age, weight, height, sex, general medical condition, previous medical history, etc.

Suitable vehicles and their formulation and packaging are described, for example, in Remington: The Science and Practice of Pharmacy (21st ed., Troy, D. ed., Lippincott Williams & Wilkins, Baltimore, Md. (2005) Chapters 40 and 41). Additional pharmaceutical methods may be employed to control the duration of action. Controlled release preparations may be achieved through the use of polymers to complex or absorb the compounds. Another possible method to control the duration of action by controlled release preparations is to incorporate the compounds of the present invention into particles of a polymeric material such as polyesters, polyamino acids, hydrogels, poly(lactic acid) or ethylene vinylacetate copolymers. Alternatively, instead of incorporating these agents into polymeric particles, it is possible to entrap these materials in microcapsules prepared, for example, interfacial polymerization, for example, hydroxymethylcellulose or gelatin-microcapsules and poly (methylmethacylate)-microcapsules, respectively, or in colloidal drug delivery systems, for example, liposomes, albumin microspheres, microemulsions, nanoparticles, and nanocapsules or in macroemulsions.

In general, if administering a systemic dose of the antibody, it is desirable to provide the recipient with a dosage of antibody which is in the range of from about 1 ng/kg-100 ng/kg, 100 ng/kg-500 ng/kg, 500 ng/kg-1 ug/kg, 1 ug/kg-100 ug/kg, 100 ug/kg-500 ug/kg, 500 ug/kg-1 mg/kg, 1 mg/kg-50 mg/kg, 50 mg/kg-100 mg/kg, 100 mg/kg-500 mg/kg (body weight of recipient), although a lower or higher dosage may be administered. Dosages as low as about 1.0 mg/kg may be expected to show some efficacy. Preferably, about 5 mg/kg is an acceptable dosage, although dosage levels up to about 50 mg/kg are also preferred especially for therapeutic use. Alternatively, administration of a specific amount of the antibody may be given which is not based upon the weight of the patient such as an amount in the range of 1 ug-100 ug, 1 mg-100 mg, or 1 gm-100 gm. For example, site specific administration may be to body compartment or cavity such as intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, vaginal, rectal, buccal, sublingual, intranasal, or transdermal means.

The antibody compositions described herein can be prepared for use for parenteral (subcutaneous, intramuscular or intravenous) or any other administration particularly in the form of liquid solutions or suspensions. The formulation can also be suitable for an injectable formulation. In some embodiments, the injectable formulation is sterile. In some embodiments, the injectable formulation is pyrogen free. In some embodiments, the formulation is free of other antibodies that bind to other antigens other than an antigen described herein.

In a similar approach, another therapeutic use of the antibody of the present invention is the active immunization of a patient using an anti-idiotypic antibody raised against one of the present antibodies. Immunization with an anti-idiotype which mimics the structure of the epitope could elicit an active CHIKV response.

Likewise, active immunization can be induced by administering one or more antigenic and/or immunogenic epitopes as a component of a vaccine. Vaccination could be performed orally or parenterally in amounts sufficient to enable the recipient to generate protective antibodies against this biologically functional region, prophylactically or therapeutically. For example, CHIKV epitopes are described herein. These epitopes can be administered as part of a vaccine. The host can be actively immunized with the antigenic/immunogenic peptide in pure form, a fragment of the peptide, or a modified form of the peptide. One or more amino acids, not corresponding to the original protein sequence can be added to the amino or carboxyl terminus of the original peptide, or truncated form of peptide. Such extra amino acids are useful for coupling the peptide to another peptide, to a large carrier protein, or to a support. Amino acids that are useful for these purposes include: tyrosine, lysine, glutamic acid, aspartic acid, cysteine and derivatives thereof.

Alternative protein modification techniques may be used e.g., NH2-acetylation or COOH-terminal amidation, to provide additional means for coupling or fusing the peptide to another protein or peptide molecule or to a support. An embodiment of an immunogenic epitope is one that encompasses residues of CHIKV. In a particular embodiment of a peptide or protein comprising antigen epitope, the peptide displays a mimitope which mimics the spatial association of epitopes (see FIGS. 3 and 4) of CHIKV or variants as shown by X-ray crystallography.

An antibody, capable of protecting against CHIKV infection or use to treat a CHIKV infection or pathology, is intended to be provided to subjects in an amount sufficient to affect a reduction, resolution, or amelioration in the CHIKV-related symptom or pathology. An amount is said to be sufficient or a "therapeutically effective amount" to "affect" the reduction of symptoms if the dosage, route of administration, and dosing schedule of the agent are sufficient to influence such a response. Responses to antibody administration can be measured by analysis of subject's affected tissues, organs, or cells as by imaging techniques or by ex vivo analysis of tissue samples. An agent is physiologically significant if its presence results in a detectable change in the physiology of a recipient patient.

The antibodies of the present invention can be formulated according to known methods to prepare pharmaceutically useful compositions, whereby these materials, or their functional derivatives, are combined in admixture with a pharmaceutically acceptable carrier vehicle. The treatment may be given in a single dose schedule, or a multiple dose schedule in which a primary course of treatment may be with 1-10 separate doses, followed by other doses given at subsequent time intervals required to maintain and or reinforce the response, for example, at 1-4 months for a second dose, and if needed, a subsequent dose(s) after several months. Examples of suitable treatment schedules include: (i) 0, 1 month and 6 months, (ii) 0, 7 days and 1 month, (iii) 0 and 1 month, (iv) 0 and 6 months, or other schedules sufficient to elicit the desired responses expected to reduce disease symptoms, or reduce severity of disease.

Embodiments provided herein also provide methods of treating, inhibiting or ameliorating a CHIKV infection comprising administering an antibody described herein or a pharmaceutical composition comprising an antibody described herein. In some embodiments, the method reduces a pathology associated with CHIKV infection. In some embodiments, the method alleviates the symptoms of CHIKV associated acute and/or chronic polyarthritis/polyarthralgia, fever, rash, myalgia, and/or fatigue. In some embodiments, the antibody is administered to a subject in a pharmaceutical composition or formulation. In some embodiments, the method reduces the pain in the subject associated with the CHIKV infection. In some embodiments, the method alleviates a symptom associated CHIKV infection. In some embodiments, the antibody can cross-react and treat a symptom of other alphaviruses. Examples include, but are not limited to, O'nyong Nyong (ONNV), Ross River (RRV), Semliki Forest (SFV), Barmah Forest (BFV), Sindbis (SINV), Western Equine Encephalitis (WEEV), Eastern Equine Encephalitis (EEEV), Venezuelan Equine Encephalitis (VEEV), and the like. The symptoms treated or alleviated can include pain, fever, and the like.

In some embodiments methods of detecting the presence or absence of a CHIKV antigen in a sample are provided. In some embodiments, the method comprises contacting a sample with an antibody described herein and detecting the binding to a CHIKV antigen by the antibody, wherein the detection of the binding indicates the presence of CHIKV antigen; or the absence of the detection of the binding to the CHIKV antigen indicates the absence of the CHIKV antigen.

In some embodiments, methods of identifying an antibody that binds to an epitope, wherein the epitope comprises residues:

E2-G95;

E2-A162;

E2-159-171;

E2-A164, E2-E165, E2-E166 and/or E2-I167;

E2-Y69, E2-F84, E2-V113, E2-G114, E2-T116, and/or E2-D117;

at least one of Subunit I-E2-E24 and Subunit I-E2-I121 and at least one of: Subunit II-E2-G55, Subunit II-E2-W64, Subunit II-E2-K66, Subunit II-E2-R80; any combination thereof are provided. In some embodiments, the method comprises contacting a test antibody with the epitope and determining whether the test antibody binds to the epitope. Determining whether the antibody binds to the epitope can be done through any well-known method such as using a biosensor, ELISA, competitive inhibition, and the like. In some embodiments, the epitope comprises Subunit I-E2-E24 and Subunit I-E2-I121 and at least one of: Subunit II-E2-G55, Subunit II-E2-W64, Subunit II-E2-K66, Subunit II-E2-R80. In some embodiments, epitope comprises Subunit I-E2-E24 and Subunit I-E2-I121 and at least two of Subunit II-E2-G55, Subunit II-E2-W64, Subunit II-E2-K66, Subunit II-E2-R80. In some embodiments, the epitope comprises Subunit I-E2-E24 and Subunit I-E2-I121 and at least three of Subunit II-E2-G55, Subunit II-E2-W64, Subunit II-E2-K66, Subunit II-E2-R80. In some embodiments, the determining whether an antibody comprising a sequence selected from the group consisting of SEQ ID NOs: 1-26 competitively inhibits the binding of the test binding to the epitope. In some embodiments, the determining comprises mutating one or more residues of epitope and determining binding of the test epitope, wherein if the mutation reduces binding of the test antibody, the test antibody is deemed to bind to that epitope. In some embodiments, the epitope comprises a residue from the E2 Domain A (E2DA). In some embodiments, the residue from the E2 Domain A (E2DA) is E24, G55, W64, K66, H73, 174, R80, H99, or I121. In some embodiments, the epitope comprises each of the residues of E24, G55, W64, K66, H73, 174, R80, H99, and I121. In some embodiments, the epitope comprises at least 1, 2, 3, 4, 5, 6, 7, or 8 of the residues from E2DA including, but not limited to the ones described herein. In some embodiments, the epitope comprises a residue from E2 Arch 1. In some embodiments, the residue from E2 Arch 1 is Q146, A162, or M171. In some embodiments, the epitope comprises each of the residues of Q146, A162, and M171. In some embodiments, the epitope comprises at least 2 of the residues, including, but not limited to, two of Q146, A162, and M171. In some embodiments, the epitope comprises a residue from the E2 Domain B (E2DB). In some embodiments, the residue from E2DB is Q195, T196, Y199, C201, G209, T212, or N231. In some embodiments, the epitope comprises each of the residues of Q195, T196, Y199, C201, G209, T212, and N231. In some embodiments, the epitope comprises at least 1, 2, 3, 4, 5, or 6 of Q195, T196, Y199, C201, G209, T212, and N231. In some embodiments, the epitope comprises a residue from E2 Arch 2. In some embodiments, the epitope comprises K233 and/or M267 from E2 Arch 2. In some embodiments, the epitope comprises a residue from the E1 Fusion Loop (E1FL). In some embodiments, the residues from E1FL is G83, Y85, F87, W89, D97, or N100. In some embodiments, the epitope comprises each of G83, Y85, F87, W89, D97, and N100. In some embodiments, the epitope comprises at least 1, 2, 3, 4, or 5 of: G83, Y85, F87, W89, D97, and N100. In some embodiments, the epitope comprises a residue from the E1 Domain II (E1DII). In some embodiments, the residue from E1DII is T228. Therefore, in some embodiments, the epitope comprises a residue from each of or 1, 2, 3, 4 of the regions of: E2DA, E2 Arch 1, E2DB, E2 Arch 2, E1FL, and E1DII. In some embodiments, the residue is a residue described herein and/or above.

In some embodiments, methods of inducing an immune response against a a CHIKV antigen fragment are provided. In some embodiments, the method comprises administering a CHIKV antigen fragment to a subject under conditions sufficient to induce an immune response. In some embodiments, the antigen fragment is a E1/E2 heterodimer. In some embodiments, the antigen fragment is E2 protein or a fragment thereof. In some embodiments, the antigen comprises residues:

E2-G95;

E2-A162;

E2-159-171;

E2-A164, E2-E165, E2-E166 and/or E2-I167;

E2-Y69, E2-F84, E2-V113, E2-G114, E2-T116, and/or E2-D117;

at least one, or both of, of Subunit I-E2-E24 and Subunit I-E2-I121 and at least one, two, three, or all, of: Subunit II-E2-G55, Subunit II-E2-W64, Subunit II-E2-K66, Subunit II-E2-R80; or any combination thereof. In some embodiments, the subject is a human. In some embodiments, the subject is a mammal. In some embodiments, the subject is a rodent or sheep. In some embodiments, the antigen fragment comprises 5-70 residues of CHIKV E2 protein. In some embodiments, the fragment comprises residues 159-171 of E2. In some embodiments, the fragment comprises residues 69-117 of E2. The antigen can also be introduced using a nucleic acid molecule that encodes the antigen. Methods of introducing antigens by using a nucleic acid molecule encoding a polypeptide are well-known and any particular method can be used. In some embodiments, the antigen comprises an epitope as described herein. In some embodiments, the epitope comprises a residue from the E2 Domain A (E2DA). In some embodiments, the residue from the E2 Domain A (E2DA) is E24, G55, W64, K66, H73, 174, R80, H99, or 1121. In some embodiments, the epitope comprises each of the residues of E24, G55, W64, K66, H73, 174, R80, H99, and I121. In some embodiments, the epitope comprises at least 1, 2, 3, 4, 5, 6, 7, or 8 of the residues from E2DA including, but not limited to the ones described herein. In some embodiments, the epitope comprises a residue from E2 Arch 1. In some embodiments, the residue from E2 Arch 1 is Q146, A162, or M171. In some embodiments, the epitope comprises each of the residues of Q146, A162, and M171. In some embodiments, the epitope comprises at least 2 of the residues, including, but not limited to, two of Q146, A162, and M171. In some embodiments, the epitope comprises a residue from the E2 Domain B (E2DB). In some embodiments, the residue from E2DB is Q195, T196, Y199, C201, G209, T212, or N231. In some embodiments, the epitope comprises each of the residues of Q195, T196, Y199, C201, G209, T212, and N231. In some embodiments, the epitope comprises at least 1, 2, 3, 4, 5, or 6 of Q195, T196, Y199, C201, G209, T212, and N231. In some embodiments, the epitope comprises a residue from E2 Arch 2. In some embodiments, the epitope comprises K233 and/or M267 from E2 Arch 2. In some embodiments, the epitope comprises a residue from the E1 Fusion Loop (E1FL). In some embodiments, the residues from E1FL is G83, Y85, F87, W89, D97, or N100. In some embodiments, the epitope comprises each of G83, Y85, F87, W89, D97, and N100. In some embodiments, the epitope comprises at least 1, 2, 3, 4, or 5 of: G83, Y85, F87, W89, D97, and N100. In some embodiments, the epitope comprises a residue from the E1 Domain II (E1DII). In some embodiments, the residue from E1DII is T228. Therefore, in some embodiments, the epitope comprises a residue from each of or 1, 2, 3, 4 of the regions of: E2DA, E2 Arch 1, E2DB, E2 Arch 2, E1FL, and E1DII. In some embodiments, the residue is a residue described herein and/or above.

In some embodiments, an isolated composition comprising an antibody bound to a CHIKV protein is provided. In some embodiments, the antibody is bound to an epitope comprising residues:

E2-G95;

E2-A162;

E2-159-171;

E2-A164, E2-E165, E2-E166 and/or E2-I167;

E2-Y69, E2-F84, E2-V113, E2-G114, E2-T116, and/or E2-D117;

at least one, or both, of Subunit I-E2-E24 and Subunit I-E2-I121 and at least one, two, three, or all, of: Subunit II-E2-G55, Subunit II-E2-W64, Subunit II-E2-K66, Subunit II-E2-R80; or any combination thereof. As described herein, the antibody can be a monoclonal antibody or a recombinant antibody. In some embodiments, the antibody is a is a chimeric, human, or humanized antibody. In some embodiments, the antibody is bound to an epitope comprising residues as described herein. In some embodiments, the epitope comprises a residue from the E2 Domain A (E2DA). In some embodiments, the residue from the E2 Domain A (E2DA) is E24, G55, W64, K66, H73, 174, R80, H99, or I121. In some embodiments, the epitope comprises each of the residues of E24, G55, W64, K66, H73, 174, R80, H99, and I121. In some embodiments, the epitope comprises at least 1, 2, 3, 4, 5, 6, 7, or 8 of the residues from E2DA including, but not limited to the ones described herein. In some embodiments, the epitope comprises a residue from E2 Arch 1. In some embodiments, the residue from E2 Arch 1 is Q146, A162, or M171. In some embodiments, the epitope comprises each of the residues of Q146, A162, and M171. In some embodiments, the epitope comprises at least 2 of the residues, including, but not limited to, two of Q146, A162, and M171. In some embodiments, the epitope comprises a residue from the E2 Domain B (E2DB). In some embodiments, the residue from E2DB is Q195, T196, Y199, C201, G209, T212, or N231. In some embodiments, the epitope comprises each of the residues of Q195, T196, Y199, C201, G209, T212, and N231. In some embodiments, the epitope comprises at least 1, 2, 3, 4, 5, or 6 of Q195, T196, Y199, C201, G209, T212, and N231. In some embodiments, the epitope comprises a residue from E2 Arch 2. In some embodiments, the epitope comprises K233 and/or M267 from E2 Arch 2. In some embodiments, the epitope comprises a residue from the E1 Fusion Loop (E1FL). In some embodiments, the residues from E1FL is G83, Y85, F87, W89, D97, or N100. In some embodiments, the epitope comprises each of G83, Y85, F87, W89, D97, and N100. In some embodiments, the epitope comprises at least 1, 2, 3, 4, or 5 of: G83, Y85, F87, W89, D97, and N100. In some embodiments, the epitope comprises a residue from the E1 Domain II (E1DII). In some embodiments, the residue from E1DII is T228. Therefore, in some embodiments, the epitope comprises a residue from each of or 1, 2, 3, 4 of the regions of: E2DA, E2 Arch 1, E2DB, E2 Arch 2, E1FL, and E1DII. In some embodiments, the residue is a residue described herein and/or above.

The present invention also provides kits which are useful for carrying out the present invention. The present kits comprise a first container containing or packaged in association with the above-described antibodies. The kit may also comprise another container containing or packaged in association solutions necessary or convenient for carrying out the invention. The containers can be made of glass, plastic or foil and can be a vial, bottle, pouch, tube, bag, etc. The kit may also contain written information, such as procedures for carrying out the present invention or analytical information, such as the amount of reagent contained in the first container means. The container may be in another container apparatus, e.g. a box or a bag, along with the written information.

Yet another aspect is a kit for detecting CHIKV protein in a biological sample. The kit includes a container holding one or more antibodies which binds an epitope of CHIKV protein and instructions for using the antibody for the purpose of binding to CHIKV protein to form an immunological complex and detecting the formation of the immunological complex such that the presence or absence of the immunological complex correlates with presence or absence of CHIKV protein in the sample. Examples of containers include multiwell plates which allow simultaneous detection of CHIKV protein in multiple samples.

Various sequences are referenced herein. The sequences include the following: Sequences and reference can be made to the following table ("VH" refers to variable heavy chain; "VL" refers to variable light chain)

| | |
|---|---|
| CAP101A-E8(IM-CKV056)\VH (SEQ ID NO: 1) | QVQLVQSGGGVVQPGRSLRLSCAASGFTLSTYGLHWVRQAPGKGLEWVAVISYDGTNKYYADSVKGRFTVSWDNSKNTLYLQMNSLRAEDTAVYYCAKDLASSSWSDYYHYGMDVWGQGTMVTVSS |
| CAP101A-E8(IM-CKV056)\VL (SEQ ID NO: 2) | DIQLTQSPSTLSASVGDRITITCRATQSIGSWLAWYQQKPGKAPKLLIYKASSLESGVPSRFSGSGSATEFTLTISGLQPEDFATYYCQQLKSFPLTFGPGTKVDIQ |
| CAP1A-B3(IM-CKV067)\[1A2-3]\VH (SEQ ID NO: 3) | QLQLQESGPGLVKPSDTLSLTCSVSGDSISSSYWSWIRQPPGKGLEWIGAIHYSGSTNYNPSLKSRVAISVDTAQNHFSLKLSSLTAADTAVYYCARTGCTNGVCYPSFDYWGQGTLVTVSS |
| CAP1A-B3 (IM-CKV067)\[1A2-3]\VL (SEQ ID NO: 4) | DIQLTQSPSSVSASVGDRVTITCRASQGIGSRLAWYQQKPGKAPKLLIYVASSLQSGVPSRFSGSGSATDFTLTISSLQPEDFATYYCQQADSFPLTFGGGTRVEIK |
| CAP1A-B5(IM-CKV066)\[1A2-5]\VH (SEQ ID NO: 5) | EVQLVESGGGLVQPGGSLRLSCAASGFAFRSYAMTWVRQAPGKGLEWVSTISGSTGDTYYADSVEGRFTISRDNSKDTLYLQMKNLGGDDTAVYYCARVLGTGWFDPWGQGTLVTVSS |
| CAP1A-B5(IM-CKV066)\[1A2-5]\VL (SEQ ID NO: 6) | EIVLTQSPDSLAVSLGERATINCKSSQSVLYSSNNKNYFAWYQQKPGQPPKLLISWASTRASGVPDRFSGSGSGTEFTLTISSLQPEDVAVYYCQQYYSPTRTFGQGTKVEIK |
| CAP4A-E4\[4-4]\VH (SEQ ID NO: 7) | QVQLQESGPGLVKPSDTLSLTCSVSGDSISSSYWSWIRQPPGKGLEWIGAIHYSGSTNYNPSLKSRVAISVDTAQNHFSLKLSSLTAADTAVYYCARTGCTNGVCYPSFDYWGQGTLVTVSS |
| CAP4A-E4\[4-4]\VL (SEQ ID NO: 8) | EIVLTQSPLSLTVTLGQPASISCRSSQSLVHSDGNTYLNWFQQRPGQSPRRLIYKVSNRDSGVPDRFSGSGSGTDFTLKISRVEAEDVGVYYCMQGTGWPWTFGQGTKVEIR |
| CAP4A-E5(IM-CKV064)\[4-5]\VH (SEQ ID NO: 9) | EVQLVQSGPEVKKPGASVKVSCKASGYTFSNYGVSWVRQAPGQGLEWLGWISAYNGNTKYAQKFEGRVTLTTDSLSDTAYMELRSLRSDDTAVYYCVRDDRSGYYYLPFDFWGQGTLVTVSS |
| CAP4A-E5(IM-CKV064)\[4-5]\VL (SEQ ID NO: 10) | DIQLTQSPSSVSASVGDGVTITCRASQGISSWLAWYQQKPGKAPKLLIYAASSLQSGVPSRFSGSGSGTDFTLTISSLQPEDFATYYCQQANSFPYTFGQGTKLEIK |
| CAP4A-E6\[4-6]\VH (SEQ ID NO: 11) | QVQLQESGPGLVKPSDTLSLTCSVSGDSISSSYWSWIRQPPGKGLEWIGAIHYSGSTNYNPSLKSRVAISVDTAQNHFSLKLSSLTAADTAVYYCARTGCTNGVCYPSFDYWGRGTLVTVSS |
| CAP4A-E6\[4-6]\VL (SEQ ID NO: 12) | DIQLTQSPSSVSASVGDRVTITCRASQGITNLLGWYQHKPGEAPKLLIYTSSTLQPGVPSRFRGSGSGTDFSLTITSLQPEDFATYFCQQAHSFPLTFGGGTKVEIR |
| CAP4A-E7(IM-CKV063)\[4-7]\VH (SEQ ID NO: 13) | QVQLVQSGAEVKKPGSAVKVSCKASGGTLRKYAISWLRQAPGQGLEWMGGIIPIFGTANYAQKFQGRVTITADESTTTPYTTTPYTSTAYIELTSLRSEDTAVYYCARDLGPLTGYSYSYFDYWGQGTLVTVSS |
| CAP4A-E7(IM-CKV063)\[4-7]\VL (SEQ ID NO: 14) | EIVMTQSPATLSLSPGERATLSCRASQSVSSYLAWYQQKPGQAPRLLIYDASNRATGIPDRFSGSGSGTDFTLTISRLEPEDFAVYYCQQYANSRRTFGQGTKVEIT |
| CAP5A-F6(IM-CKV065)\[5-6]\VH (SEQ ID NO: 15) | EVQLVQSGPEVKKPGASVKVSCKASGYTFSNYGVSWVRQAPGQGLEWLGWISAYNGNTKYAQKFEGRVTLTTDSLSDTAYMELRSLRSDDTAVYYCVRDDRSGYYYLPFDFWGQGTLVTVSS |
| CAP5A-F6(IM-CKV065)\[5-6]\VL (SEQ ID NO: 16) | DIQLTQSPSFLSASVGDRVTITCRASQGISSYLAWYQQKPGKAPKLLIFAASTLQSGVPSRFSGSGSGTDYTLTISSLQPEDFATYYCQQSYSNPTFGQGTRLEIK |
| ChikV\C9\VH (SEQ ID NO: 17) | EVQLVQSGAEVKKPGSSVKVSCKAFGGTFSSYAITWVRQAPGQGLEWMGGIIPILGTTDYAQKFQGRVTITADKSTSTAYMELSSLRSEDTAVYYCARDPPTHGGDFNYYYYGVAVWGQGTTVTVSS |
| ChikV\C9\VL (SEQ ID NO: 18) | EIVLTQSPGTLSLSPGERATLSCRASQSNNYLAWYQQKPGQAPRLLIYGASIRATGIPDRFSGSGSGTDFTLTISRLAPEDFAVYYCQQYGSSPLTFGPGTKVDIK |
| CNP1A-H5\VH (SEQ ID NO: 19) | EVQLVESGGDLVQPGGSLTPSCVISEFTFSTSWMGWVRQAPGKGLECVASIKTDGSEKYYVDSVKGRFTISRDNAKNSLYLQMNSLRVADTAVYYCARHGAYTYDSWGPGTLVTVSS |

-continued

CNP1A_H5_VL (SEQ ID NO: 20)

```
DIQLTQSPDSLAVSLGERATINCKSS
QSILYSSDNKNYLSWIQQKPGQPPKV
LIYWASTRESGVPDRFSGSGSGTDFT
LTISSLQAEDVAVYYCQQYYRTPITF
GQGTRLEIK
```

CNP2B-H12(IM-CKV057)\VH (SEQ ID NO: 21)

```
QVQLQESGPGLVKPSDTLSLTCSVSG
DSISSSYWSWIRQPPGKGLEWIGAIH
YSGSTNYNPSLKSRVAMSVDTAQNHF
SLKLSSLTAADTAVYYCARTGCTNGV
CYPSFDYWGQGTLVTVSS
```

CNP2B-H12(IM-CKV057)\VL (SEQ ID NO: 22)

```
EIVMTQSPATLSLSPGERATLSCRAS
QSVSSYLAWYQQKPGQAPRLLIYDAS
NRATGIPARFSGSGSGTDFTLTISSL
EPEDFAVYYCQQRSNWPPTFGQGTKV
EIK
```

CNP4A-E4\[4-4]\VH (IM-CKV062) (SEQ ID NO: 23)

```
QVQLQESGPGLVKPSDTLSLTCSVSG
DSISSSYWSWIRQPPGKGLEWIGAIH
YSGSTNYNPSLKSRVAISVDTAQNHF
SLKLSSLTAADTAVYYCARTGCTNGV
CYPSFDYWGQGTLVTVSS
```

CNP4A-E4\[4-4]\VL (IM-CKV062) (SEQ ID NO: 24)

```
EIVLTQSPLSLTVTLGQPASISCRSS
QSLVHSDGNTYLNWFQQRPGQSPRRL
IYKVSNRDSGVPDRFSGSGSGTDFTL
KISRVEAEDVGVYYCMQGTGWPWTFG
QGTKVEIR
```

CNP4A-E6\[4-6]\VH (IM-CKV061) (SEQ ID NO: 25)

```
QVQLQESGPGLVKPSDTLSLTCSVSG
DSISSSYWSWIRQPPGKGLEWIGAIH
YSGSTNYNPSLKSRVAISVDTAQNHF
SLKLSSLTAADTAVYYCARTGCTNGV
CYPSFDYWGRGTLVTVSS
```

CNP4A-E6\[4-6]\VL (IM-CKV061) (SEQ ID NO: 26)

```
DIQLTQSPSSVSASVGDRVTITCRAS
QGITNLLGWYQHKPGEAPKLLIYTSS
TLQPGVPSRFRGSGSGTDFSLTITSL
QPEDFATYFCQQAHSFPLTFGGGTKV
EIR
```

CHIKV_ENV_S27_AA (SEQ ID NO: 27)

```
MSLAIPVMCLLANTTFPCSQPPCIPC
CYEKEPEETLRMLEDNVMRPGYYQLL
QASLTCSPHRQRRSTKDNFNVYKATR
PYLAHCPDCGEGHSCHSPVALERIRN
EATDGTLKIQVSLQIGIGTDDSHDWT
KLRYMDNHIPADAGRAGLFVRTSAPC
TITGTMGHFILARCPKGETLTVGFTD
SRKISHSCTHPFHHDPPVIGREKFHS
RPQHGKELPCSTYVQSNAATAEEIEV
HMPPDTPDRTLLSQQSGNVKITVNSQ
TVRYKCNCGGSNEGLITTDKVINNCK
VDQCHAAVTNHKKWQYNSPLVPRNAE
LGDRKGKIHIPFPLANVTCMVPKARN
PTVTYGKNQVIMLLYPDHPTLLSYRS
MGEEPNYQEEWVTHKKEVVLTVPTEG
LEVTWGNNEPYKYWPQLSANGTAHGH
PHEIILYYYELYPTMTVVVVSVASFI
LLSMVGMAVGMCMCARRRCITPYELT
PGATVPFLLSLICCIRTAKAATYQEA
AVYLWNEQQPLFWLQALIPLAALIVL
CNCLRLLPCCCKTLAFLAVMSIGAHT
VSAYEHVTVIPNTVGVPYKTLVNRPG
YSPMVLEMELLSVTLEPTLSLDYITC
EYKTVIPSPYVKCCGTAECKDKNLPD
YSCKVFTGVYPFMWGGAYCFCDAENT
QLSEAHVEKSESCKTEFASAYRAHTA
SASAKLRVLYQGNNITVTAYANGDHA
VTVKDAKFIVGPMSSAWTPFDNKIVV
YKGDVYNMDYPPFGAGRPGQFGDIQS
RTPESKDVYANTQLVLQRPAAGTVHV
PYSQAPSGFKYWLKERGASLQHTAPF
GCQIATNPVRAMNCAVGNMPISIDIP
DAAFTRVVDAPSLTDMSCEVPACTHS
SDFGGVAIIKYAVSKKGKCAVHSMTN
AVTIREAEIEVEGNSQLQISFSTALA
SAEFRVQVCSTQVHCAAECHPPKDHI
VNYPASHTTLGVQDISATAMSWVQKI
TGGVGLVVAVAALILIVVLCVSFSRH
```

CHIKV_ENV_S27_NT (SEQ ID NO: 28)

```
ATGTCACTAGCCATCCCTGTGATGTG
TCTGCTCGCCAACACAACTTTCCCAT
GCTCTCAGCCACCCTGTATACCCTGC
TGCTATGAGAAAGAACCTGAGGAGAC
CCTGCGCATGCTGGAGGACAATGTTA
TGAGGCCAGGCTACTACCAACTATTG
CAGGCAAGTTTGACCTGCTCACCACA
TAGGCAGCGCCGATCCACAAAAGATA
ACTTCAACGTTTACAAAGCTACTCGA
CCCTATTTGGCCCACTGCCCGGATTG
TGGGGAAGGACACTCCTGCCACTCTC
CCGTGGCCCTCGAACGAATTAGGAAC
GAGGCTACTGACGGAACCCTAAAGAT
TCAGGTATCACTCCAGATCGGAATAG
GGACAGACGACTCTCACGATTGGACA
AAACTCAGATATATGGATAACCACAT
CCCCGCCGACGCTGGCAGAGCCGGTC
TTTTCGTTCGCACATCCGCTCCCTGC
ACAATAACGGGTACCATGGGGCATTT
CATTCTGGCGCGGTGCCCGAAGGGAG
AGACCCTTACAGTGGGCTTTACCGAC
TCCCGCAAGATTTCTCATAGCTGTAC
CCATCCCTTCCATCACGATCCTCCTG
TAATCGGCCGGGAGAAATTCCACTCC
CGGCCGCAACATGGCAAAGAGCTGCC
CTGTTCTACCTATGTACAAAGCAACG
CCGCGACTGCCGAGGAAATAGAGGTG
CACATGCCACCAGATACCCCCGATCG
AACACTTCTTTCTCAACAAAGTGGCA
ACGTAAAAATCACAGTTAACAGCCAG
ACTGTGCGGTATAAGTGCAACTGTGG
GGGTTCCAATGAAGGCCTCATCACGA
CTGACAAGGTGATCAATAACTGCAAG
GTCGACCAGTGTCACGCCGCGGTGAC
GAATCACAAAAAGTGGCAGTATAACT
CTCCGCTTGTGCCACGTAACGCCGAG
CTGGGGGATAGAAAGGGGAAGATCCA
CATCCCCTTTCCACTGGCTAATGTCA
CGTGCATGGTGCCGAAGGCTAGAAAT
CCTACAGTAACTTACGGAAAGAATCA
AGTGATCATGTTATTATATCCTGACC
ATCCGACTCTCCTGAGTTATAGATCA
ATGGGCGAAGAACCTAACTACCAAGA
AGAGTGGGTCACCCACAAGAAGGAGG
TGGTTTTAACAGTGCCAACCGAAGGT
CTTGAAGTGACCTGGGGCAATAACGA
ACCCTACAAGTATTGGCCACAGCTGT
CCGCTAATGGCACGGCCCACGGTCAC
CCCCACGAGATCATACTGTACTACTA
TGAACTATACCCTACTATGACCGTGG
TGGTGGTGAGCGTGGCCTCCTTCATT
CTCCTCAGCATGGTGGGGATGGCTGT
CGGAATGTGCATGTGCGCGCGCCGGC
GATGTATTACGCCTTACGAGCTGACT
CCCGGCGCCACCGTTCCGTTTCTGCT
AAGCTTGATCTGTTGTATCAGGACGG
CCAAGGCAGCTACCTATCAGGAGGCG
GCTGTATACCTCTGGAACGAGCAGCA
GCCACTCTTCTGGCTTCAGGCCCTGA
TCCCCTTGGCAGCCCTCATAGTGCTG
TGCAACTGTCTGCGTCTGCTCCCATG
TTGTTGCAAGACACTGGCCTTCCTGG
CAGTGATGAGCATTGGCGCGCACACT
GTTTCAGCCTATGAACATGTGACCGT
AATTCCTAACACTGTCGGGGTGCCCT
ACAAGACCTTGGTTAACCGCCCGGGG
TATAGCCCCATGGTTCTCGAGATGGA
ACTTCTGTCGGTAACGTTGGAGCCGA
CCCTTTCCCTTGACTATATTACATGT
GAGTACAAGACGGTGATTCCATCTCC
CTACGTGAAGTGCTGCGGTACTGCTG
AATGCAAGGACAAAAATCTCCCTGAT
TACTCGTGCAAGGTATTCACTGGAGT
GTACCCATTTATGTGGGGAGGCGCTT
ATTGTTTCTGTGATGCTGAAAACACC
CAATTATCTGAAGCCCATGTGGAGAA
```

-continued

```
                      AAGCGAGTCCTGTAAAACTGAGTTCG
                      CCAGCGCCTATCGTGCGCACACCGCT
                      TCTGCCTCCGCCAAGCTTAGGGTGCT
                      ATACCAGGGCAATAATATAACCGTTA
                      CTGCATATGCGAACGGAGACCATGCA
                      GTTACTGTAAAAGATGCAAAATTTAT
                      AGTGGGCCCCATGAGTTCGGCTTGGA
                      CACCCTTCGACAATAAGATAGTCGTG
                      TACAAGGGCGACGTGTACAATATGGA
                      CTACCCACCTTTCGGCGCTGGCCGTC
                      CTGGTCAGTTCGGAGACATCCAAAGC
                      CGGACACCTGAGTCCAAGGACGTCTA
                      CGCAAACACACAGCTTGTCCTGCAGC
                      GGCCAGCAGCCGGGACAGTTCACGTG
                      CCTTACAGCCAGGCGCCCAGTGGCTT
                      TAAGTATTGGCTAAAGGAAAGGGGGG
                      CGAGTCTCCAGCATACTGCCCCCTTC
                      GGCTGCCAGATTGCAACTAACCCCGT
                      GCGAGCTATGAATTGCGCAGTCGGCA
                      ACATGCCTATCTCTATTGATATCCCG
                      GACGCCGCTTTTACTCGTGTCGTGGA
                      CGCTCCCAGCCTGACGGACATGTCCT
                      GCGAAGTTCCTGCATGCACCCACTCA
                      TCCGATTTTGGAGGTGTGGCAATAAT
                      CAAATATGCAGTCAGTAAAAAGGGTA
                      AGTGTGCCGTCCACTCGATGACGAAT
                      GCCGTGACTATCAGAGAGGCAGAGAT
                      CGAAGTGGAAGGAAATAGCCAGTTGC
                      AAATCTCTTTCAGCACAGCCCTTGCA
                      AGTGCCGAGTTTCGCGTCCAAGTGTG
                      TAGCACGCAGGTTCACTGTGCAGCCG
                      AATGTCATCCGCCTAAAGACCACATA
                      GTCAATTACCCCGCTTCCCACACCAC
                      ATTGGGAGTTCAGGACATAAGTGCTA
                      CTGCTATGAGCTGGGTCCAAAAGATC
                      ACCGGAGGTGTAGGGCTCGTCGTGGC
                      CGTCGCCGCTCTAATTCTGATCGTGG
                      TTCTGTGCGTCAGTTTTTCCCGTCAC

CHIKV_ENV_E1_S27_AA   YEHVTVIPNTVGVPYKTLVNRPGYSP
(SEQ ID NO: 29)       MVLEMELLSVTLEPTLSLDYITCEYK
                      TVIPSPYVKCCGTAECKDKNLPDYSC
                      KVFTGVYPFMWGGAYCFCDAENTQLS
                      EAHVEKSESCKTEFASAYRAHTASAS
                      AKLRVLYQGNNITVTAYANGDHAVTV
                      KDAKFIVGPMSSAWTPFDNKIVVYKG
                      DVYNMDYPPFGAGRPGQFGDIQSRTP
                      ESKDVYANTQLVLQRPAAGTVHVPYS
                      QAPSGFKYWLKERGASLQHTAPFGCQ
                      IATNPVRAMNCAVGNMPISIDIPDAA
                      FTRVVDAPSLTDMSCEVPACTHSSDF
                      GGVAIIKYAVSKKGKCAVHSMTNAVT
                      IREAEIEVEGNSQLQISFSTALASAE
                      FRVQVCSTQVHCAAECHPPKDHIVNY
                      PASHTTLGVQDISATAMSWVQKITGG
                      VGLVVAVAALILIVVLCVSFSRH

CHIKV_ENV_E1_S27_NT   TATGAACATGTGACCGTAATTCCTAA
(SEQ ID NO: 30)       CACTGTCGGGGTGCCCTACAAGACCT
                      TGGTTAACCGCCCGGGGTATAGCCCC
                      ATGGTTCTCGAGATGGAACTTCTGTC
                      GGTAACGTTGGAGCCGACCCTTTCCC
                      TTGACTATATTACATGTGAGTACAAG
                      ACGGTGATTCCATCTCCCTACGTGAA
                      GTGCTGCGGTACTGCTGAATGCAAGG
                      ACAAAAATCTCCCTGATTACTCGTGC
                      AAGGTATTCACTGGAGTGTACCCATT
                      TATGTGGGGAGGCGCTTATTGTTTCT
                      GTGATGCTGAAAACACCCAATTATCT
                      GAAGCCCATGTGGAGAAAAGCGAGTC
                      CTGTAAAACTGAGTTCGCCAGCGCCT
                      ATCGTGCGCACACCGCTTCTGCCTCC
                      GCCAAGCTTAGGGTGCTATACCAGGG
                      CAATAATATAACCGTTACTGCATATG
                      CGAACGGAGACCATGCAGTTACTGTA
                      AAAGATGCAAAATTTATAGTGGGCCC
                      CATGAGTTCGGCTTGGACACCCTTCG
                      ACAATAAGATAGTCGTGTACAAGGGC
                      GACGTGTACAATATGGACTACCCACC
```

-continued

```
                      TTTCGGCGCTGGCCGTCCTGGTCAGT
                      TCGGAGACATCCAAAGCCGGACACCT
                      GAGTCCAAGGACGTCTACGCAAACAC
                      ACAGCTTGTCCTGCAGCGGCCAGCAG
                      CCGGGACAGTTCACGTGCCTTACAGC
                      CAGGCGCCCAGTGGCTTTAAGTATTG
                      GCTAAAGGAAAGGGGGGCGAGTCTCC
                      AGCATACTGCCCCCTTCGGCTGCCAG
                      ATTGCAACTAACCCCGTGCGAGCTAT
                      GAATTGCGCAGTCGGCAACATGCCTA
                      TCTCTATTGATATCCCGGACGCCGCT
                      TTTACTCGTGTCGTGGACGCTCCCAG
                      CCTGACGGACATGTCCTGCGAAGTTC
                      CTGCATGCACCCACTCATCCGATTTT
                      GGAGGTGTGGCAATAATCAAATATGC
                      AGTCAGTAAAAAGGGTAAGTGTGCCG
                      TCCACTCGATGACGAATGCCGTGACT
                      ATCAGAGAGGCAGAGATCGAAGTGGA
                      AGGAAATAGCCAGTTGCAAATCTCTT
                      TCAGCACAGCCCTTGCAAGTGCCGAG
                      TTTCGCGTCCAAGTGTGTAGCACGCA
                      GGTTCACTGTGCAGCCGAATGTCATC
                      CGCCTAAAGACCACATAGTCAATTAC
                      CCCGCTTCCCACACCACATTGGGAGT
                      TCAGGACATAAGTGCTACTGCTATGA
                      GCTGGGTCCAAAAGATCACCGGAGGT
                      GTAGGGCTCGTCGTGGCCGTCGCCGC
                      TCTAATTCTGATCGTGGTTCTGTGCG
                      TCAGTTTTTCCCGTCAC

CHIKV_ENV_E2_S27_AA   STKDNFNVYKATRPYLAHCPDCGEGH
(SEQ ID NO: 31)       SCHSPVALERIRNEATDGTLKIQVSL
                      QIGIGTDDSHDWTKLRYMDNHIPADA
                      GRAGLFVRTSAPCTITGTMGHFILAR
                      CPKGETLTVGFTDSRKISHSCTHPFH
                      HDPPVIGREKFHSRPQHGKELPCSTY
                      VQSNAATAEEIEVHMPPDTPDRTLLS
                      QQSGNVKITVNSQTVRYKCNCGGSNE
                      GLITTDKVINNCKVDQCHAAVTNHKK
                      WQYNSPLVPRNAELGDRKGKIHIPFP
                      LANVTCMVPKARNPTVTYGKNQVIML
                      LYPDHPTLLSYRSMGEEPNYQEEWVT
                      HKKEVVLTVPTEGLEVTWGNNEPYKY
                      WPQLSANGTAHGHPHEIILYYYELYP
                      TMTVVVVSVASFILLSMVGMAVGMCM
                      CARRRCITPYELTPGATVPFLLSLIC
                      CIRTAKA

CHIKV_ENV_E2_S27_NT   TCCACAAAAGATAACTTCAACGTTTA
(SEQ ID NO: 32)       CAAAGCTACTCGACCCTATTTGGCCC
                      ACTGCCCGGATTGTGGGGAAGGACAC
                      TCCTGCCACTCTCCCGTGGCCCTCGA
                      ACGAATTAGGAACGAGGCTACTGACG
                      GAACCCTAAAGATTCAGGTATCACTC
                      CAGATCGGAATAGGGACAGACGACTC
                      TCACGATTGGACAAAACTCAGATATA
                      TGGATAACCACATCCCCGCCGACGCT
                      GGCAGAGCCGGTCTTTTCGTTCGCAC
                      ATCCGCTCCCTGCACAATAACGGGTA
                      CCATGGGGCATTTCATTCTGGCGCGG
                      TGCCCGAAGGGAGAGACCCTTACAGT
                      GGGCTTTACCGACTCCCGCAAGATTT
                      CTCATAGCTGTACCCATCCCTTCCAT
                      CACGATCCTCCTGTAATCGGCCGGGA
                      GAAATTCCACTCCCGGCCGCAACATG
                      GCAAAGAGCTGCCCTGTTCTACCTAT
                      GTACAAAGCAACGCCGCGACTGCCGA
                      GGAAATAGAGGTGCACATGCCACCAG
                      ATACCCCCGATCGAACACTTCTTTCT
                      CAACAAAGTGGCAACGTAAAAATCAC
                      AGTTAACAGCCAGACTGTGCGGTATA
                      AGTGCAACTGTGGGGGTTCCAATGAA
                      GGCCTCATCACGACTGACAAGGTGAT
                      CAATAACTGCAAGGTCGACCAGTGTC
                      ACGCCGCGGTGACGAATCACAAAAAG
                      TGGCAGTATAACTCTCCGCTTGTGCC
                      ACGTAACGCCGAGCTGGGGGATAGAA
                      AGGGGAAGATCCACATCCCCTTTCCA
                      CTGGCTAATGTCACGTGCATGGTGCC
```

-continued

| | |
|---|---|
| | GAAGGCTAGAAATCCTACAGTAACTT<br>ACGGAAAGAATCAAGTGATCATGTTA<br>TTATATCCTGACCATCCGACTCTCCT<br>GAGTTATAGATCAATGGGCGAAGAAC<br>CTAACTACCAAGAAGAGTGGGTCACC<br>CACAAGAAGGAGGTGGTTTTAACAGT<br>GCCAACCGAAGGTCTTGAAGTGACCT<br>GGGGCAATAACGAACCCTACAAGTAT<br>TGGCCACAGCTGTCCGCTAATGGCAC<br>GGCCCACGGTCACCCCCACGAGATCA<br>TACTGTACTACTATGAACTATACCCT<br>ACTATGACCGTGGTGGTGGTGAGCGT<br>GGCCTCCTTCATTCTCCTCAGCATGG<br>TGGGGATGGCTGTCGGAATGTGCATG<br>TGCGCGCGCCGGCGATGTATTACGCC<br>TTACGAGCTGACTCCCGGCGCCACCG<br>TTCCGTTTCTGCTAAGCTTGATCTGT<br>TGTATCAGGACGGCCAAGGCA |
| CHIKV_ENV_E3_S27_AA<br>(SEQ ID NO: 33) | MSLAIPVMCLLANTTFPCSQPPCIPC<br>CYEKEPEETLRMLEDNVMRPGYYQLL<br>QASLTCSPHRQRR |
| CHIKV_ENV_E3_S27_NT<br>(SEQ ID NO: 34) | ATGTCACTAGCCATCCCTGTGATGTG<br>TCTGCTCGCCAACACAACTTTCCCAT<br>GCTCTCAGCCACCCTGTATACCCTGC<br>TGCTATGAGAAAGAACCTGAGGAGAC<br>CCTGCGCATGCTGGAGGACAATGTTA<br>TGAGGCCAGGCTACTACCAACTATTG<br>CAGGCAAGTTTGACCTGCTCACCACA<br>TAGGCAGCGCCGA |
| CHIKV_ENV_6K_S27_AA<br>(SEQ ID NO: 35) | ATYQEAAVYLWNEQQPLFWLQALIPL<br>AALIVLCNCLRLLPCCCKTLAFLAVM<br>SIGAHTVSA |
| CHIKV_ENV_6K_S27_NT<br>(SEQ ID NO: 36) | GCTACCTATCAGGAGGCGGCTGTATA<br>CCTCTGGAACGAGCAGCAGCCACTCT<br>TCTGGCTTCAGGCCCTGATCCCCTTG<br>GCAGCCCTCATAGTGCTGTGCAACTG<br>TCTGCGTCTGCTCCCATGTTGTTGCA<br>AGACACTGGCCTTCCTGGCAGTGATG<br>AGCATTGGCGCGCACACTGTTTCAGC<br>C |

The embodiments are now described with reference to the following examples. These examples are provided for the purpose of illustration only and the embodiments should in no way be construed as being limited to these examples, but rather should be construed to encompass any and all variations which become evident as a result of the teaching provided herein. Those of skill in the art will readily recognize a variety of non-critical parameters that could be changed or modified to yield essentially similar results.

7EXAMPLES

Certain names are used interchangeably throughout the examples and the present specification (including the figures). The following list shows an initial name with the equivalent name shown in parentheses: IM-CKV056 (CAP101A.E8), IM-CKV057 (CNP2B-H12), IM-CKV061 (4-6 CNP4A-E6), IM-CKV062 (4-4 CNP4A-E4), IM-CKV063 (CAP4A-E7), IM-CKV064 (CAP4A-E5), IM-CKV065 (CAP5A-F6), IM-CKV066 (CAP1A-B5), and IM-CKV067 (CAP1A-B3)

Example 1: Materials and Methods

Isolation of Human Neutralizing Antibodies.

The anti-CHIKV human monoclonal antibody (mAb) C9 was isolated by EBV transformation of B cells from a CHIKV infected and recovered individual identified during a 2007 outbreak of CHIKV in Northern Italy. CHIKV pseudovirus neutralization was used as the primary screening assay for the selection of B cell clones and heavy and light chains were subsequently sequenced from the clones. Separately, a Fab fragment (E8) was isolated from a phage display library constructed from multiple CHIKV infected and recovered individuals from the 2005-6 epidemic on La Réunion. A virus-like particle (VLP) binding assay, using VLPs produced from CHIKV capsid and E3/E2/E1 envelope (env) glycoprotein expression was used as the primary screen for panning phage, followed by use of the CHIKV pseudovirus (HIV-backbone based, without CHIKV capsid) neutralization assay for downstream characterization. Subsequently, the antibody heavy and light chains for C9 and E8 were sequenced and cloned into human full length IgG vectors for protein production and evaluation.

Potent In Vitro Neutralization

Figure 7:
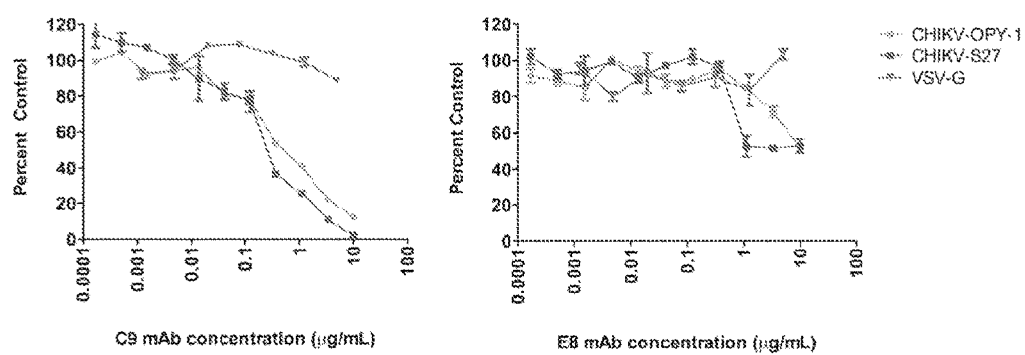
FIG. 7. Human mAbs C9 and E8 neutralization. Neutralization of pseudovirus bearing CHIKV LR2006-OPY-1 strain (orange lines) CHIKV S27 strain (green lines) and VSV-G control (magenta lines) envelope by (A) C9 or (B) E8 mAbs. Antibody concentration is shown in the x-axis. The results are expressed as the percentage of no antibody control and represent mean of triplicate wells, and is representative of three experiments.

C9 and E8 were tested in neutralization assays performed in HEK 293T cells using CHIKV pseudoviruses bearing an envelope from the prototypical West African, Asian, and East/Central/South African (ECSA) CHIKV strain, S27. The C9 and E8 IgG antibodies neutralized CHIKV pseudoviruses at approximately 0.1 μg/ml and 1.0 μg/ml ($IC_{50}$) respectively (FIG. 1). Pseudoparticles produced using envelopes derived from the LR2006 OPY-1 strain from the La Réunion outbreak were similarly sensitive to neutralization, with $IC_{50}$ values of 0.4 μg/ml and 10 μg/ml for C9 and E8 respectively (FIG. 7). Similar neutralization was observed regardless of the cell type used. Neutralization was specific to CHIKV with no detectable cross-reactivity to pseudoviruses expressing other alphavirus envelopes—RRV, SFV and SINV, as well as VSV-G (FIG. 1). The mAb also neutralized CHIKV envelopes with a naturally occurring mutation at a critical site near the fusion loop in E1 (A226V) that is associated with increased CHIKV infectivity for, and transmission by, the mosquito vector, *Aedes albopictus* (C9, $IC_{50}$ 0.1 μg/ml; E8, $IC_{50}$ 1.0 μg/ml) (FIG. 1).

When tested in a replication competent CHIKV plaque reduction neutralization test (PRNT) using the S27 strain, C9 exhibited a PRNT80 value of approximately 0.3 μg/ml. A comparable level of neutralization was also observed with the LR2006 OPY-1 strain. In contrast to the weak neutralization observed with the CHIKV pseudovirus assay (FIG. 1), E8 failed to neutralize replication competent CHIKV, even at concentrations up to 20 μg/ml. Similarly, little to no inhibition by E8 was noted utilizing vesicular stomatitis virus-based pseudotypes (rather than HIV-based) or in a cell-cell fusion assay, while C9 maintained similar neutralizing and inhibitory activity. Based on these findings, C9 can be categorized as a potent CHIKV neutralizing antibody, while E8 is a non-neutralizing, or weakly neutralizing, antibody of live virus.

Binding Properties of Anti-CHIKV Human mAbs

Figure 2:
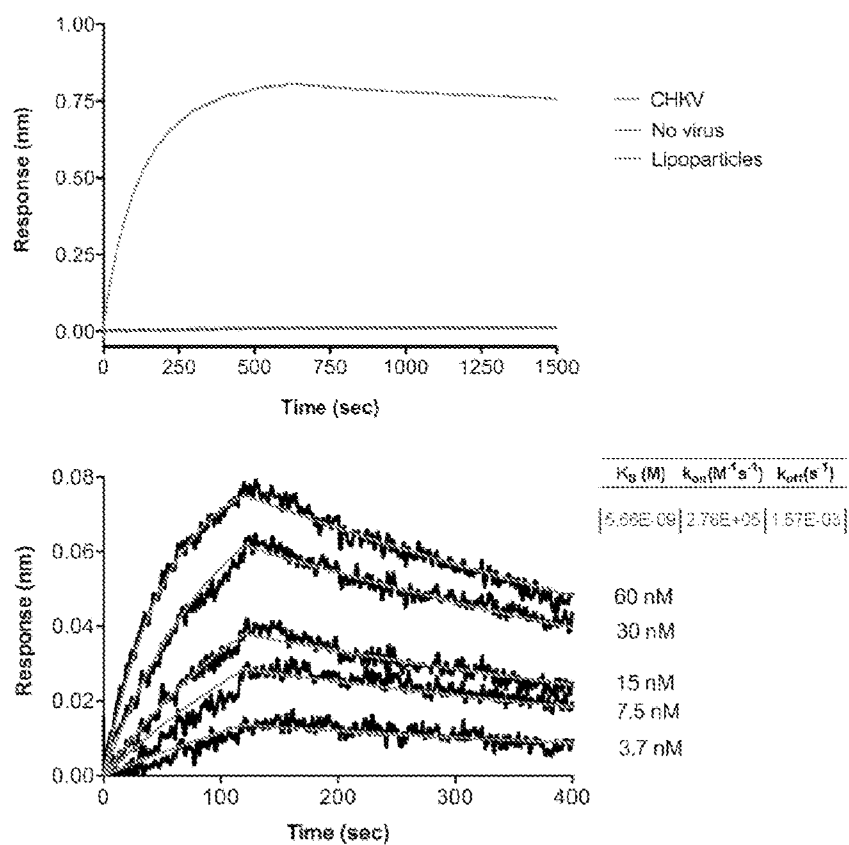
FIG. 2. Kinetic analysis of binding to intact CHIKV virus like particles. (A) Summary of antibody/antigen interactions. Binding of anti-CHIKV antibody C9 to intact CHIKV VLPs was detected using the FoteBio OctetRed biosensor. C9 mAb (120 nM) binding to CHIKV VLPs, control MLV-based VLPs or a non-particle surface is used to show binding specificity of mAb to intact CHIKV VLP. (B) C9 dose response curve for binding intact CHIKV VLPs. Raw data curves for antibody associating and dissociating from captured CHIKV VLPs are shown in black and fitted curves are shown in red. Data were fitted to a 1:1 binding model to determine association rate ($k_{on}$) and dissociation rate ($k_{off}$), and equilibrium binding affinity ($K_D$) was calculated. C9 binds CHIKV VLPs with 5.66 nM affinity.

In order to determine how strongly each mAb interacts with the native virion, intact CHIKV VLPs were captured onto the surface of ForteBio Octet RED biosensor tips and antibody binding to the immobilized particles was measured using BioLayer Interferometry. Whereas C9 bound to VLPs with an apparent affinity of 5.66 nM (FIGS. 2A & B), E8 failed to recognize CHIKV envelope protein on intact VLPs, consistent with its inability to neutralize live CHIKV. To investigate the structural requirements for E8 binding, CHIKV VLPs were disrupted using 0.1% dodecylmaltoside/0.1% CHAPS detergent and solubilized env was captured onto biosensor tips. In contrast to intact VLPs, E8 was found to bind to solubilized env, suggesting that the E8 epitope may be occluded in the native E1/E2 conformation on virions. C9 and E8 antibodies recognized envelope derived from CHIKV VLPs under semi-native conditions (protein run in SDS gels without reducing agent), suggesting that both C9 and E8 recognize conformation specific epitopes that are dependent on disulfide bonds.

mAb Epitope Mapping Using Shotgun Mutagenesis

In order to identify the specific binding site of C9 and E8, the mAbs were screened against a comprehensive CHIKV mutation library in which nearly every residue within the E2, 6K, and E1 envelope subunits (encompassing 910 amino-acid residues with a 98.5% coverage) were individually mutated to an alanine (alanines were mutated to serines). Each clone was expressed in HEK-293T cells and assessed for C9 and E8 antibody binding using immunofluorescence staining Mean fluorescence was determined by high-throughput flow cytometry and antibody reactivity to each mutant and was calculated relative to reactivity to wild-type (WT) CHIKV env. Clones were identified as critical for binding if they had low reactivity to C9 or E8 but high reactivity to other CHIKV E2-specific control antibodies (CKV061, E26D9.02 and rabbit polyclonal antibody, described in materials and methods). This counter-screen strategy facilitates the exclusion of env mutants that are globally or locally misfolded or that have an expression defect [28].

Six amino acids clustered within the E2 Domain A were identified as critical for E8 binding. Residues E2-Y69, E2-F84, E2-V113, E2-G114, E2-T116, and E2-D117, when mutated to alanine, all reacted at less than 20% of WT reactivity when screened with E8, but had high reactivity to 3 comparison antibodies (CKV061, E26D9.02 and rabbit polyclonal antibody), suggesting that the mutant envelope proteins are expressed and properly folded (FIG. 3A). The E8 epitope appears to be partially occluded when visualized on the native trimer structure (FIG. 3B), which likely accounts for the poor neutralization exhibited by E8.

C9 Antibody Binding Residue Mapped to the Acid-Sensitive Region of E2

Figure 4:
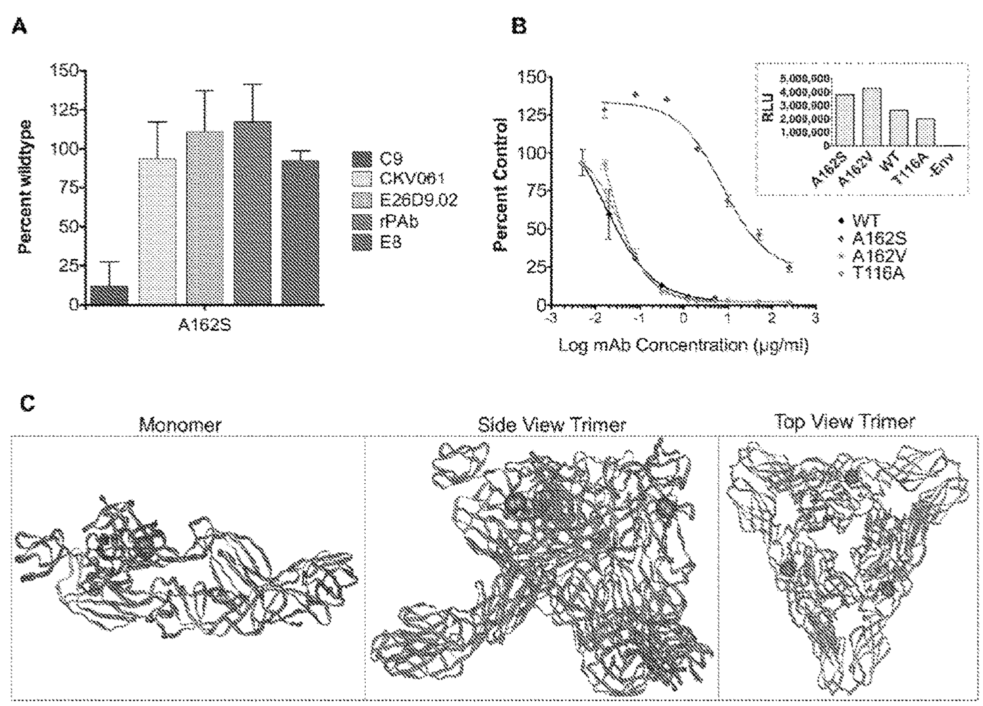
FIG. 4. Critical residues and predicted C9 binding site. (A) HEK-293 cells expressing mutant CHIKV envelope proteins were immunostained with C9 antibody. Clones with reactivity<20% relative to wild-type CHIKV env were identified as critical for C9 binding. Mutation of residue A162 in E2 to serine significantly reduced C9 binding (green bar) but did not affect binding of E8 (red bar) or other control antibodies (gray bars). Residues are numbered according to E2 in the PDB entry #3N41 (Voss J E, Vaney M C, Duquerroy S, Vonrhein C, Girard-Blanc C, et al. (2010) Glycoprotein organization of Chikungunya virus particles revealed by X-ray crystallography. Nature 468: 709-712). (B) A162S and A162V pseudoviruses were tested for C9 inhibitory potency and A162S showed a 490-fold C9 resistance compared to WT CHIKV pseudoviruses. No difference was observed in neutralization of A162V or T116A expressing pseudoviruses. The infectivity of the mutants compared to WT was tested (inset graph), indicating that the mutants did not hinder CHIKV env folding or function. Average raw luminescence units are shown for each construct and an env-minus negative control. (C) The critical residue A162 (shown in green) was visualized on the CHIKV env crystal structure. The E1, E2, and E3 env protein subunits in the monomer (PDB Entry #3N41) are depicted in yellow, red, and blue, respectively and the fusion loop is shown in silver (left panel). In the side-view and top-down trimeric representations (center and right panels, PDB entry #2XFC), E3 is not in the structure. In the side view trimeric representation (center panel), the viral membrane is positioned at the bottom of the figure.
Figure 5:
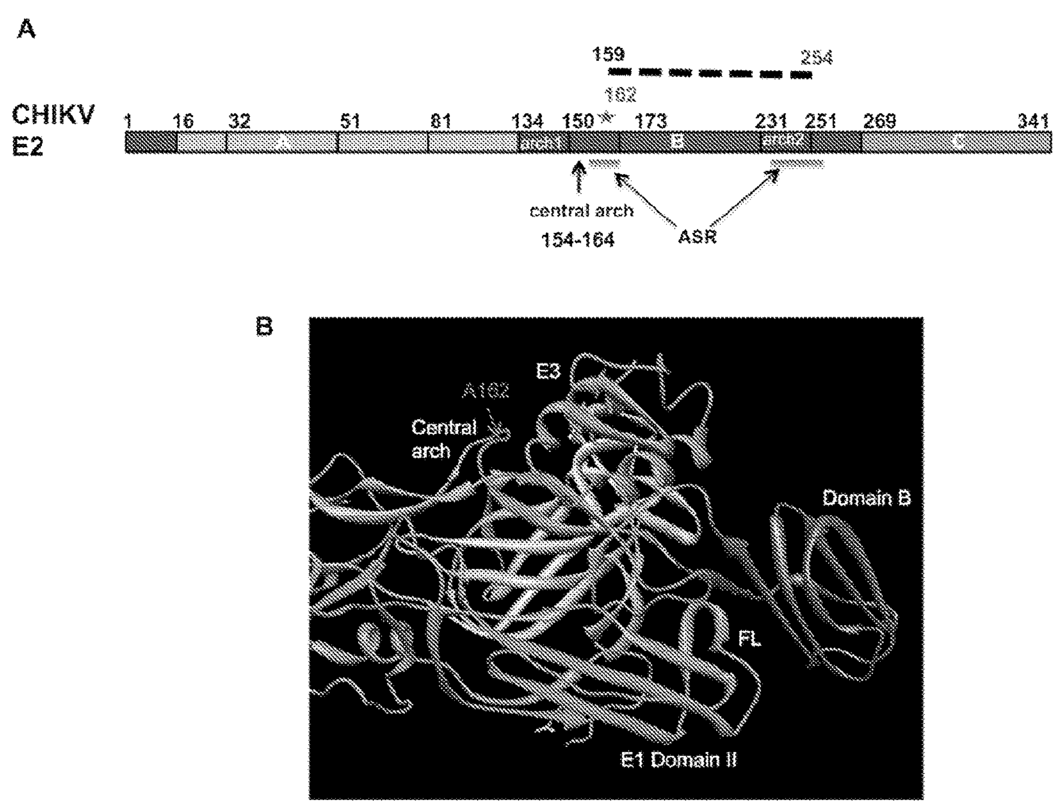
FIG. 5: ASR with E2-A162 represented on CHIKV envelope. (A) Linear diagram of E2 colored to represent the various segments forming the individual domains observed in the crystal structure (Voss J E, Vaney M C, Duquerroy S, Vonrhein C, Girard-Blanc C, et al. (2010) Glycoprotein organization of Chikungunya virus particles revealed by X-ray crystallography. Nature 468: 709-712). The figure was adapted from (Voss J E, Vaney M C, Duquerroy S, Vonrhein C, Girard-Blanc C, et al. (2010) Glycoprotein organization of Chikungunya virus particles revealed by X-ray crystallography. Nature 468: 709-712). The red bars indicate the ASR and the green star shows the position of the predicted C9 contact residue A162. The ASR and domain B of E2 (black dashed line) is the region in E2 that becomes disorganized following pH trigger. (B) Crystal structure model showing the intersection of ASR in the pocket between E1, E2 and E3. C9 contact residue E2-A162 is shown by a green arrow. FL—fusion loop.

Similar epitope mapping studies using Shotgun Mutagenesis alanine scanning identified residue E2-A162, located in the β-connector region between domains A and B of CHIKV E2, as a critical residue required for C9 recognition (FIG. 4). The E2-A162 residue is solvent exposed and is predicted to be easily accessible when CHIKV Env is in the native trimer conformation. The E2-A162 residue is in the acid-sensitive region (ASR) sandwiched in a critical pocket between CHIKV E1, E2 and E3 as determined by the CHIKV envelope crystal structure (FIG. 5). Interestingly, the ASR, along with the E2 domain B, was also recently described for alphaviruses as being unstructured following acid pH triggering. In our study we found that residue E2-A162, when mutated to serine, reacted at 12% of WT reactivity against C9 but reacted at greater than 70% of WT reactivity against other anti-CHIKV antibodies, strongly suggesting that the E2-A162S mutant is properly folded and involved in the C9/envelope binding interaction (FIG. 4A). We also measured the binding of C9 to mutant Envs bearing substitutions for other residues in the region of amino acids 159-171. We detected reduced binding of C9 to E2-A164S, E2-E165A, E2-E166A and E2-I167A; however reduced binding was also observed with other anti-CHIKV antibodies indicating the possibility that the mutations cause aberrant envelope folding that disrupts the CHIKV spike conformation (data not shown). Therefore, it is possible that residues E2-164, -165, -166 and -167 are not directly involved in C9 binding.

Using pseudovirions, no virus entry defects were observed with E2-A162S, further indicating that the mutant envelopes are properly folded. To confirm the importance of this residue in C9 binding, infection experiments were conducted with wild type and mutant pseudovirions. E2-A162S pseudovirions were inefficiently neutralized by C9, with a 490-fold increase in the C9 $IC_{50}$, demonstrating that this residue is required for potent C9 inhibition (FIG. 4). In contrast, wild type E2 and E2-A162V, a naturally occurring variant), remained fully sensitive to C9.

Figure 6:
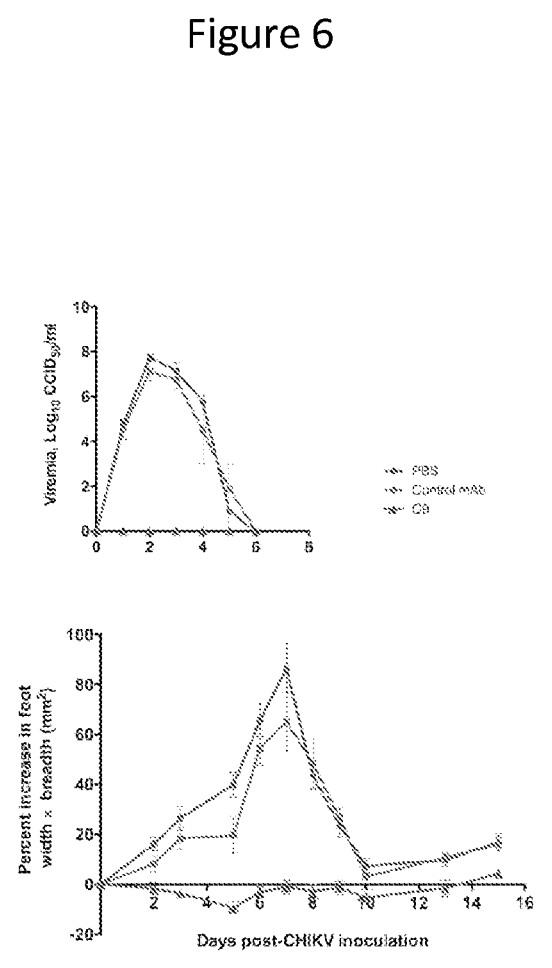

C9 mAb Inhibited Viremia and Arthritis in an Adult Wild-Type Mouse Model of CHIKV Disease To assess the potential protective activity of mAb C9 in vivo, we used an adult wild-type mouse model of CHIKV disease. Mice received an intra-peritoneal injection of purified C9 IgG (0.5 mg/mouse) the day before being infected with the Reunion Island isolate of CHIKV (LR2006-OPY-1). A control monoclonal antibody that did not recognize CHIKV (produced in the same fashion as C9) and PBS were used as negative controls. Infected mice were monitored for viremia and foot swelling as described previously. In both control groups, CHIKV infection resulted in a 5-6 day viremia and increased foot swelling similar to that described previously in control animals. In contrast, mice injected with C9 IgG showed no detectable viremia or foot swelling (FIG. 6). These results demonstrate that the C9 antibody completely protected animals against viremia and arthritic disease.

This example describes the isolation and characterization of two human monoclonal antibodies, C9 and E8, from CHIKV infected and recovered individuals. We previously developed a CHIKV pseudovirus assay that we found amenable in our current study to high-throughput screening and selection of B-cell clones expressing CHIKV neutralizing antibodies. C9 neutralizes both CHIKV pseudoviruses and replication-competent viruses with high potency. The E8 monoclonal antibody shows less dramatic neutralization of pseudovirus and does not neutralize live virus at the highest concentration tested (20 μg/ml). This suggests that although the CHIKV antibody selection could be carried out using the high-throughput pseudovirus assays, the live virus-PRNT assay is the more reliable confirmatory assay for CHIKV neutralization.

We also report the development of a novel, comprehensive CHIKV envelope site-directed mutation library in which nearly all of the 910 residues of the full-length E1 E2 CHIKV envelope protein were individually mutated to alanine in order to identify critical amino acids that are recognized by human mAbs C9 and E8. E8 recognized 6 spatially proximal residues (Y69, F84, V113, G114, T116A and D117) in E2 domain A, however the non-neutralizing nature of the E8 antibody may denote that the residues are not easily accessible on the native CHIKV envelope (exposed on live virus), and indeed the epitope appears to be partially occluded when visualized on the native trimer crystal structure. The site-directed mutagenesis mapping studies, confirmed by neutralization escape mutant studies, revealed that E2-A162 is a critical residue required for C9 mAb recognition. Interestingly, based on the crystal structure of the CHIKV envelope, the E2-A162 residue is located in the ASR of E2 that encompasses amino acids 159-171 and 231-258 (FIG. 5). The ASR in E2, along with domain B, is a highly conserved functional region among alphaviruses and is involved in the conformational rearrangements triggered by acid pH that lead to the exposure of the fusion loop in E1 and finally results in membrane fusion. It is possible that neutralizing antibodies such as C9 that bind to the ASR region could fully or partially prevent the disordering and movement of E2 from E1 following pH triggering, thereby reducing fusion efficiency and CHIKV entry. Residues within the ASR have previously been reported to be critical for efficient particle formation and stability, highlighting the delicate conformational balance that this region brings to E2. Thus, it is may be that additional residues forming the C9 epitope are too critical for efficient E2 expression for detection in the epitope mapping assays.

While the C9 antibody was isolated from individuals infected with the more recent strain similar to LR2006-OPY-1, the critical E2-A162 residue is highly conserved among different CHIKV strains and is represented in the 1950's West African isolates 37997 and S27 as well as in LR2006 OPY-1. However, a previous study described a strain (Ag41855) isolated from Uganda during a 1982 outbreak that has a valine at the E2-162 position, although E2-V162 was not identified as a residue that is expressed in conjunction with A226V, and the Ag41855 isolate did not have enhanced replicative abilities in *Aedes albopictus* mosquitos. Mutating E2-A162 to valine did not result in a loss of C9 potency, suggesting C9 should be active against most currently circulating strains of CHIKV and other strains that arise in the future with that particular amino-acid. The fact that E2 proteins bearing the aliphatic, hydrophobic amino-acids alanine or valine did not prevent C9 neutralization, while E2 with a polar serine residue at position 162 escaped neutralization, demonstrates that the serine substitution disrupts the C9 epitope, whereas the valine substitution does not.

Neutralizing antibodies have been shown to be critical for recovery from alphavirus infections and a number of neutralizing epitopes have been characterized, albeit only a handful for CHIKV. Of particular note, antibody R6/R13 is specific to SINV and has been previously documented to have an escape mutant at position K159N (equivalent to CHIKV residue E2-T160) in the ASR of SINV E2 glycoprotein. However, to our knowledge, C9 is the first CHIKV specific neutralizing antibody to target a critical ASR residue flanking the domain B of CHIKV E2 glycoprotein. The isolation and characterization of additional CHIKV mAbs should offer insight into the proportion of antibodies elicited against this particular epitope in CHIKV infected individuals and the timing at which they appear. For example, an elegant study recently described that a predominant proportion of the very early response to CHIKV envelope are IgG3 antibodies directed against the N-terminal sequence in E2 (E2EP3).

In order to elucidate whether strong in vitro C9 neutralization would translate to protection in vivo, we used the C9 antibody in an adult wild-type mouse model of CHIKV disease. In contrast to control mice, mice pretreated with C9 antibody had no detectable CHIKV viremia or arthritis. This report demonstrates protection against viremia and rheumatic disease in vivo by a neutralizing antibody that targets the acid-sensitive region in CHIKV E2.

Although passive antibodies cannot be utilized for protection from CHIKV on a regular basis, one can envisage a scenario where a potent antibody like C9 can be manufactured and used for protecting highly susceptible individuals such as pregnant women, infants and older individuals during a CHIKV epidemic. We believe the isolation and epitope characterization of C9 antibody and demonstration of its potent neutralization in vitro and in vivo are invaluable to future studies aimed at envelope mapping studies and identification of neutralization epitopes specific to CHIKV. Furthermore, we hypothesize that the epitope recognized by the C9 antibody is an important region to target for antibody-based intervention in future anti-CHIKV strategies.

Materials and Methods:

Generation of C9 and E8 IgG Mammalian Expression Constructs:

CHIKV MAb C9 variable chains were sequenced by MC Labs (South San Francisco, Calif.). For mammalian expression, C9 variable heavy (VH) and light (VL) chain cDNAs were synthesized by Genscript (Piscataway, N.J.). The closest human germline signal sequences (ss), VH5 5a and VKIII A27, were used to ensure efficient processing and secretion. SS-VH cassettes were cloned into a pCAGGS mammalian expression vector as EcoRI-NheI fragments, upstream of the human IgG1 heavy chain constant region. SS-VL cassettes were cloned as EcoRI-BsiWI fragments upstream of the human kappa light chain constant region. CHIKV FAb CAP101A.E8 variable heavy and light chain cDNAs bearing human IL-2 signal sequences were synthesized by Genscript. IL-2ss-VH and IL-2ss-VL cassettes were cloned as MfeI-NheI and MfeI-BsiWI fragments upstream of their respective constant regions, as described above.

CHIKV Wild-Type Envelope Pseudovirion Production:

CHIKV envelope (E3/E2/E1) in a pCAGGS vector was used for pseudoparticle preparation as described previously. Lentiviral pseudotypes were produced essentially as described (Simmons et al., 2004) by using 10 μg of luciferase, (pNL-luc, based on pNL4-3-R-E-) [Connor, 1995] and 30 μg of plasmid-encoding viral envelope. Virions were concentrated by ultracentrifuge concentration at 28,000 rpm in a SW28 rotor (Beckman) through a 20% sucrose cushion for 1.5 h at 4° C. The pellets were resuspended overnight in HBSS at 4° C. VSV-G and alphavirus envelopes expressing the RRV, SFV and SINV were used as controls for pseudovirion neutralization assay.

CHIKV Wild-Type Pseudovirus Neutralization Assay:

HEK 293T cells were plated at $2\times10^4$ cells/well in DMEM (HyClone) containing additives and incubated at 37 C in 5% $CO_2$ overnight. The following day, serial dilutions of antibody and virus pre-incubated for 45 min were added to the HEK 293T cells. A spin infection was performed at 2000 rpm for 60 min and cells incubated for an additional 3 hours at 37° C. The antibody-virus mix was removed by aspiration and replaced with 100 μl of pre-warmed fresh media. The cells were incubated for 48 hrs before samples were recovered for measurement of luciferase activity in the cell lysates as per manufacturers protocol (Promega).

CHIK Wild-Type Virus Production, Plaque Assay and 80% PRNT Assay:

CHIKV was obtained from ATCC (ATCC # vr-64), from a strain originally isolated in 1953 from the serum of a patient in East Africa and expanded in suckling mice. Replication competent CHIKV was grown in Vero cells. Vero cells $0.5\times10^5$ were plated in a 6-well (Costar) plate overnight. Serial dilution of the virus stock (250 μl) was incubated with cells for 1 hr at 37° C. One hour after incubation an overlay of 4% agarose (Life Technologies) in DMEM supplemented with 2% FBS was added to cells and incubated at 37° C. for 72 hrs. Subsequently, wells were fixed with 4% formaldehyde and stained with 0.1% crystal violet in methanol: ethanol. Plaques were counted against a white background.

Vero cells ($0.5\times10^5$) were plated in a 6-well (Costar) plate overnight. Serially diluted monoclonal antibodies were mixed with CHIK live virus diluted to 400 PFU/ml and pre-incubated for an hour at 37° C. Following this 250 μl of the antibody-virus mixture was added to the confluent Vero cell monolayer for an additional hour. Subsequently, the virus was removed and an overlay of 4% agarose in DMEM supplemented with 2% FBS was added and cells were incubated at 37° C. for 72 hrs. The plaques were stained and counted as described above. The PRNT titer is calculated as the reciprocal of the serum dilution where 80% reduction in the number of plaques compared to the negative control in the presence of media and no mAbs.

Isolation of Anti-CHIKV Antibody From EBV Transformed B Cells:

The PBMCs for EBV transformed B cell isolation were obtained from two CHIKV infected and recovered individuals. B cells were isolated using the Miltenyi MACS Switched Memory B cell Isolation kit (130-093-617) according to the manufacturers protocol. The cells were plated at 30 cells per well in 96 U-well plates. PBMC from unrelated donors were treated with Mitomycin C and used as feeder cells at $5\times10^4$ cells per well. The cells were cultured in RPMI supplemented with 7% FBS, 1000 IU/L IL-2 (Roche) and 2.5 μg/ml R848 peptide (InvivoGen). Filtered B95-8 EBV supernatants (diluted 1 in 3) were added per well and incubated for one week before being replaced with fresh media. EBV transformed B cell supernatants expressing CHIKV specific antibodies were screened for CHIKV pseudotype neutralization potential. The cells from positive wells were clonally isolated by limiting dilution followed by expansion and cloning.

Immune Phage Antibody Library Construction:

An immune FAb phage display library was constructed from peripheral blood donated by three CHIKV-infected individuals. All three individuals were infected in Réunion Island, France, during the 2006 outbreak. Peripheral blood samples were drawn 2-3 years after infection and serum was analyzed for the presence of neutralizing antibodies using CHIKV pseudotypes. Total RNA was prepared using Tri-Reagent (Sigma) with standard protocols. RNA was converted to cDNA using Super Script First-Strand Synthesis System for RT-PCR (Invitrogen) following the manufacturer's instructions. Construction of the library was performed by GenScript (Piscataway, N.J.) as previously described. The final library was transformed into *E. coli* TG1 cells (Invitrogen) using electroporation, and the quality of the library was assessed by sequence analysis of 100 randomly picked clones.

Characterization of Antibody Binding Kinetics Using Biosensor:

All biosensor studies were performed in PBS buffer supplemented with 1 mg/ml BSA (PBS-B) at 25° C. using a ForteBio Octet Red biosensor system (ForteBio). CHIKV VLPs were loaded onto streptavidin (SA) biosensor tips using a monoclonal mouse antibody against CHIKV (CKV033, a gift of Mike Diamond), which was captured using a biotinylated goat anti-mouse polyclonal antibody (GAM Fc, Southern Biotech). Briefly, GAM Fc was diluted to 5 μg/ml in PBS-B and bound to SA sensor tips for 10 minutes. Following a brief rinse in PBS-B, CKV033 (5 μg/ml in PBS-B) was captured for 10 minutes. After another brief rinse, CHIKV VLPs diluted to 10 μg/ml were loaded for 45 minutes followed by a 10 minute stabilization. C9 was prepared as a threefold serial dilution (starting at 18 μg/ml) plus buffer blanks Antibody association was measured for 10 minutes followed by 20 minutes dissociation in buffer. Non-specific binding was assessed using sensor tips without VLPs as well as using sensor tips loaded with retroviral pseudotypes (Lipoparticles) containing only endogenous cell surface receptors (no viral Env). Data analysis was performed using Octet Data Analysis v6.4 (ForteBio). Binding kinetics were analyzed using a standard 1:1 binding model.

To measure antibody binding to solubilized CHIKV envelope protein, CHIKV VLPs were incubated in 0.1% dodecylmaltoside/0.1% CHAPS buffer for 15 minutes and envelope protein was captured onto biosensor tips using the CKV033 mouse monoclonal antibody as described above. E8 and C9 antibodies were prepared as threefold serial dilutions starting at 10 μg/ml. Antibody association was measured for 10 min followed by 20 min dissociation in buffer.

Shotgun Mutagenesis Mapping Studies:

A CHIKV Env expression construct (S27 strain) with a C-terminal V5 tag was subjected to high-throughput alanine scanning mutagenesis to generate a comprehensive mutation library. Primers were designed to mutate each residue within the E2, 6K, and E1 regions of Env to alanine, while alanine codons were mutated to serine. In total, 910 CHIKV Env mutants were generated (98.5% coverage), sequence confirmed, and arrayed into 384-well plates. Each Env mutant was transfected into HEK-293T cells and allowed to express for 22 hrs. Cells were stained for 1 h with hmAbs C9 (0.42 μg/ml), E8 (2 μg/ml), CKV061 (0.75 ug/ml, isolated from phage display library in identical manner to E8), E26D9.02 (0.5 μg/ml, a gift from Dendritics), and rabbit polyclonal antibody (1:2000 dilution, a gift from IBT Bioservices) diluted in 10% NGS (Sigma). MAbs were detected using 3.75 μg/ml AlexaFluor488-conjugated secondary antibody in 10% NGS (Jackson ImmunoResearch Laboratories) for 1 h. Mean cellular fluorescence was detected using the Intellicyt high throughput flow cytometer (HTFC, Intellicyt). Antibody reactivities against each mutant Env clone were calculated relative to wild-type env protein reactivity by subtracting the signal from mock-transfected controls and normalizing to the signal from wild-type Env-transfected controls. Mutations within critical clones were identified as critical to the hMAb epitope if they did not support reactivity of the test human mAb, but did support reactivity of the other CHIKV antibodies. This counter-screen strategy facilitates the exclusion of env mutants that are misfolded or have an expression defect. Critical amino acids required for antibody binding were visualized on the CHIKV env crystal structure (monomer PDB ID #3N41 and trimer PDB ID #2XFV, 22) to obtain 3D epitope maps.

CHIKV Mouse Model; Arthritis and Viremia Monitoring:

Female C57BL/6 mice (6-12 weeks) were inoculated with CHIKV as described previously. Briefly, mice were inoculated with CHIKV $\{10^4 \log_{10}$ 50% cell culture infectivity dose ($CCID_{50}$)$\}$ in 40 μl RPMI 1640 (supplemented with 2% fetal calf serum) by shallow subcutaneous injection into the top, towards the lateral side, of each hind foot in the metatarsal region, injecting toward the ankle. Arthritis was monitored by measuring the height and width of the metatarsal area of the hind feet using digital calipers. The data is presented as a group average of the percentage increase in foot height×width for each foot compared with the same foot on day 0.

Viremias were measured by collecting 40 μl of blood from a tail vein into 0.8-ml MiniCollect serum separation tubes (Greiner Bio-One GmbH, Kremsmunster, Austria). The tubes were spun at 7,000 rpm for 2.5 min on a bench-top microcentrifuge. Serum was collected and viral titers were determined as described previously and expressed as $CCID_{50}$ per ml.

Phage Display Selection of CHIKV-Specific FAbs Using CHIKV VLPs:

VCSM13 helper phage (Stratagene) was used to rescue the immune phage library overnight. Purified CHIKV VLPs (S27 strain) were coated directly onto a microtiter plate (Nunc) overnight at 4° C. using 1 μg of protein per well in 0.1 M sodium bicarbonate buffer, pH 8.6. The wells were washed with phosphate-buffered saline (PBS) and the virus was pH-triggered using HEPES-buffered saline (HBS) at pH 5.8 for 10 minutes and subsequently neutralized by washing once with HBS at pH 8.0 for 1 minute. The wells were washed with PBS and blocked with 4% (w/v) non-fat dry milk in PBS (4% PBSM) for one hour. Prior to panning the CHIKV VLP coated wells, phage diluted in 4% PBSM were panned against blank wells, without antigen, to remove nonspecifically binding phage. The depleted phage were added to the CHIKV VLP coated wells and incubated for 2 hours at 37° C. During the first round of panning, wells were washed 3 times with PBS containing 0.01% (v/v) Tween 20 (Sigma), then once with PBS, followed by elution at 37° C. with 10 mg/ml Trypsin (Sigma) and infection of TG1 cells. After log-phase growth, cells were infected with VCSM13 helper phage for rescue and additional selection following the same strategy as the first panning round. Three total rounds of selection were carried out with increased stringency for the second (5 washes) and third rounds (10 washes). TG1 cells were infected with the output from the third round and colonies were obtained for screening.

Isolation and Screening of Phage Display FAb Clones:

Individual FAb phage clones were cultured (2×YT, 1% glucose, 50 μg/ml Carbenicillin) from single colonies isolated in the third round of panning and induced in the absence of glucose with 1 mM Isopropylβ-D-1-thiogalactopyranoside (IPTG). Culture supernatants containing FAb phage clones were screened for CHIKV-specific binding in a phage enzyme-linked immunosorbent assay (ELISA). Purified CHIKV VLPs were directly coated onto a microtiter plate overnight at 4° C. using 0.25 μg of protein per well in 0.1 M sodium bicarbonate buffer, pH 8.6. The wells were washed with PBS and virus was treated using HBS at pH 5.8 for 10 minutes. VLPs were neutralized by washing once with HBS at pH 8.0 for 1 minute and the wells were subsequently washed with PBS and blocked with 4% PBSM for one hour. Phage clone supernatants in 2% PBSM were added to each well and the plate was incubated for one hour at 37° C. with gentle agitation. The phage solution was discarded and the plate washed 3 times with PBS/0.01% Tween 20. To detect bound phage, a 1:5,000 dilution of horseradish peroxidase (HRP)-conjugated anti-M13 MAb (GE Healthcare) in 4% PBSM was added to the wells and incubated at 25° C. for thirty minutes with gentle agitation. The plate was washed 3 times with PBS/0.01% Tween 20 and developed according to the manufacturer's instructions (Super Signal West Pico, Pierce). Negative controls for each clone tested included a buffer blank (no antigen, clone phages added) and a negative antigen (non-specific antigen, clone phages added). Clones that had a signal to noise greater than 4 were identified as specific for CHIKV, and DNA was isolated using the QIAprep miniprep kit (Qiagen). Phagemid DNA was sequenced with primers specific for both the light and heavy chains, and analysis of the CDR regions was performed using the programs IMGTBquest and VBase2 FAb Analysis. Families of clones were identified by grouping according to the heavy chain CDR3. Those clones which had unique CDR groupings were identified as unique, including the CAP101A.E8 (E8) clone, and the sequences were used for conversion to IgG format.

Example 2: Materials and Methods

Immune Phage Antibody Library Construction

A Fab phage display library was constructed from peripheral blood donated by three CHIKV-infected individuals, as described (Selvarajah S, Sexton N R, Kahle K M, Fong R H, Mattia K A, Gardner J, Lu K, Liss N M, Salvador B, Tucker D F, Barnes T, Mabila M, Zhou X, Rossini G, Rucker J B, Sanders D A, Suhrbier A, Sambri V, Michault A, Muench M O, Doranz B J, Simmons G. 2013. A neutralizing monoclonal antibody targeting the Acid-sensitive region in chikungunya virus e2 protects from disease. PLoS Negl Trop Dis 7:e2423). All three individuals were infected in Réunion Island, France, during the 2006 outbreak. Briefly, peripheral blood samples were drawn three to four years after infection and serum was analyzed for the presence of neutralizing antibodies using HIV reporter viruses pseudotyped with CHIKV E2/E1. Total RNA was prepared using TRI-Reagent (Sigma-Aldrich, St. Louis, Mo.). RNA was converted to cDNA using Super Script First-Strand Synthesis System for RT-PCR (Invitrogen, Carlsbad, Calif.) following the manufacturer's instructions. Construction of the phage library was performed by GenScript (Piscataway, N.J.).

Screening of Isolated Fab Clones

Individual Fab peripreps were prepared from single colonies by inducing with 1 mM IPTG at 28° C. overnight and lysing cells in PBS by freeze-thaw, and then screening for CHIKV-specific binding in a Fab enzyme-linked immunosorbent assay (ELISA). Purified VLPs were directly coated on a microtiter plate overnight at 4° C. using 0.25 ug of protein per well in 0.1 M sodium bicarbonate buffer, pH 8.6. The wells were washed with PBS and blocked with 4% PBSM for one hour. Fabs in 4% PBSM were added to each well, and the plate was incubated for one hour at 37° C. with gentle agitation. The Fab solution was discarded and the plate was washed 3 times with PBS+0.01% Tween 20. To detect bound Fab, a 1:5,000 dilution of anti-Human Fd horseradish peroxidase (HRP) (Southern Biotech, Birmingham, Ala.) in 4% PBSM was added to the wells and incubated at room temperature for 30 minutes with gentle agitation. The plate was washed 3 times with PBS-1-0.01% Tween 20 and developed according to the manufacturer's instructions (Super Signal West Pico, Thermo Scientific, Waltham, Mass.). Negative controls included a buffer blank (no antigen) and a nonspecific antigen.

Construction and Transient Production of Recombinant IgG Antibodies

Candidate Fabs were converted to human IgG1 format for production in HEK-293T cells. Briefly, phage-derived Fab variable domains were subcloned downstream of the human IL-2 signal sequence and upstream of either human IgG-1 heavy (γ1) or light (κ1) constant domains in a mammalian expression vector. Heavy and light chain constructs were co-transfected into HEK-293T cells at a ratio of 1:3 by calcium phosphate co-precipitation. Secreted IgG was purified from the culture media 48-72 hours post-transfection by Protein-A chromatography, followed by concentration and buffer exchange against PBS. Quantification of the purified IgG was performed by BCA assay (Thermo Scientific, Waltham, Mass.).

Purification of CHIKV VLPs

CHIKV VLPs were produced by transfecting HEK-293T cells with an expression plasmid encoding a codon-optimized chimera between o'nyong nyong (ONNV) capsid (Igbo Ora strain, residues 1-260) and CHIKV E3/E2/E1 (S27 strain, residues 262-1248). After production for 2-3 days, supernatant was filtered through a 0.22 μm filter (Corning #430517). 37.5% PEG 8000 (Sigma #P4463) was added 1:4 to the filtered supernatant and incubated overnight at 4° C. to precipitate VLPs. The mixture was spun for 30 minutes at 7,000 rpm at 4° C. using a JLA-8.100 rotor. Post-spin, the media was aspirated and 25 ml HBS (150 mM NaCl, pH 8.0) was added to resuspend precipitated VLPs. The resuspension was added to a large Beckman Ultra-Clear centrifuge tube (25×89 mm, Beckman) and a 10 ml 20% sucrose cushion was added (10 mM HEPES, 100 mM NaCl, 1 mM EDTA, pH 8.0). The sample was spun for 3 hours at 31,000 rpm at 4° C. using a SW-32 rotor. Post-spin, the suspension and sucrose layer were aspirated and the pellet was resuspended in 10 ml HBS. The resuspension was added to a small Beckman Ultra-Clear centrifuge tube (14×89, Beckman) and a 1 ml 20% sucrose cushion was added. The sample was spun for 3 hours at 31,000 rpm at 4° C. using an SW-41 rotor. Post-spin, the suspension and sucrose layer were aspirated and the purified viral pellet was gently resuspended in 200 ul HBS. The sample was stored for 1 hour at 4° C. and thereafter at −80° C.

Construction of CHIKV E2/E1 Mutation Library

A CHIKV envelope expression construct (S27 strain, Uniprot Reference #Q8JUX5) encoding a C-terminal V5 epitope tag was subjected to high-throughput alanine scanning mutagenesis to generate a comprehensive mutation library. Primers were designed to mutate each residue within the E2, 6K, and E1 regions of envelope (residues Y326 to H1248) to alanine, while alanine codons were mutated to serine. In a few cases, other amino acid substitutions were generated instead of alanine. In total, 910 CHIKV envelope mutants were generated (98.5% coverage), sequence confirmed, and arrayed into 384-well plates, one mutant per well.

Immunofluorescence Assay

The CHIKV mutation library, arrayed in 384-well microplates, was transfected into HEK-293T cells and allowed to express for 22 hours. For MAbs CNP2B-H12, IM-CKV061, IM-CKV062 and CAP1A-B3, cells were fixed in 4% paraformaldehyde (Electron Microscopy Sciences, Hatfield, Pa.) in PBS plus calcium and magnesium (PBS++). Cells were stained with purified MAbs CNP2B-H12 (0.25 ug/ml), IM-CKV061 (0.75 ug/ml), IM-CKV062 (0.5 ug/ml), CAP5A-F6 (1.0 ug/ml), CAP1A-B5 (1.0 ug/ml), CAP1A-B3 (1.0 ug/ml) and purified Fab CAP4A-E7 (2.5 ug/ml) diluted in 10% normal goat serum (NGS) (Sigma-Aldrich, St. Louis, Mo.). For CAP4A-E7 it was necessary to employ a Fab for epitope mapping since the high affinity MAb bound too tightly to identify individual point mutants that ablated MAb binding. Primary MAb concentrations were determined using an independent immunofluorescence titration curve against wild-type CHIKV E2/E1 to ensure that signals were within the linear range of detection. MAbs were detected using 3.75 ug/ml AlexaFluor488-conjugated secondary antibody (Jackson ImmunoResearch Laboratories, Westgrove, Pa.) in 10% NGS. Cells were washed twice with PBS−/− and resuspended in Cellstripper (Cellgro, Manassas, Va.) with 0.1% BSA (Sigma-Aldrich, St. Louis, Mo.). Mean cellular fluorescence was detected using the Intellicyt high throughput flow cytometer (HTFC, Intellicyt, Albuquerque, N. Mex.). MAb reactivities against each mutant E2/E1 clone were calculated relative to wild-type E2/E1 protein reactivity by subtracting the signal from mock-transfected controls and normalizing to the signal from wild-type E2/E1-transfected controls.

Epitope Identification

Mutated residues within critical clones were identified as critical to the MAb epitope if they did not support reactivity of the test MAb but did support reactivity of a reference CHIKV MAb and additional CHIKV MAbs. This counter-screen strategy facilitates the exclusion of E2/E1 mutants that are locally misfolded or that have an expression defect (Paes C, Ingalls J, Kampani K, Sulli C, Kakkar E, Murray M, Kotelnikov V, Greene T A, Rucker J B, Doranz B J. 2009. Atomic-level mapping of antibody epitopes on a GPCR. J Am Chem Soc 131:6952-6954). For CAP5A-F6, epitope residues were further refined based on surface accessibility in the structure. Residues constituting the MAb epitope were visualized on heterodimeric and trimeric CHIKV envelope crystal structures (E2/E1 heterodimer PDB ID #3N41 and E2/E1 trimer PDB ID #2XFC).

Characterization of MAb Binding Kinetics Using Biosensor

All biosensor studies were performed in PBS buffer supplemented with 1 mg/ml BSA (PBS-B) at 25° C. using a ForteBio Octet Red biosensor system (Pall-ForteBio, Inc., Menlo Park, Calif.). Purified CHIKV VLPs were loaded onto amine reactive biosensor tips (AR2G) using a human MAb against CHIKV (E26D9, Dendritics, Lyon, France). Briefly, amine reactive sensor tips were activated by EDC/sulfo-NHS (20 mM and 10 mM, respectively) for 5 minutes. E26D9 at 25 ug/ml in 10 mM sodium acetate pH 5.5 was then immobilized on tips with a 10 minute incubation. Following a 5 minute deactivation in 1M ethanolamine and a 10 minute stabilization in PBS-B, CHIKV VLPs diluted to 20 ug/ml were loaded for 45 minutes followed by another 10 minute stabilization. CAP4A-E7 was prepared as a two-fold serial dilution (starting at 20 ug/ml) plus buffer blanks Non-specific binding was assessed using sensor tips without VLPs. Data analysis was performed using Octet Data Analysis v6.4 (ForteBio). Binding kinetics were analyzed using a standard 1:1 binding model.

VLP ELISAs 96-well white, flat bottom microtiter plates were coated with retroviral VLPs ('Lipoparticles') containing CHIKV E2/E1 at 5.0 ug/well or CHIKV VLPs at 0.5 ug/ml and incubated overnight at 4° C. For CNP2B-H12, IM-CKV061, IM-CKV062, CAP4A-E7, and CAP1A-B3, particles were fixed in 4% paraformaldehyde. The plates were blocked with 3% BSA (Sigma) for 15 minutes at room temperature. For the comparative retroviral/CHIKV VLP ELISA, primary MAb was diluted to a previously optimized concentration (see Immunofluorescence assay methodology), added to the plates, and allowed to incubate for 1 hour at room temperature (22° C.). For the temperature-dependent ELISA, primary MAb was diluted to 2 ug/ml in blocking buffer, added to the plates, and allowed to incubate for 1 hour at room temperature (22° C.), 37° C., or 45° C. The plates were washed 3 times with PBS−/−, and then HRP-conjugated rabbit anti-human secondary diluted at 1:5,000 in blocking buffer was added for 1 hour at room temperature. The plates were washed 3 times with PBS−/− and reactivity was detected using SuperSignal West Pico Chemiluminescent Substrate (ThermoScientific, Waltham, Mass.).

CHIKV Pseudovirus Neutralization Assay

Lentiviral reporter viruses pseudotyped with CHIKV E2/E1 were produced essentially as described (Salvador B, Zhou Y, Michault A, Muench M O, Simmons G. 2009. Characterization of Chikungunya pseudotyped viruses: Identification of refractory cell lines and demonstration of cellular tropism differences mediated by mutations in E1 glycoprotein. Virology 393:33-41; Simmons G, Reeves J D, Rennekamp A J, Amberg S M, Piefer A J, Bates P. 2004. Characterization of severe acute respiratory syndrome-associated coronavirus (SARS-CoV) spike glycoprotein-mediated viral entry. Proc Natl Acad Sci USA 101:4240-4245) by co-transfecting CHIKV E2/E1 plasmid with plasmids encoding HIV core (gag-pol, based on (Naldini L, Blomer U, Gallay P, Ory D, Mulligan R, Gage F H, Verma I M, Trono D. 1996. In vivo gene delivery and stable transduction of nondividing cells by a lentiviral vector. Science 272:263-267) and luciferase (pNL-luc, based on pNL4-3-R-E- (Connor R I, Chen B K, Choe S, Landau N R. 1995. Vpr is required for efficient replication of human immunodeficiency virus type-1 in mononuclear phagocytes. Virology 206:935-944)). Cells were incubated at 37° C. in 5% $CO_2$ to allow for transfection and pseudovirus production. 24 to 72 hours post-transfection, supernatants were harvested, filtered, and stored at −80° C. Target HEK-293T cells were plated at $0.4\times10^6$ cells/well in DMEM (ThermoScientific, Waltham, Mass.) containing additives and incubated at 37° C. in 5% $CO_2$ overnight. The following day, serial dilutions of MAb and virus pre-incubated for 45 min were added to the HEK-293T cells. A spinoculation was performed at 2000 rpm for 60 min at 20° C., and cells were then incubated at 37° C. At 24 hours post-infection, 100 ul of fresh media was added to each well. Infected target cells were lysed 48 hours post-infection and lysates were assayed for luciferase activity (Promega, Madison, Wis.).

CHIKV Wild-Type Virus Production and Plaque Assay

Replication competent CHIKV S27 (ATCC #vr-64), a strain originally isolated in 1953 from a patient in East Africa, was grown in Vero cells. Vero cells ($0.5\times10^5$) were plated in a E-well (Costar) plate and grown overnight. Serially diluted MAbs were mixed with S27 diluted to 400 PFU/ml and pre-incubated for an hour at 37° C. Following this, 250 μl of the MAb-virus mixture was added to the confluent Vero cell monolayer for an additional hour. Subsequently, the virus was removed and an overlay of 4% agarose in DMEM supplemented with 2% FBS was added and cells were incubated at 37° C. for 72 hrs. The plaques were stained and counted as described (Selvarajah S, Sexton N R, Kahle K M, Fong R H, Mattia K A, Gardner J, Lu K, Liss N M, Salvador B, Tucker D F, Barnes T, Mabila M, Zhou X, Rossini G, Rucker J B, Sanders D A, Suhrbier A, Sambri V, Michault A, Muench M O, Doranz B J, Simmons G. 2013. A neutralizing monoclonal antibody targeting the Acid-sensitive region in chikungunya virus e2 protects from disease. PLoS Negl Trop Dis 7:e2423). The PRNT titer is calculated as the MAb concentration that resulted in a 50% reduction in the number of plaques compared to the negative control in the presence of media and no MAbs.

CHIKV Neonate Mouse Model

The efficacy of MAbs to protect against lethal CHIKV infection was evaluated in a 9-day old murine model as previously described (Selvarajah S, Sexton N R, Kahle K M, Fong R H, Mattia K A, Gardner J, Lu K, Liss N M, Salvador B, Tucker D F, Barnes T, Mabila M, Zhou X, Rossini G, Rucker J B, Sanders D A, Suhrbier A, Sambri V, Michault A, Muench M O, Doranz B J, Simmons G. 2013. A neutralizing monoclonal antibody targeting the Acid-sensitive region in chikungunya virus e2 protects from disease. PLoS Negl Trop Dis 7:e2423). All animal experiments were performed with approval of the Institutional Animal Care and Use Committee at ISIS Services, LLC (San Carlos, Calif.). C57BL/6J mice were purchased from Jackson Laboratories (Sacramento, Calif.). Breeder pairs were housed under specific-pathogen free conditions in micro-isolator cages (Innovive Inc., San Diego, Calif.). Mice were checked daily, and the date when litters were first observed was considered day 0. On day 9, litters with their mothers were transferred to static disposable cages (Innovive, Inc., San Diego, Calif.) and transferred into a BSL-3 facility for infection and treatment. Neonatal C57BL/6J mice were infected with $5\times10^5$ PFU of CHIKV (S27 strain, expanded and titered in Vero cells) intradermally in the ventral thorax. Mice were intraperitoneally injected with test MAb or control human IgG/mouse in 0.2 ml phosphate-buffered saline (PBS) immediately prior to CHIKV infection. Purified IgG from human serum was used as a control (Sigma-Aldrich, St. Louis, Mo.). Mice were then observed daily for up to 20 days. Results were analyzed using Kaplan-Meier survival curves using GraphPad Prism 5 software (GraphPad, Calif.).

CHIKV Arthritis Mouse Model

The ability of MAbs to protect against the arthralgia induced by CHIKV infection was evaluated in an arthritic mouse model as previously described (Gardner J, Anraku I, Le T T, Larcher T, Major L, Rogues P, Schroder W A, Higgs S, Suhrbier A. 2010. Chikungunya virus arthritis in adult wild-type mice. J Virol 84:8021-8032). Briefly, female C57BL/6 mice (8 weeks old) were inoculated with CHIKV (LR2006-OPY-1 strain; $10^4$ $\log_{10}$ 50% cell culture infectivity dose (CCID50)) or heat inactivated CHIKV in 20 μl DMEM (supplemented with 2% fetal calf serum). Mice were inoculated by a shallow subcutaneous injection into the top, towards the lateral side, of each hind foot in the metatarsal region, injecting toward the ankle Mice (n=5 mice per group) were injected with 100 ug purified MAb CAP4A-E7 by intraperitoneal route on day 0 with CHIKV. Mice not treated with CAP4A-E7 did not get receive I.P. injections. In order to avoid stimulating non-specific immune responses that may interfere with CHIKV infection of adult mice (Gardner J, Anraku I, Le T T, Larcher T, Major L, Rogues P, Schroder W A, Higgs S, Suhrbier A. 2010. Chikungunya virus arthritis in adult wild-type mice. J Virol 84:8021-8032), CAP4A-E7 with endotoxin levels below 10 EU/mg were used. Arthritis was monitored by measuring the height and width of the metatarsal area of the both hind feet using digital calipers (Gardner J, Anraku I, Le T T, Larcher T, Major L, Rogues P, Schroder W A, Higgs S, Suhrbier A. 2010. Chikungunya virus arthritis in adult wild-type mice. J Virol 84:8021-8032).

Isolation of Human CHIKV MAbs by Phage Display

Figure 8:
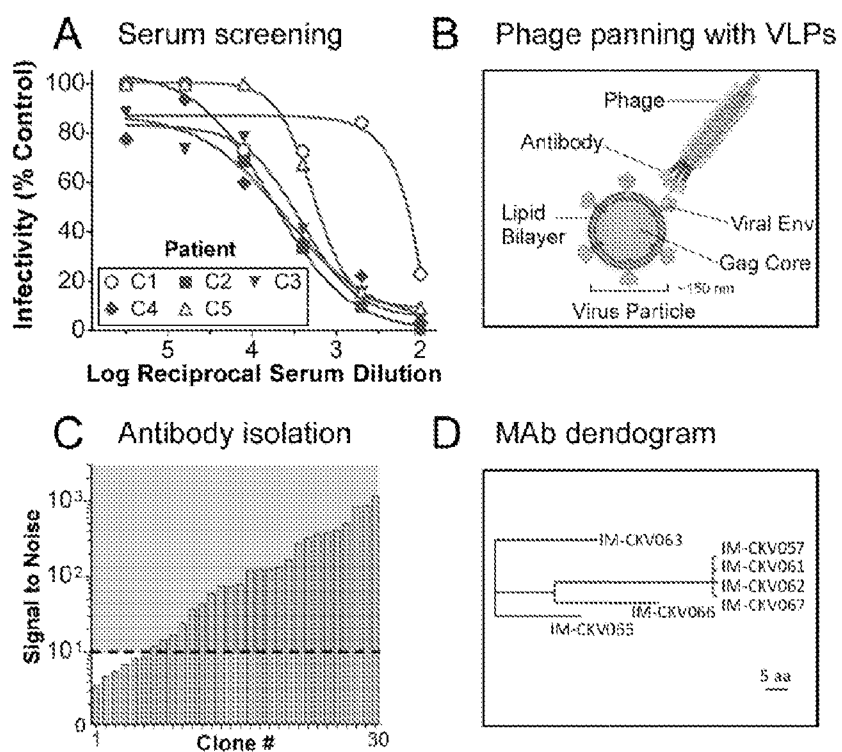
FIG. 8. Isolation of patient-derived MAbs against CHIKV, using viral particles containing native E2/E1. (A) Serum samples from patients (C1-C5) infected with CHIKV during the 2006 outbreak in La Réunion were screened by neutralization assays. All neutralization results are shown normalized to the maximum (uninhibited) infection achieved after background subtraction with a non-infected control. An immune phage Fab library was created from the B-cells of the most highly reactive patient samples (red symbols, patients C2, C3 and C4) (B) The phage Fab library created from the B-cells of CHIKV infected patients was used to pan against retroviral (Gag core) and CHIKV (alphavirus capsid core) virus-like particles (VLPs) displaying the native form of CHIKV E2/E1. (C) Fabs isolated from phage display were further tested for E2/E1 target selectivity in ELISA assays using CHIKV VLPs for specificity and DENV-1 virions (Mattia K, Puffer B A, Williams K L, Gonzalez R, Murray M, Sluzas E, Pagano D, Ajith S, Bower M, Berdougo E, Harris E, Doranz B J. 2011. Dengue reporter virus particles for measuring neutralizing antibodies against each of the four dengue serotypes. PLoS One 6:e27252) as a negative control. The majority of the clones tested displayed at least 10:1 selectivity for the E2/E1 target. (D) ClustalW alignment of VH chain amino acid sequences followed by Neighbor-Joining analysis was used to generate the unrooted dendrogram (MacVector 10). Tree distances represent the number of residue differences between sequences (scale-bar 5 residues). IM-CKV061, CAP1A-B3, IM-CKV062, and CNP2B-H12 have identical heavy chains but different light chains.

To better understand the types of antibodies that are elicited in response to natural human infection with CHIKV, we isolated MAbs from infected patients. Serum samples collected two to three years post-infection were screened from individuals who were infected during the 2006 CHIKV outbreak in La Réunion. Virus neutralization assays were used to identify samples containing highly neutralizing antibodies (FIG. 8A), and B-cells from the most reactive patients were used to construct a Fab library for phage display. The phage library was panned using virus-like particles (VLPs) with retroviral cores (from murine leukemia virus Gag) that present CHIKV envelope proteins E2 and E1 (FIG. 8B), or using CHIKV VLPs (based on native alphavirus capsid) that are structurally equivalent to native CHIKV virus. Two different VLP types and slightly different panning protocols were used to maximize the ability to isolate diverse MAbs. A number of E2/E1-reactive antibodies were derived from both panning strategies and bound to CHIKV E2/E1 with a signal-to-background ratio>10:1 (FIG. 8C). Genes encoding the MAb heavy and light chains were sequenced and cloned into full length human IgG vectors for MAb production and evaluation.

Figure 9:
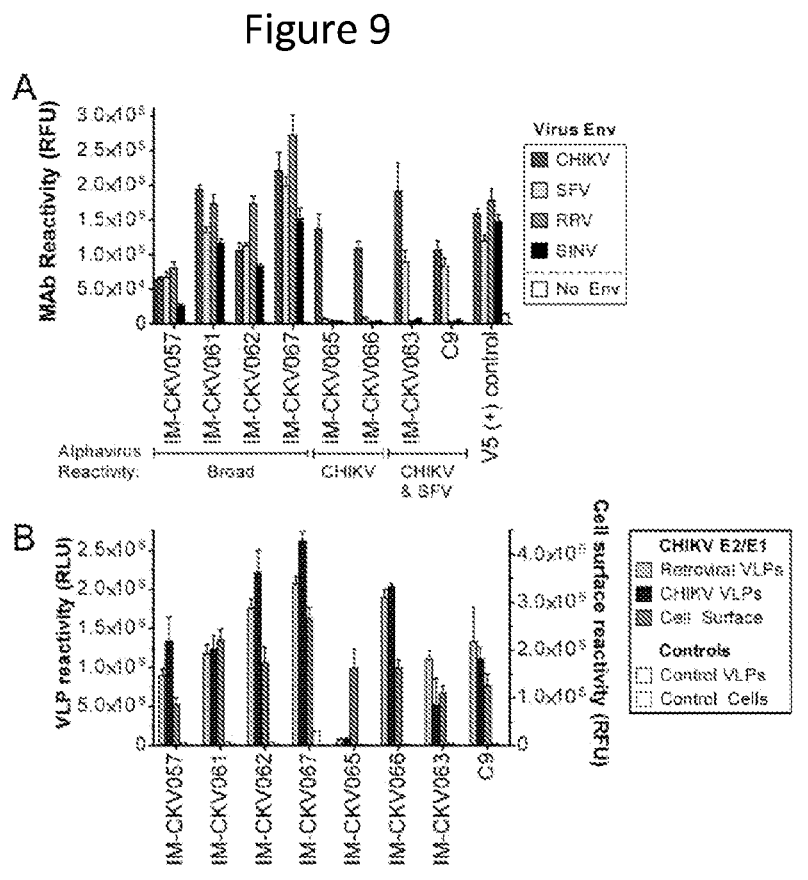

Seven MAbs with unique heavy chain and/or light chain sequences were selected for further characterization (FIG. 8D). Four of the most similar MAbs (CNP2B-H12, IM-CKV061, IM-CKV062 and CAP1A-B3) were derived from panning campaigns using different VLPs (FIG. 20), suggesting that CHIKV VLPs and retroviral VLPs displayed similar conformations of E2/E1. Each MAb was also shown to be immunoreactive against CHIKV E2/E1 expressed on the surface of HEK-293T cells (FIG. 9A). To characterize the cross-reactivity of these MAbs, each was screened against a panel of related alphavirus envelopes (Semliki Forest Virus (SFV), Ross River Virus (RRV) and Sindbis Virus (SINV)) expressed on HEK-293T cells. Four of the seven MAbs were found to be broadly cross-reactive, with high immunoreactivity to all other alphavirus envelopes that were screened, suggesting that their epitopes are broadly conserved among alphavirus envelopes. Two MAbs were selectively reactive with CHIKV E2/E1 alone. Our previously-described neutralizing MAb, C9 (Selvarajah et al.), was selectively reactive with CHIKV and SFV envelopes, as was the newly-isolated MAb CAP4A-E7, suggesting that their epitopes are relatively conserved between these two alphaviruses, at least when expressed in cells.

MAbs were also characterized for their ability to recognize CHIKV E2/E1 epitopes that were presented in different contexts, including retroviral VLPs and CHIKV VLPs that were used for MAb isolation and on HEK-293T cells that were used for alphavirus cross reactivity and epitope mapping studies (FIG. 9B). For all MAbs, with the exception of CAP5A-F6, the pattern of reactivity was similar between VLPs and cells, suggesting that the E2/E1 epitopes for these MAbs are similarly presented on retroviral VLPs, CHIKV VLPs, and the cell surface. CAP5A-F6 demonstrated high reactivity with E2/E1 presented on cells, but low reactivity when presented in the context of retroviral and CHIKV VLPs, despite being isolated using retroviral VLPs. This apparent discrepancy could reflect a difference in epitope presentation on the different surfaces, but could also be due to a number of experimental factors, including the different assays used in cell vs. VLP detection and the very fast off-rate of CAP5A-F6 (see below). Nevertheless, the signal-to-background of CAP5A-F6 binding to VLPs was 4:1 to 8:1, suggesting that this MAb still recognizes E2/E1 on the virus surface.

CAP4A-E7 is a Highly Potent CHIKV Neutralizing Human MAb

To determine if the seven CHIKV-reactive MAbs were capable of inhibiting viral infectivity, they were tested in cellular neutralization assays, initially using reporter viruses pseudotyped with CHIKV E2/E1 (FIG. 10A). The MAbs showed a range of activity, from non-neutralizing (CNP2B-H12, IM-CKV061, IM-CKV062, CAP1A-B5, and CAP1A-B3) to moderately neutralizing (CAP5A-F6, average $IC_{50}$=170 ng/ml) to strongly neutralizing (CAP4A-E7). All MAbs were presented in an identical IgG-1 format, so antibody isotype was not a factor in neutralization ability. MAb CAP4A-E7 potently neutralized CHIKV pseudoviruses with an average $IC_{50}$ of 7.4 ng/ml, comparable to the recently published anti-CHIKV MAb C9 (shown for comparison; $IC_{50}$ of 51 ng/ml) that we demonstrated could inhibit CHIKV in cell culture and animal models of viral pathogenesis (Selvarajah et al.).

All neutralizing MAbs targeted E2/E1 and not other viral components since they did not neutralize reporter virus pseudotyped with vesicular stomatitis virus (VSV) envelope (FIG. 10B). Neutralization by CAP4A-E7 was selective for CHIKV E2/E1; this MAb did not neutralize viruses bearing envelopes of other alphaviruses (SFV, RRV, SINV) (FIG. 10C), despite being moderately cross-reactive with SFV (FIG. 9A). It is possible that its lower level of reactivity with SFV is not sufficient for neutralization (Pierson T C, Xu Q, Nelson S, Oliphant T, Nybakken G E, Fremont D H, Diamond M S. 2007. The stoichiometry of antibody-mediated neutralization and enhancement of West Nile virus infection. Cell host & microbe 1:135-145), or that residues critical for SFV infectivity are not inhibited by CAP4A-E7 binding.

Select MAbs were also tested for antiviral activity using native replication-competent CHIKV viruses. In a plaque reduction neutralization test (PRNT) assay, CAP4A-E7 demonstrated a dose-dependent inhibitory effect on the infectivity of live virus (average $PRNT_{50}$ value of 11 ng/ml), similar in potency to C9 ($PRNT_{50}$ value of 12 ng/ml in the same assays; FIG. 10D). MAb CAP5A-F6 did not neutralize S27 live virus using PRNT assays, but did neutralize CHIKV strain 37997 with a $PRNT_{50}$ value of 81 ng/ml.

Figure 11:
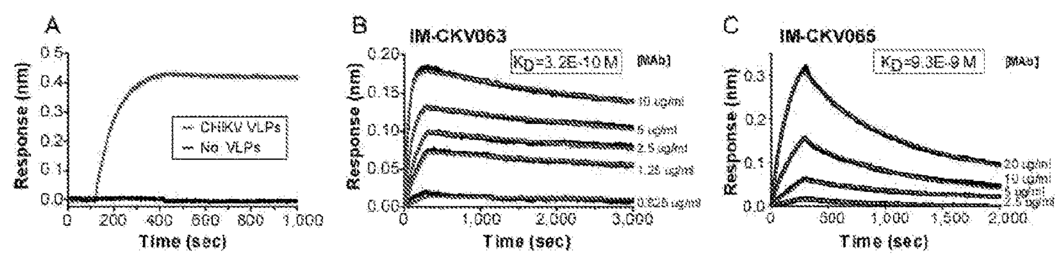
FIG. 11. Kinetic analysis of MAb binding to intact CHIKV virus-like particles. (A) Direct binding of CAP4A-E7 to CHIKV VLPs was detected using a ForteBio OctetRed biosensor, with VLPs immobilized on biosensor tips via the CHIKV E2/E1 capture MAb E26D9 (Dendritics). MAb CAP4A-E7 at 10 ug/ml was applied to the captured VLPs or an unconjugated surface at 100 seconds to monitor MAb association, and dissociation was measured starting at 400 seconds. CAP4A-E7 bound specifically to CHIKV VLPs. (B) Binding kinetics of CAP4A-E7 to CHIKV E2/E1 were assessed by fitting data to a 1:1 binding model to determine rate constants. An apparent binding affinity of 320 pM was calculated. Raw data curves for MAb association and dissociation from captured antigen are shown in black, and fitted curves are in red. (C) Binding kinetics of MAb CAP5A-F6. An apparent binding affinity of 9.3 nM was calculated.

To further characterize the activities of neutralizing MAbs, we used biosensor analyses to assess the kinetics of MAb binding to E2/E1 presented in its native state on the CHIKV virion surface. Non-infectious CHIKV VLPs were immobilized onto biosensor tips and MAb binding was assessed using biolayer interferometry (FIG. 11). CAP4A-E7 showed specific association to immobilized E2/E1, and did not demonstrate non-specific binding in the absence of CHIKV VLPs. Titration experiments revealed CAP4A-E7's strong binding affinity to E2/E1, characterized by rapid association ($k_{on}$=2.9e5 $M^{-1}s^{-1}$), slow dissociation ($k_{off}$=9.4e-5 $s^{-1}$), and strong affinity ($K_D$apparent of 0.32 nM) that is close to the published affinity of MAb C9 ($K_D$apparent of 1.2 nM) (Selvarajah et al.). In contrast, moderately neutralizing MAb CAP5A-F6 had a much weaker affinity ($K_D$apparent 9.3 nM) for S27 CHIKV E2/E1. Although the association rate for this MAb was relatively fast ($k_{on}$=1.6e5 $M^{-1}s^{-1}$), its rapid dissociation ($k_{off}$=1.5e-3 $s^{-1}$) led to a decreased affinity. The fast dissociation of CAP5A-F6 may also explain its relatively weak binding to VLPs under the experimental conditions used for detection (FIG. 9B). Taken together, the distinct binding characteristics of these MAbs may help explain their relative neutralizing potencies.

CAP4A-E7 is Protective in Animal Models of CHIKV Infection

Figure 12:
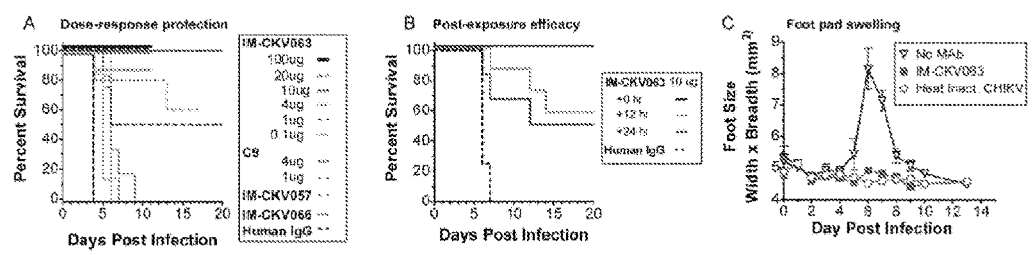
FIG. 12. MAb CAP4A-E7 provides therapeutic protection in mouse models of CHIKV pathogenesis. (A) The ability of MAb CAP4A-E7 to protect neonatal mice from death due to viral infection was determined by injection of MAb concurrent with infection by live CHIKV. CNP2B-H12, CAP1A-B5, and non-specific human IgG (all at 100 ug) were also tested, and MAb C9 was included for comparison. Groups of 4 to 9 mice were used for each condition, depending on the litter size available. (B) MAb CAP4A-E7 was tested for the ability to protect mice after virus exposure. Groups of 6-7 mice were used for each condition. 10 ug of MAb provided complete protection when administered simultaneously with virus, and protected a subgroup of the animals when administered 12 or 24 hours following virus exposure. (C) CAP4A-E7 was tested for protection against foot swelling in an adult mouse model. Mice were injected i.p. with 500 ug of MAb concurrent with injection of CHIKV (LR2006-OPY-1). Foot pad dimensions were measured according to foot width×breadth in the metatarsal region. Five mice were tested in each condition and measurements on both feet were considered to be replicates. Error bars represent standard error of the mean.

We next investigated whether the virus-neutralizing effects of CAP4A-E7 in cell culture would translate to in vivo efficacy in animal models of CHIKV disease. First, we employed a pathogenic neonatal mouse model of CHIKV-induced lethality (Couderc T, Khandoudi N, Grandadam M, Visse C, Gangneux N, Bagot S, Prost J F, Lecuit M. 2009. Prophylaxis and therapy for Chikungunya virus infection. J Infect Dis 200:516-523), which evaluates absolute protection from lethality upon treatment. Here, mice were concurrently inoculated with live virus and test MAbs. Complete survival was observed with 100 ug, 20 ug, and 10 ug doses of CAP4A-E7, and 90% survival with a 4 ug dose ($p \leq 0.05$ for doses of 4 ug and above, relative to IgG control) (FIG. 12A, blue curves). Control mice that received 100 ug (approx 25 mg/kg) of non-neutralizing human IgG succumbed to infection within 4 days. The level of protection afforded by MAb CAP4A-E7 was similar to MAb C9 at doses of 1 ug and 4 ug ($p>0.05$). In contrast, MAbs that were non-neutralizing in cellular assays (CNP2B-H12 and CAP1A-B5) provided little or no protection relative to IgG control even at high doses of 100 ug, and all mice died within 10 days of infection. Importantly, CAP4A-E7 also provided significant protection from lethality when administered post-exposure in a more therapeutically relevant scenario. A 10 ug dosage of CAP4A-E7 was injected 12 or 24 hours after infection and led to survival of at least 50% of mice (FIG. 12B) ($p \leq 0.05$ relative to IgG).

We also assessed CAP4A-E7 in a second in vivo animal model of CHIKV infectivity to assess a different parameter of protection, the ability to protect adult mice from a CHIKV-induced arthritic phenotype. In this model, mice received a 500 ug intra-peritoneal injection of purified CAP4A-E7 (approximately 20-25 mg/kg, a weight-adjusted dose similar to the neonate model) concurrent with administration of CHIKV virus. Infected mice were monitored for foot swelling as described previously (Gardner et al.). Mice injected with CHIKV alone experienced a five to six day foot swelling, as previously seen (Selvarajah et al.; Gardner et al.). In contrast, mice injected with CAP4A-E7 showed no detectable foot swelling at any point during the experiment (FIG. 12C). Taken together, these results demonstrate the ability of CAP4A-E7 to neutralize CHIKV effectively in vivo.

Epitope Mapping of CHIKV MAbs

Figure 13:
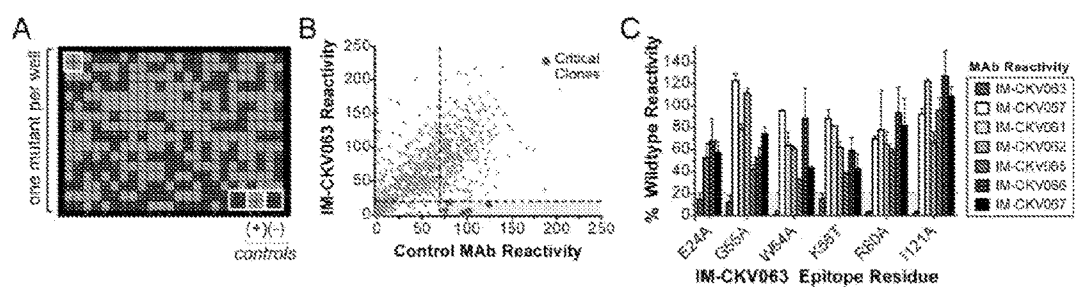
FIG. 13. Critical residues for MAb CAP4A-E7 binding. (A) A shotgun mutagenesis mutation library for CHIKV envelope protein encompassing 910 E2/E1 mutations was constructed where each amino acid was individually mutated to alanine Each well of each mutation array plate contains one mutant with a defined substitution. A representative 384-well plate of reactivity results is shown. Eight positive (wild-type E2/E1) and eight negative (mock-transfected) control wells are included on each plate. (B) Human HEK-293T cells expressing the CHIKV envelope mutation library were tested for immunoreactivity with MAb CAP4A-E7 and measured using the Intellicyt high-throughput flow cytometer. Clones with reactivity<20% relative to wild-type CHIKV E2/E1 yet >70% reactivity for a different CHIKV E2/E1 MAb were initially identified as critical for CAP4A-E7 binding. (C) Mutation of six individual residues reduced CAP4A-E7 binding (red bars) but did not greatly affect binding of other conformation-dependent MAbs (gray bars). Bars represent the mean and range of at least two replicate data points.

To understand the structural basis by which each MAb binds to CHIKV E2/E1, and how neutralizing and non-neutralizing epitopes differ, the residues required for binding of each MAb were next determined. To accomplish this we used comprehensive alanine scanning, where MAb binding was assessed against a 'shotgun mutagenesis' mutation library of CHIKV E2/E1 variants. Nearly every residue of CHIKV E2/E1 was mutated, generating a library of 910 alanine mutants with 98.5% sequence coverage. The entire mutation library was transfected into human HEK-293T cells in a 384-well array format (one clone per well) and assessed for immunoreactivity using high-throughput flow cytometry (FIG. 13A).

Prior to testing MAbs against the entire CHIKV mutation library, the immunoreactivity of each MAb was optimized by testing reactivity with fixed and unfixed cells and by testing a range of MAb concentrations that resulted in good signal-to-background ratios, >5:1. Once optimized, each MAb was screened against the CHIKV mutation library and residues critical for MAb binding were identified as those where E2/E1 mutations resulted in less than 20% reactivity for the MAb of interest (relative to wild-type CHIKV E2/E1), yet greater than 70% wild-type binding by a reference MAb (FIG. 13B). Residues were further validated as critical by comparing their reactivity across a panel of MAbs to verify that the mutation did not globally disrupt the binding of diverse MAbs (FIG. 13C). Using this approach we systematically mapped the detailed epitopes of all seven MAbs (FIG. 20).

Figure 14:
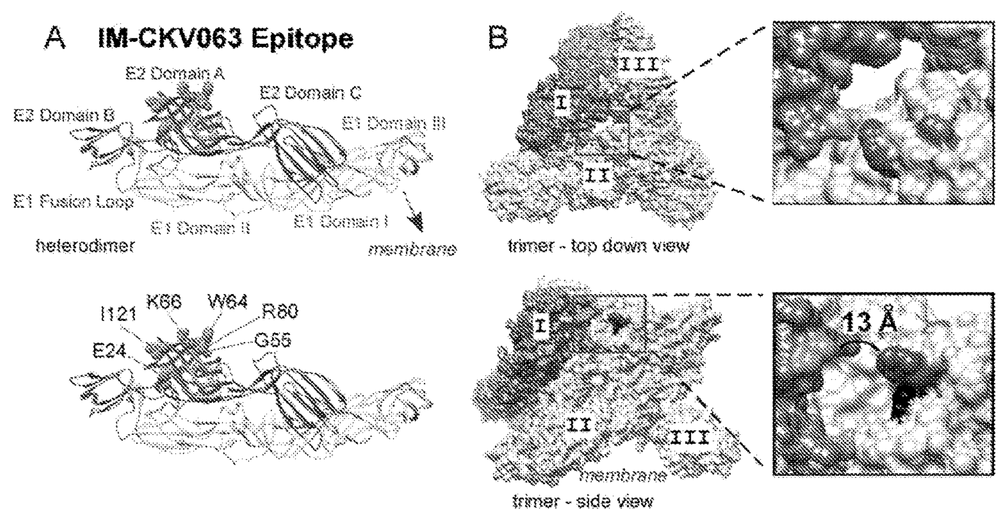
FIG. 14. MAb CAP4A-E7 epitope. The critical residues comprising the epitope for CAP4A-E7 are visualized on the CHIKV envelope crystal structure, showing E2 (red), E1 (yellow) and the fusion loop (cyan). The epitope (green spheres) is depicted on the (A) neutral pH heterodimeric (PDB ID 3N41) and (B) trimeric (PDB ID 2XFC) structures of E2/E1. The CAP4A-E7 epitope appears to span two E2 subunits in the trimer based on structural proximity. A single epitope crossing two E2 subunits (one grey and one blue) is shown with multicolored residues and in the expanded view. Subunit I: E2-E24 (orange) and E2-1121 (green). Subunit II: E2-G55 (yellow), E2-W64 (red), E2-K66 (purple), E2-R80 (black). Residues comprising the other two CAP4A-E7 epitopes on the trimer are indicated in cyan. The distance between residue I121 (shown in green) and residue W64 (shown in red) on two different E2 subunits of the trimer is 13 angstroms.]

For CAP4A-E7, we identified six critical resides whose mutation greatly impaired MAb binding to levels<20% of wild-type E2/E1. These residues all localized on E2 domain A in close proximity to each other (FIG. 14A). Interestingly, visualization of the epitope on the trimeric structure of E2/E1 suggests that these residues form a conformational epitope that lies at the interface of two different E2 subunits (FIG. 14B), constituting a unique inter-subunit epitope. This model suggests that residues E24 and I121 on one E2 subunit form a single MAb binding site together with G55, W64, K66, and R80 on the adjacent E2 subunit within the trimer. The distance between the epitope residues on different heterodimers in the trimer is predicted to be approximately 13 angstroms, consistent with the size of a MAb binding site. This epitope is predicted to be solvent exposed at neutral pH and easily accessible for binding on the native trimeric structure of envelope, which is consistent with the ability of CAP4A-E7 to bind and neutralize infectious virions.

Figure 15:
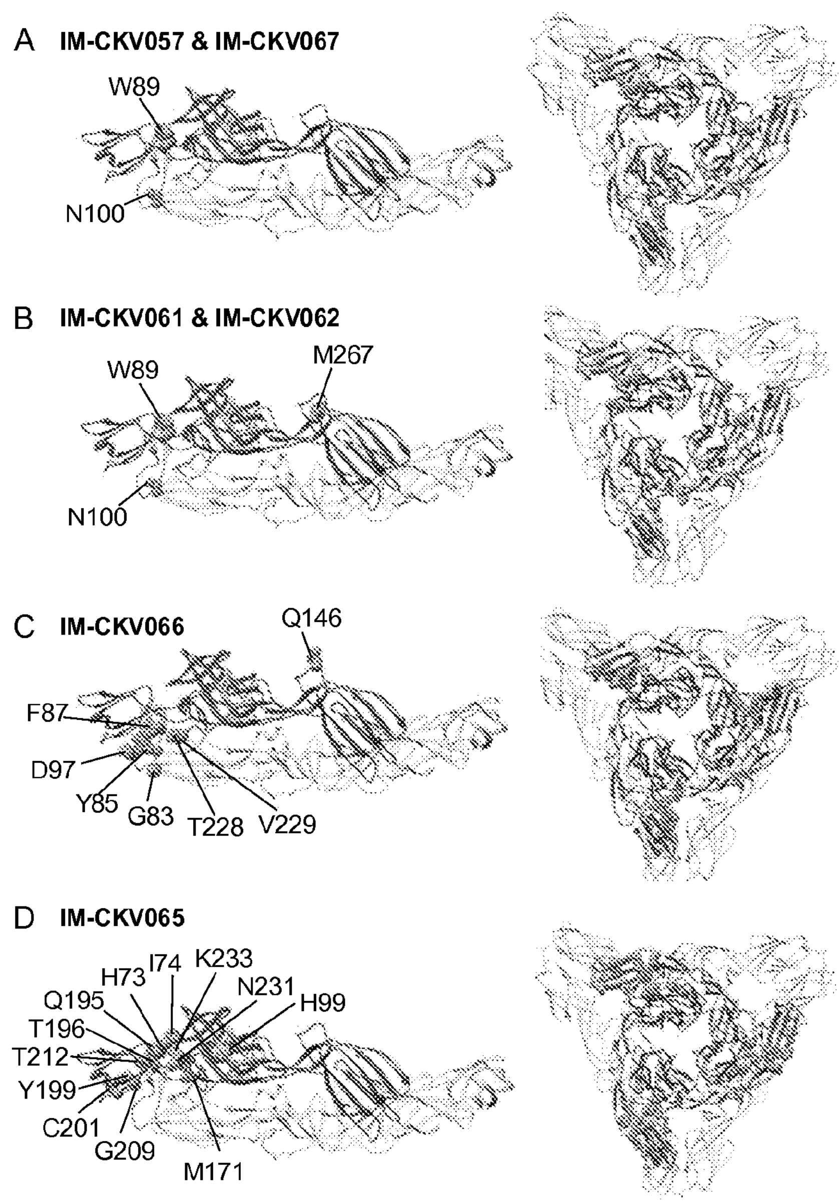
FIG. 15. Epitopes of non-neutralizing and moderately-neutralizing anti-CHIKV MAbs. Critical residues for non-neutralizing CHIKV MAbs (A) CNP2B-H12 and CAP1A-B3, (B) IM-CKV061 and IM-CKV062, (C) CAP1A-B5, (D) and moderately-neutralizing MAb CAP5A-F6 are visualized. All epitopes are visualized on the heterodimeric and top-down trimeric forms of the CHIKV envelope crystal structure (PDB Entry #3N41 and #2XFC). E1 is shown in yellow, E2 is shown in red, the fusion loop is shown in cyan, and epitope residues are shown as green spheres.

We also mapped the epitopes of the non-neutralizing MAbs CNP2B-H12, IM-CKV061, IM-CKV062, CAP1A-B5, and CAP1A-B3, as well as moderately-neutralizing MAb CAP5A-F6. Interestingly, all non-neutralizing MAbs bound to epitopes that encompassed the fusion loop region of E1 (residues 83 through 100). Only a single MAb known to bind the fusion loop of any alphavirus has been previously reported. The fusion loop is highly conserved among alphaviruses, explaining the broad reactivity of the fusion loop MAbs we isolated with other alphavirus envelope proteins (from RRV, SINV, and SFV) (FIG. 9A). Detailed mapping studies showed that MAbs CNP2B-H12, IM-CKV061, IM-CKV062, and CAP1A-B3 bind to identical or overlapping epitopes directly on the fusion loop (FIGS. 15A and 8B), thus also explaining their similarities in cross-reactivity and neutralization. The epitopes of MAbs IM-CKV061 and IM-CKV062 also included the seemingly distant residue E2-M267, which is in fact proximal to fusion loop epitope residues on adjacent heterodimers in the trimeric structure of the protein, thus contributing to an inter-subunit epitope. The epitope for CAP1A-B5 encompassed a different set of highly conserved residues in the fusion loop (G83, Y85, F87 and D97), as well as additional residues on E1 domain II (T228, and V229) and E2 arch 1 (Q146). Together, these residues constitute a discontinuous, inter-subunit epitope in the envelope trimer (FIG. 15C).

The E1 domain II residues are less well conserved than fusion loop residues, so the involvement of these residues in MAb binding may explain the lack of reactivity of CAP1A-B5 with other alphaviruses (FIG. 9A). The moderately-neutralizing MAb CAP5A-F6 was mapped to an area of E2 encompassing domains A and B, and arches 1 and 2 (FIG. 15D). The larger footprint of this MAb may be related to its relatively low affinity, with each individual residue presumably making only minor contributions to the total energetic landscape of the protein-protein interaction.

Figure 16:
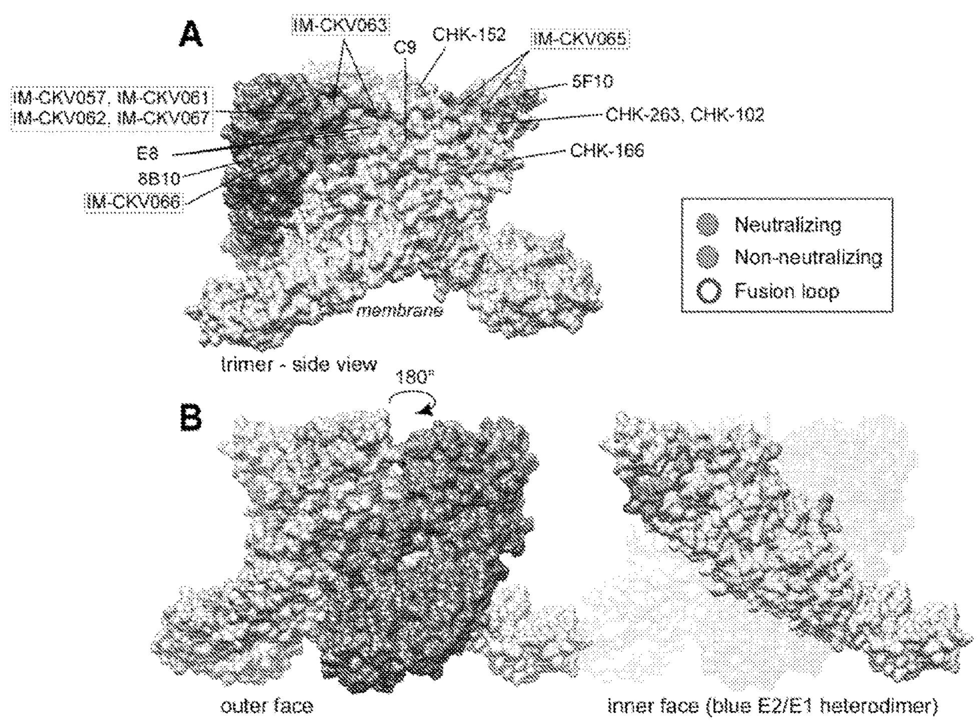
FIG. 16. Epitope mapping reveals highly immunogenic and neutralizing regions of CHIKV E2/E1 (A) The epitopes of non-neutralizing (CNP2B-H12, IM-CKV061 (CNP4A-E6), IM-CKV062 (CNP4A-E4), CAP1A-B5, CAP1A-B3) and neutralizing (CAP4A-E7, CAP5A-F6) MAbs are mapped onto the trimeric crystal structures of E2/E1 (PDB Entry 2XFC, along with additional CHIKV epitopes reported in the literature. MAbs described in this study are boxed. All of the published epitopes map to the membrane-distal domains of E2/E1. Each individual E2/E1 heterodimeric subunit is shown in a different color for clarity. Epitopes on the outer facing surfaces of the trimer (visible in the blue subunit in A) and residues on the top surface of the trimer correlate with MAbs that are neutralizing (residues colored orange), whereas epitopes on the inner regions of the E2/E1 subunits facing the interior of the trimer spike (visible on the dark gray subunit in A) are correlated with MAbs that do not neutralize virus infectivity (colored green). (B) The CHIKV trimer spike is rotated 180 degrees relative to panel A to illustrate that non-neutralizing and fusion loop residues are poorly accessible on the inner face of the virus trimer. A cutaway view with two subunits made transparent reveals non-neutralizing and fusion loop residues that face the interior of the trimer.

Interestingly, when all seven epitopes mapped in this study are visualized together with the eight epitope-mapped human and murine MAbs described in the literature, the epitopes reveal an immunogenic region at the tip of the E2/E1 heterodimer, encompassing E2 domains A and B, the fusion loop, and E1 domain II (FIG. 16A). When the mapped epitopes are visualized on the CHIKV envelope trimer structure, a distinct spatial difference can be observed for the location of neutralizing versus non-neutralizing epitopes. The epitopes for our neutralizing MAbs (CAP4A-E7, CAP5A-F6, and C9) and other neutralizing MAbs described in the literature (CHK-152, CHK-263, CHK-102, CHK-166, and 5F10) are largely found on the accessible outer face and top of the trimer spike (FIG. 16B, orange residues), consistent with their ability to bind infectious virus and prevent infection. In contrast, the epitopes for non-neutralizing MAbs localize to the inner regions of the E2/E1 subunits (i.e. facing the interior of the trimer spike and not readily accessible) (FIG. 16B, green residues). Poor accessibility of these epitopes on the native infectious virion likely explains the lack of MAb neutralizing activity. Cumulatively, these results suggest that the membrane-distal domains of E2/E1 are the most highly immunogenic region of the protein, and that epitopes exposed on the top-most and outer surfaces of the trimer face are neutralizing whereas epitopes facing the interior of the trimer are not.

Fusion Loop Epitope Residues are Poorly Exposed on Native Virions

Figure 17:
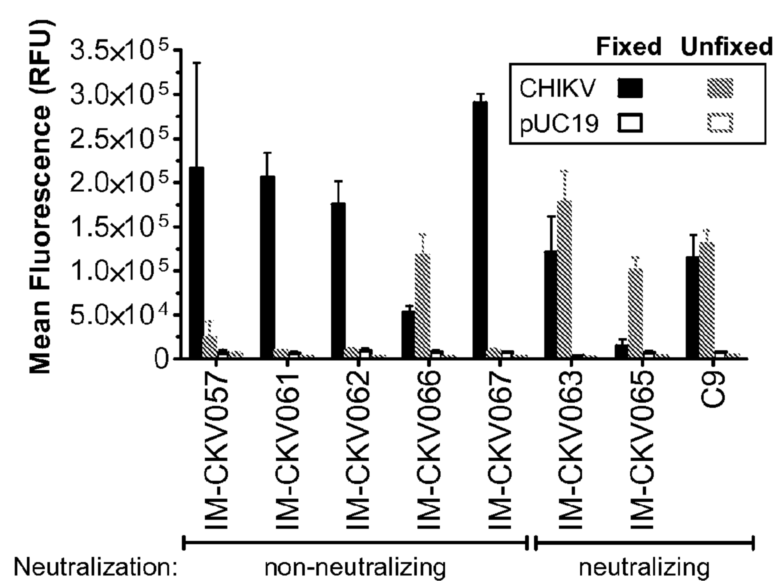
FIG. 17. CHIKV MAb reactivity is influenced by the fixation state of cells expressing E2/E1. CHIKV MAbs were tested for immunoreactivity on HEK-293T cells expressing CHIKV E2/E1 or a vector control (pUC19). Cells were either fixed with 4% paraformaldehyde for 5 min or left unfixed prior to the addition of primary MAb. Immunoreactivity was determined by flow cytometry. Bars represent the mean and range of two independent experiments.

Our findings suggest that a major portion of E2/E1 is immunogenic but does not elicit neutralizing MAbs. The localization of these non-neutralizing epitopes to an unexposed face of the envelope trimer further suggests that these non-neutralizing epitopes may be hidden from the immune system in the native infectious virion (but exposed under other circumstances). Interestingly, in the course of our studies, we observed that the immunoreactivity of some non-neutralizing MAbs was highly dependent on the immunofluorescence assay conditions employed and the format used for E2/E1 presentation. For example, the non-neutralizing fusion loop MAbs CNP2B-H12, IM-CKV061, IM-CKV062, and CAP1A-B3 were essentially non-reactive on cells expressing E2/E1 under native unfixed conditions at room temperature, but were highly reactive following fixation with paraformaldehyde (FIG. 17). A similar trend was observed when CHIKV E2/E1 was presented on the surface of retroviral VLPs, where low levels of MAb reactivity were increased by fixation (FIGS. 18A-D, blue vs. green data points). These data are consistent with a model where epitopes near or within the fusion loop are not well exposed on the native virus.

Because of these observations, we investigated if fusion loop MAbs CNP2B-H12, IM-CKV061, IM-CKV062, and CAP1A-B3 might also display increased reactivity under more physiologically relevant temperatures. In the native unfixed state (FIGS. 18A-D, green data points), these MAbs demonstrated increased immunoreactivity at temperatures of 37° C. and 45° C. compared with room temperature, and reactivity at elevated temperatures was comparable to MAb reactivity under fixed conditions. These results suggest that fusion loop epitopes are shielded at room temperature in their native state but that both elevated temperature and fixation can increase fusion loop epitope exposure. Interestingly, these fusion loop MAbs were still non-neutralizing even after incubation with virus at elevated temperatures (FIG. 19), suggesting that the fusion loop MAbs may be recognizing a subpopulation of E2/E1 with exposed fusion loop structures that no longer contribute to infectivity.

Figure 10:
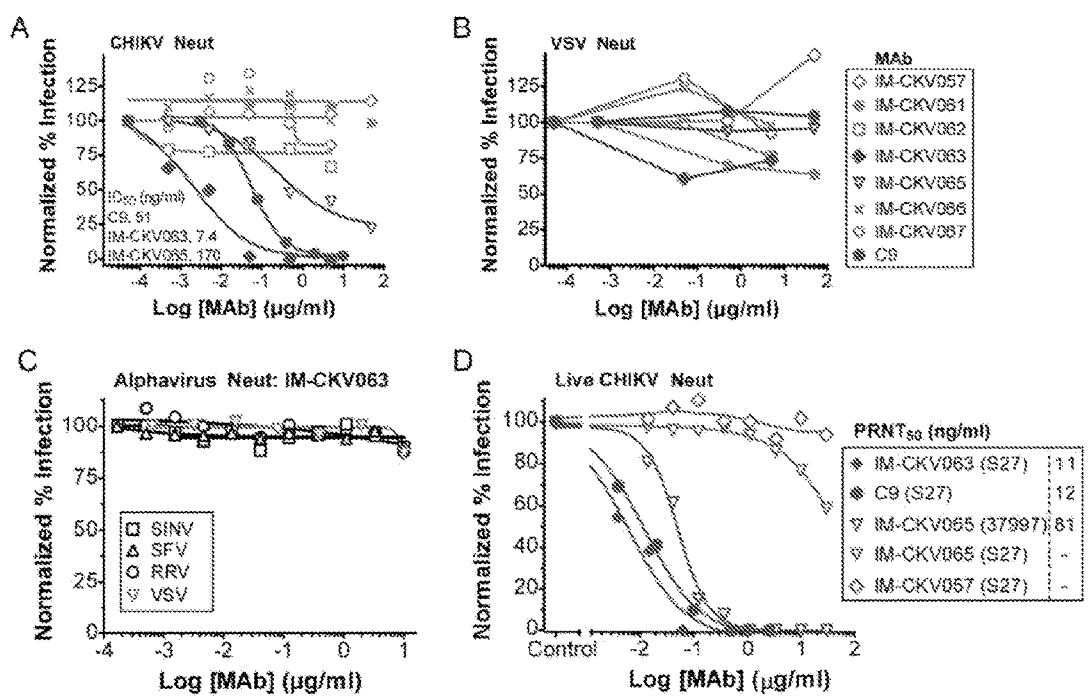
FIG. 10. MAb CAP4A-E7 (IM-CKV063) strongly neutralizes CHIKV. Anti-CHIKV MAbs were tested for the ability to neutralize the infectivity of HIV reporter viruses pseudotyped with (A) CHIKV S27 E2/E1 or (B) VSV envelope. Viruses were pre-incubated with MAbs as described and infection of HEK-293T target cells was detected by the expression of Renilla luciferase. Each data point is the mean of two replicates and data is representative of at least two independent experiments. (C) CAP4A-E7 was tested for neutralization of additional alphavirus envelope proteins pseudotyped onto HIV reporter viruses. Data points represent the mean of three replicates, and data is representative of two independent experiments. (D) Live CHIKV virus was preincubated with MAbs before addition to Vero cells. The S27 strain of CHIKV was used in all experiments. Strain 37997 was also tested against CAP5A-F6. Infectivity was assessed after 72 h using a PRNT assay. Data points represent the mean and standard deviation of two to three replicates, and are representative of at least two individual experiments.
Figure 18:
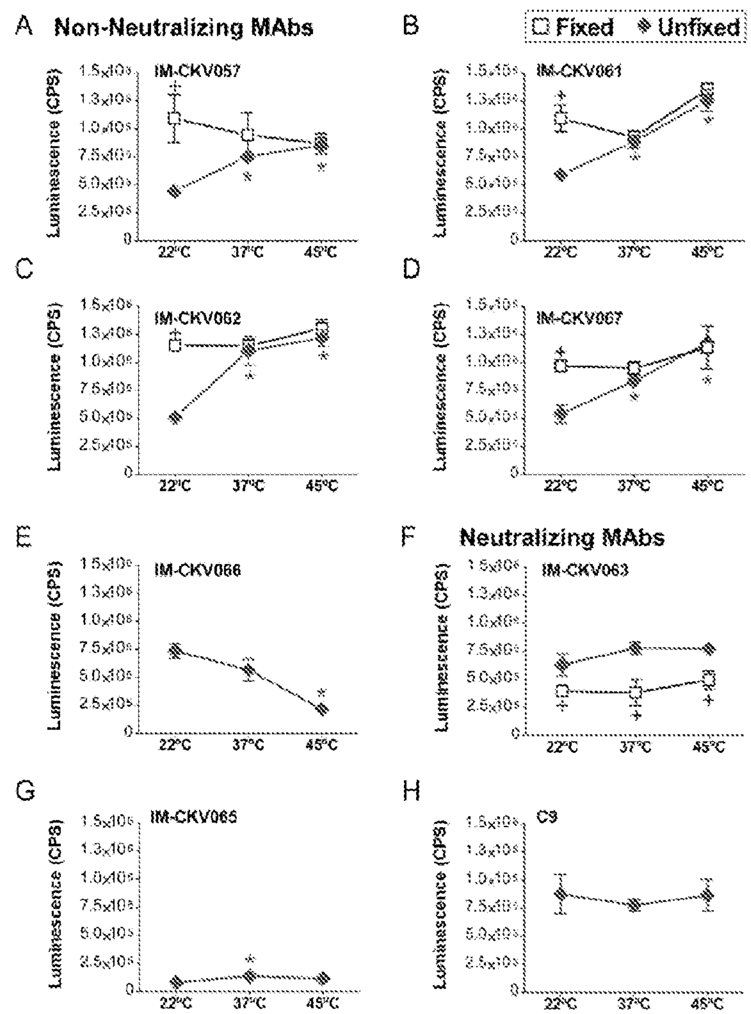
FIG. 18. Temperature dependent MAb reactivity. Immunoreactivity of MAbs (A) CNP2B-H12, (B) IM-CKV061, (C) IM-CKV062, (D) CAP1A-B3, (E) CAP1A-B5, (F) CAP4A-E7, (G) CAP5A-F6, and (H) C9 with CHIKV E2/E1 displayed on the surface of retroviral VLPs was determined at different temperatures and fixation conditions by ELISA. Retroviral VLPs were either fixed using 4% paraformaldehyde at 22° C. or left unfixed. Primary MAb was added at the temperatures indicated for 60 min. Data points represent the mean and S.D. of 3 replicates. MAb reactivities on unfixed cells at elevated temperatures that are different ($p \leq 0.05$) from their respective reactivity at 22° C. are indicated with a green asterisk. MAb reactivities at a specific temperature that are different due to fixation ($p \leq 0.05$) are indicated with a blue plus sign. The experiment was performed twice, and data for one representative experiment is shown. CAP5A-F6 and CAP1A-B5 were not tested under fixed conditions since fixation renders these MAbs poorly reactive.
Figure 19:
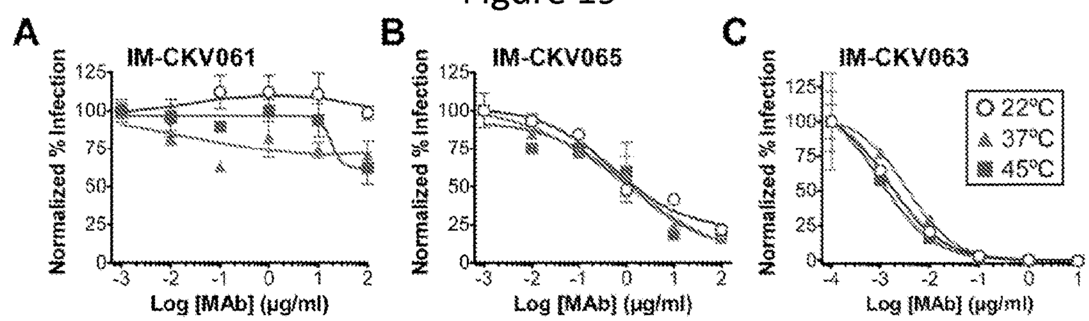
FIG. 19. Temperature-dependent effects of CHIKV MAb neutralization. The effect of temperature on MAb neutralization is shown for a representative (A) non-neutralizing (IM-CKV061), (B) moderately neutralizing (CAP5A-F6), and (C) strongly neutralizing (CAP4A-E7) MAb. HIV reporter viruses pseudotyped with CHIKV S27 E2/E1 were pre-incubated with MAbs at the indicated temperatures, and infection of HEK-293T target cells was detected by the expression of Renilla luciferase. Data shown are representative of two independent experiments. Each data point represents the mean and range of two replicates within an experiment.

The conformational MAb CAP1A-B5 also was sensitive to temperature and fixation, however it showed the opposite trend, where increased temperature and protein fixation led to diminished reactivity (FIGS. 10 and 11E), suggesting that these conditions lead to protein conformational changes that disrupt this discontinuous epitope. Moderately neutralizing MAb CAP5A-F6 has a discontinuous epitope that appears to be sensitive to conformational changes resulting from fixation but not temperature (FIGS. 10 and 11G). It is possible that the Lys233 residue of this epitope is cross-linked to paraformaldehyde during fixation, decreasing its ability to interact with CAP5A-F6. Interestingly, all neutralizing MAbs (regardless of potency) were highly reactive under native unfixed conditions, and temperature did not have a pronounced effect on their ability to bind their epitopes (FIGS. 18F-H). This is consistent with these neutralizing MAbs targeting a well-exposed epitope on the native infectious virus that contributes to the human immune response against CHIKV.

In this example, we isolated and characterized a panel of human MAbs against CHIKV that were derived from naturally-infected patients. To correlate the structural targets of CHIKV MAbs with their protective efficacy, we determined the in vitro neutralization abilities of the MAbs and identified their epitopes using a comprehensive shotgun mutagenesis strategy. Notably, we isolated a potent neutralizing MAb, CAP4A-E7, which prevents CHIKV disease in vivo when administered up to 24 hours post-infection. Other MAbs isolated in our studies suggest that functionally important structures that include the fusion loop are largely hidden from immune recognition in the infectious form of the virus.

Visualization of the binding sites for our and others' MAbs suggest that most epitopes are located in highly immunogenic membrane-distal domains of E2/E1, and that epitopes on the exposed top-most and outer surfaces of the E2/E1 trimer structure are neutralizing whereas epitopes facing the interior of the trimer are not. These results suggest that the neutralizing efficacy of CHIKV MAbs, and possibly MAbs against other alphaviruses, can be predicted, at least in part, based on their epitope location. Specifically, our data suggest that whether the MAbs are neutralizing or non-neutralizing is dependent on the epitope's exposure on the native trimer, with neutralizing MAbs elicited to the exposed external faces and top of the trimer and non-neutralizing MAbs elicited to the occluded inner regions of the E2/E1 subunits facing the interior of the trimer spike. This hypothesis provides a rationale for vaccine design and therapeutic MAb development to target the regions of E2/E1 with greatest neutralization potential. For example, protein subunit vaccines may induce both non-neutralizing and neutralizing MAbs, while virus particle-based vaccines that are locked in their native configuration may preferentially induce neutralizing MAbs against the exposed surfaces of the E2/E1 trimer.

CAP4A-E7 is one of the most potent CHIKV MAbs reported to date (7.4 ng/ml $IC_{50}$, 11 ng/ml $PRNT_{50}$), comparable to the most potent human MAb C9 (51 ng/ml $IC_{50}$, 12 ng/ml $PRNT_{50}$ and murine MAb CHK-152 (2 ng/ml $PRNT_{50}$) described previously. MAb CAP4A-E7 was protective in vivo in two distinct animal models, protecting neonatal mice from death when administered up to 24 hours after virus exposure. Post-exposure experiments testing therapeutic efficacy is particularly relevant to human clinical use, as treatment after infection is often more feasible than prophylaxis. In a separate adult mouse model of CHIKV arthritic disease that more closely recapitulates human symptoms, we found that CAP4A-E7 effectively prevented the arthritis caused by CHIKV. Taken together, the results from these two animal models demonstrate the potential clinical utility of CAP4A-E7 for prophylactic and therapeutic protection against CHIKV-induced disease in humans.

To date, few other reported CHIKV MAbs have been evaluated in a therapeutic (post-infection) context. MAb CHK-152 also provided protection when administered 24 hours post-infection, although using a 10-fold higher dose (100 ug) and in a different animal model (type I IFN receptor knockout mice). MAb CAP4A-E7 appears greatly superior to previously reported human MAbs 5F10 and 8B10, which prolonged survival but did not protect animals from lethality even at much higher MAb doses of 250 ug. CAP4A-E7 thus offers the opportunity to design both therapeutic and passive immunization strategies for treating infected patients or protecting those at risk prior to exposure (e.g. travelers, military personnel). The fact that CAP4A-E7 was originally derived from a patient immune response further suggests that this epitope may be successfully targeted by the human immune system in response to the right vaccine.

MAb CAP4A-E7 binds to an E2 epitope not previously described in the literature. The specific residues involved in CAP4A-E7 binding mapped to the surface exposed regions of domain A known as the 'N-flap' and 'wings', which are possible sites of interaction with a cellular receptor in mammals. Thus, a possible mechanism of action of CAP4A-E7 neutralization is via blocking viral attachment to cells. MAb CAP4A-E7 reactivity was relatively unaffected by changes in temperature or fixation conditions, likely reflecting the favorable surface exposure of its epitope in the native state of the virion. Furthermore, our data suggest that CAP4A-E7 binds to a conformational epitope that spans two E2 subunits. Thus, this MAb may effectively cross-link different E2 domains on the E2/E1 trimer, preventing conformational changes that expose the E1 fusion peptide. Residues in this region of E2 have been shown to be important for conformational changes in E2/E1 that occur during membrane fusion, consistent with this proposed neutralization mechanism. A mutation at residue E2-I121, part of the CAP4A-E7 epitope, has previously been shown to enhance viral infectivity in *Aedes aegypti* and allow MAb escape for VEEV, so CAP4A-E7 could also block other functionalities of E2/E1.

Previous studies have described other neutralizing MAbs that protect against CHIKV in animal models, and also showed that some combinations of MAbs can extend the post-CHIKV exposure window for effective treatment and reduce the development of viral resistance. CAP4A-E7 potently targets an exposed epitope on E2 domain A in a location distinct from other neutralizing MAbs such as C9 or CHK-152. Thus, CAP4A-E7 may be even more highly effective as part of an optimized MAb combination therapy for CHIKV while also minimizing the emergence of resistant mutants.

The non-neutralizing MAbs that we isolated (CNP2B-H12, IM-CKV061, IM-CKV062, CAP1A-B5, and CAP1A-B3) bound overlapping epitopes encompassing the fusion loop and neighboring residues. The fusion loop is a highly-conserved structure among alphaviruses and is of crucial functional importance in viral infection. Consistent with the conserved sequence of this region, MAbs targeting the CHIKV fusion loop demonstrated cross-reactive binding to SFV, RRV, and SINV. However, the fusion loop MAbs were not capable of neutralizing CHIKV in our assays, even after incubation at elevated temperatures. The lack of neutralization was further evident in animal studies where fusion loop MAbs CNP2B-H12 and CAP1A-B5 did not protect mice from CHIKV mortality. We hypothesize that this lack of neutralizing ability is because the fusion loop is hidden in the pre-fusion state of infectious virus, preventing these MAbs from binding and inhibiting infectivity. The increased reactivity of these MAbs with E2/E1 under altered reactivity conditions (elevated temperatures, fixation) is consistent with such a hidden epitope. The presence of fusion loop MAbs in patient samples may be due to an immune response against defective virions or triggered E2/E1 proteins during a natural infection. It is also possible that the method of MAb isolation used in our study, phage display, could influence the types of MAbs recovered.

Given the apparent immunogenicity of the fusion loop, it is interesting to note that only one other MAb against the fusion loop of any alphavirus has been previously reported. In the related alphavirus SFV, fusion loop MAb Elf (that is also non-neutralizing) similarly demonstrated little binding to virus particles under native conditions, binding the fusion loop only when dissociation of the E2/E1 dimer was triggered by low pH. It is likely that non-neutralizing fusion loop MAbs have been isolated by others, but either not characterized as binding the fusion loop or not reported due to their apparent lack of therapeutic potential. For example, we found only two of seven MAbs isolated (29%) to be neutralizing, and Pal et al. similarly identified a relatively small subset (16%) that was neutralizing. The present study mapped epitopes irrespective of MAb neutralization status, a strategy that allows a broader representation of the overall human antibody response against CHIKV. In addition, the method of epitope mapping used here, shotgun mutagenesis, does not require MAb neutralization (as neutralization escape mapping methodologies do) nor requires the maintenance of viral fitness during the acquisition of neutralization escape mutants, so offers a comprehensive epitope mapping approach for conformational and linear MAbs across the entire envelope protein.

In conclusion, the MAbs isolated and characterized in this study demonstrate that the human immune system can generate highly potent, neutralizing MAbs against CHIKV, but that non-neutralizing (e.g. fusion loop-specific) MAbs are also generated in a natural infection against epitopes that are not normally exposed on the native virion. Comparison of the binding sites of neutralizing and non-neutralizing MAbs suggests that vaccination with structurally-intact trimers of E2/E1, as they exist on the native virion, may result in the most highly protective immune response.

The disclosures of each and every patent, patent application, publication, and accession number cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A recombinant antibody comprising a first amino acid sequence comprising the amino acid sequence of SEQ ID NO: 13 and a second amino acid sequence comprising the amino acid sequence of SEQ ID NO: 14.

2. A composition comprising the antibody of claim 1 and a buffer.

3. The composition of claim 2, wherein the composition is a pharmaceutical composition further comprising a pharmaceutically acceptable excipient.

* * * * *

SEQUENCE LISTING

```
<160> NUMBER OF SEQ ID NOS: 36

<210> SEQ ID NO 1
<211> LENGTH: 126
<212> TYPE: PRT
<213> ORGANISM: Artificial Sequence
<220> FEATURE:
<223> OTHER INFORMATION: antibody sequence

<400> SEQUENCE: 1

Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Leu Ser Thr Tyr
            20                  25                  30

Gly Leu His Trp Val Arg Gln Ala Pro Gly Lys Gly Leu Glu Trp Val
        35                  40                  45
```

```
Ala Val Ile Ser Tyr Asp Gly Thr Asn Lys Tyr Tyr Ala Asp Ser Val
    50                  55                  60

Lys Gly Arg Phe Thr Val Ser Trp Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Leu Ala Ser Ser Ser Trp Ser Asp Tyr Tyr His Tyr Gly
            100                 105                 110

Met Asp Val Trp Gly Gln Gly Thr Met Val Thr Val Ser Ser
        115                 120                 125


<210> SEQ ID NO 2
<211> LENGTH: 107
<212> TYPE: PRT
<213> ORGANISM: Artificial Sequence
<220> FEATURE:
<223> OTHER INFORMATION: synthetic sequence

<400> SEQUENCE: 2

Asp Ile Gln Leu Thr Gln Ser Pro Ser Thr Leu Ser Ala Ser Val Gly
1               5                   10                  15

Asp Arg Ile Thr Ile Thr Cys Arg Ala Thr Gln Ser Ile Gly Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Ala Thr Glu Phe Thr Leu Thr Ile Ser Gly Leu Gln Pro
65                  70                  75                  80

Glu Asp Phe Ala Thr Tyr Tyr Cys Gln Gln Leu Lys Ser Phe Pro Leu
                85                  90                  95

Thr Phe Gly Pro Gly Thr Lys Val Asp Ile Gln
            100                 105


<210> SEQ ID NO 3
<211> LENGTH: 122
<212> TYPE: PRT
<213> ORGANISM: Artificial Sequence
<220> FEATURE:
<223> OTHER INFORMATION: synthetic sequence

<400> SEQUENCE: 3

Gln Leu Gln Leu Gln Glu Ser Gly Pro Gly Leu Val Lys Pro Ser Asp
1               5                   10                  15

Thr Leu Ser Leu Thr Cys Ser Val Ser Gly Asp Ser Ile Ser Ser Ser
            20                  25                  30

Tyr Trp Ser Trp Ile Arg Gln Pro Pro Gly Lys Gly Leu Glu Trp Ile
        35                  40                  45

Gly Ala Ile His Tyr Ser Gly Ser Thr Asn Tyr Asn Pro Ser Leu Lys
    50                  55                  60

Ser Arg Val Ala Ile Ser Val Asp Thr Ala Gln Asn His Phe Ser Leu
65                  70                  75                  80

Lys Leu Ser Ser Leu Thr Ala Ala Asp Thr Ala Val Tyr Tyr Cys Ala
                85                  90                  95

Arg Thr Gly Cys Thr Asn Gly Val Cys Tyr Pro Ser Phe Asp Tyr Trp
            100                 105                 110

Gly Gln Gly Thr Leu Val Thr Val Ser Ser
        115                 120
```

<210> SEQ ID NO 4
<211> LENGTH: 107
<212> TYPE: PRT
<213> ORGANISM: Artificial Sequence
<220> FEATURE:
<223> OTHER INFORMATION: synthetic sequence

<400> SEQUENCE: 4

```
Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Gly Ser Arg
            20                  25                  30

Leu Ala Trp Tyr Gln Gln Lys Pro Gly Lys Ala Pro Lys Leu Leu Ile
        35                  40                  45

Tyr Val Ala Ser Ser Leu Gln Ser Gly Val Pro Ser Arg Phe Ser Gly
    50                  55                  60

Ser Gly Ser Ala Thr Asp Phe Thr Leu Thr Ile Ser Ser Leu Gln Pro
65                  70                  75                  80

Glu Asp Phe Ala Thr Tyr Tyr Cys Gln Gln Ala Asp Ser Phe Pro Leu
                85                  90                  95

Thr Phe Gly Gly Gly Thr Arg Val Glu Ile Lys
            100                 105
```

<210> SEQ ID NO 5
<211> LENGTH: 118
<212> TYPE: PRT
<213> ORGANISM: Artificial Sequence
<220> FEATURE:
<223> OTHER INFORMATION: synthetic sequence

<400> SEQUENCE: 5

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ala Phe Arg Ser Tyr
            20                  25                  30

Ala Met Thr Trp Val Arg Gln Ala Pro Gly Lys Gly Leu Glu Trp Val
        35                  40                  45

Ser Thr Ile Ser Gly Ser Thr Gly Asp Thr Tyr Tyr Ala Asp Ser Val
    50                  55                  60

Glu Gly Arg Phe Thr Ile Ser Arg Asp Asn Ser Lys Asp Thr Leu Tyr
65                  70                  75                  80

Leu Gln Met Lys Asn Leu Gly Gly Asp Asp Thr Ala Val Tyr Tyr Cys
                85                  90                  95

Ala Arg Val Leu Gly Thr Gly Trp Phe Asp Pro Trp Gly Gln Gly Thr
            100                 105                 110

Leu Val Thr Val Ser Ser
        115
```

<210> SEQ ID NO 6
<211> LENGTH: 113
<212> TYPE: PRT
<213> ORGANISM: Artificial Sequence
<220> FEATURE:
<223> OTHER INFORMATION: synthetic sequence

<400> SEQUENCE: 6

```
Glu Ile Val Leu Thr Gln Ser Pro Asp Ser Leu Ala Val Ser Leu Gly
1               5                   10                  15
```

```
Glu Arg Ala Thr Ile Asn Cys Lys Ser Ser Gln Ser Val Leu Tyr Ser
            20                  25                  30

Ser Asn Asn Lys Asn Tyr Phe Ala Trp Tyr Gln Gln Lys Pro Gly Gln
        35                  40                  45

Pro Pro Lys Leu Leu Ile Ser Trp Ala Ser Thr Arg Ala Ser Gly Val
    50                  55                  60

Pro Asp Arg Phe Ser Gly Ser Gly Ser Gly Thr Glu Phe Thr Leu Thr
65                  70                  75                  80

Ile Ser Ser Leu Gln Pro Glu Asp Val Ala Val Tyr Tyr Cys Gln Gln
                85                  90                  95

Tyr Tyr Ser Pro Thr Arg Thr Phe Gly Gln Gly Thr Lys Val Glu Ile
            100                 105                 110

Lys


<210> SEQ ID NO 7
<211> LENGTH: 122
<212> TYPE: PRT
<213> ORGANISM: Artificial Sequence
<220> FEATURE:
<223> OTHER INFORMATION: synthetic sequence

<400> SEQUENCE: 7

Gln Val Gln Leu Gln Glu Ser Gly Pro Gly Leu Val Lys Pro Ser Asp
1               5                   10                  15

Thr Leu Ser Leu Thr Cys Ser Val Ser Gly Asp Ser Ile Ser Ser Ser
            20                  25                  30

Tyr Trp Ser Trp Ile Arg Gln Pro Pro Gly Lys Gly Leu Glu Trp Ile
        35                  40                  45

Gly Ala Ile His Tyr Ser Gly Ser Thr Asn Tyr Asn Pro Ser Leu Lys
    50                  55                  60

Ser Arg Val Ala Ile Ser Val Asp Thr Ala Gln Asn His Phe Ser Leu
65                  70                  75                  80

Lys Leu Ser Ser Leu Thr Ala Ala Asp Thr Ala Val Tyr Tyr Cys Ala
                85                  90                  95

Arg Thr Gly Cys Thr Asn Gly Val Cys Tyr Pro Ser Phe Asp Tyr Trp
            100                 105                 110

Gly Gln Gly Thr Leu Val Thr Val Ser Ser
        115                 120


<210> SEQ ID NO 8
<211> LENGTH: 112
<212> TYPE: PRT
<213> ORGANISM: Artificial Sequence
<220> FEATURE:
<223> OTHER INFORMATION: synthetic sequence

<400> SEQUENCE: 8

Glu Ile Val Leu Thr Gln Ser Pro Leu Ser Leu Thr Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80
```

```
Ser Arg Val Glu Ala Glu Asp Val Gly Val Tyr Tyr Cys Met Gln Gly
                85                  90                  95

Thr Gly Trp Pro Trp Thr Phe Gly Gln Gly Thr Lys Val Glu Ile Arg
            100                 105                 110


<210> SEQ ID NO 9
<211> LENGTH: 122
<212> TYPE: PRT
<213> ORGANISM: Artificial Sequence
<220> FEATURE:
<223> OTHER INFORMATION: synthetic sequence

<400> SEQUENCE: 9

Glu Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Gly Val Ser Trp Val Arg Gln Ala Pro Gly Gln Gly Leu Glu Trp Leu
        35                  40                  45

Gly Trp Ile Ser Ala Tyr Asn Gly Asn Thr Lys Tyr Ala Gln Lys Phe
    50                  55                  60

Glu Gly Arg Val Thr Leu Thr Thr Asp Ser Leu Ser Asp Thr Ala Tyr
65                  70                  75                  80

Met Glu Leu Arg Ser Leu Arg Ser Asp Asp Thr Ala Val Tyr Tyr Cys
                85                  90                  95

Val Arg Asp Asp Arg Ser Gly Tyr Tyr Tyr Leu Pro Phe Asp Phe Trp
            100                 105                 110

Gly Gln Gly Thr Leu Val Thr Val Ser Ser
        115                 120


<210> SEQ ID NO 10
<211> LENGTH: 107
<212> TYPE: PRT
<213> ORGANISM: Artificial Sequence
<220> FEATURE:
<223> OTHER INFORMATION: synthetic sequence

<400> SEQUENCE: 10

Asp Ile Gln Leu Thr Gln Ser Pro Ser Ser Val Ser Ala Ser Val Gly
1               5                   10                  15

Asp Gly Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Tyr
                85                  90                  95

Thr Phe Gly Gln Gly Thr Lys Leu Glu Ile Lys
            100                 105


<210> SEQ ID NO 11
<211> LENGTH: 122
<212> TYPE: PRT
<213> ORGANISM: Artificial Sequence
<220> FEATURE:
<223> OTHER INFORMATION: synthetic sequence
```

<400> SEQUENCE: 11

```
Gln Val Gln Leu Gln Glu Ser Gly Pro Gly Leu Val Lys Pro Ser Asp
1               5                   10                  15

Thr Leu Ser Leu Thr Cys Ser Val Ser Gly Asp Ser Ile Ser Ser Ser
            20                  25                  30

Tyr Trp Ser Trp Ile Arg Gln Pro Pro Gly Lys Gly Leu Glu Trp Ile
        35                  40                  45

Gly Ala Ile His Tyr Ser Gly Ser Thr Asn Tyr Asn Pro Ser Leu Lys
    50                  55                  60

Ser Arg Val Ala Ile Ser Val Asp Thr Ala Gln Asn His Phe Ser Leu
65                  70                  75                  80

Lys Leu Ser Ser Leu Thr Ala Ala Asp Thr Ala Val Tyr Tyr Cys Ala
                85                  90                  95

Arg Thr Gly Cys Thr Asn Gly Val Cys Tyr Pro Ser Phe Asp Tyr Trp
            100                 105                 110

Gly Arg Gly Thr Leu Val Thr Val Ser Ser
        115                 120
```

<210> SEQ ID NO 12
<211> LENGTH: 107
<212> TYPE: PRT
<213> ORGANISM: Artificial Sequence
<220> FEATURE:
<223> OTHER INFORMATION: synthetic sequence

<400> SEQUENCE: 12

```
Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Thr Asn Leu
            20                  25                  30

Leu Gly Trp Tyr Gln His Lys Pro Gly Glu Ala Pro Lys Leu Leu Ile
        35                  40                  45

Tyr Thr Ser Ser Thr Leu Gln Pro Gly Val Pro Ser Arg Phe Arg Gly
    50                  55                  60

Ser Gly Ser Gly Thr Asp Phe Ser Leu Thr Ile Thr Ser Leu Gln Pro
65                  70                  75                  80

Glu Asp Phe Ala Thr Tyr Phe Cys Gln Gln Ala His Ser Phe Pro Leu
                85                  90                  95

Thr Phe Gly Gly Gly Thr Lys Val Glu Ile Arg
            100                 105
```

<210> SEQ ID NO 13
<211> LENGTH: 134
<212> TYPE: PRT
<213> ORGANISM: Artificial Sequence
<220> FEATURE:
<223> OTHER INFORMATION: synthetic sequence

<400> SEQUENCE: 13

```
Gln Val Gln Leu Val Gln Ser Gly Ala Glu Val Lys Lys Pro Gly Ser
1               5                   10                  15

Ala Val Lys Val Ser Cys Lys Ala Ser Gly Gly Thr Leu Arg Lys Tyr
            20                  25                  30

Ala Ile Ser Trp Leu Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60
```

```
Gln Gly Arg Val Thr Ile Thr Ala Asp Glu Ser Thr Thr Thr Pro Tyr
65                  70                  75                  80

Thr Thr Thr Pro Tyr Thr Ser Thr Ala Tyr Ile Glu Leu Thr Ser Leu
                85                  90                  95

Arg Ser Glu Asp Thr Ala Val Tyr Tyr Cys Ala Arg Asp Leu Gly Pro
            100                 105                 110

Leu Thr Gly Tyr Ser Tyr Ser Tyr Phe Asp Tyr Trp Gly Gln Gly Thr
        115                 120                 125

Leu Val Thr Val Ser Ser
    130


<210> SEQ ID NO 14
<211> LENGTH: 107
<212> TYPE: PRT
<213> ORGANISM: Artificial Sequence
<220> FEATURE:
<223> OTHER INFORMATION: synthetic sequence

<400> SEQUENCE: 14

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Ala Asn Ser Arg Arg
                85                  90                  95

Thr Phe Gly Gln Gly Thr Lys Val Glu Ile Thr
            100                 105


<210> SEQ ID NO 15
<211> LENGTH: 122
<212> TYPE: PRT
<213> ORGANISM: Artificial Sequence
<220> FEATURE:
<223> OTHER INFORMATION: synthetic sequence

<400> SEQUENCE: 15

Glu Val Gln Leu Val Gln Ser Gly Pro Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Gly Val Ser Trp Val Arg Gln Ala Pro Gly Gln Gly Leu Glu Trp Leu
        35                  40                  45

Gly Trp Ile Ser Ala Tyr Asn Gly Asn Thr Lys Tyr Ala Gln Lys Phe
    50                  55                  60

Glu Gly Arg Val Thr Leu Thr Thr Asp Ser Leu Ser Asp Thr Ala Tyr
65                  70                  75                  80

Met Glu Leu Arg Ser Leu Arg Ser Asp Asp Thr Ala Val Tyr Tyr Cys
                85                  90                  95

Val Arg Asp Asp Arg Ser Gly Tyr Tyr Tyr Leu Pro Phe Asp Phe Trp
            100                 105                 110

Gly Gln Gly Thr Leu Val Thr Val Ser Ser
        115                 120
```

<210> SEQ ID NO 16
<211> LENGTH: 106
<212> TYPE: PRT
<213> ORGANISM: Artificial Sequence
<220> FEATURE:
<223> OTHER INFORMATION: synthetic sequence

<400> SEQUENCE: 16

```
Asp Ile Gln Leu Thr Gln Ser Pro Ser Phe Leu Ser Ala Ser Val Gly
1               5                   10                  15

Asp Arg Val Thr Ile Thr Cys Arg Ala Ser Gln Gly Ile Ser Ser Tyr
            20                  25                  30

Leu Ala Trp Tyr Gln Gln Lys Pro Gly Lys Ala Pro Lys Leu Leu Ile
        35                  40                  45

Phe Ala Ala Ser Thr Leu Gln Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Gln Ser Tyr Ser Asn Pro Thr
                85                  90                  95

Phe Gly Gln Gly Thr Arg Leu Glu Ile Lys
            100                 105
```

<210> SEQ ID NO 17
<211> LENGTH: 127
<212> TYPE: PRT
<213> ORGANISM: Homo sapiens

<400> SEQUENCE: 17

```
Glu Val Gln Leu Val Gln Ser Gly Ala Glu Val Lys Lys Pro Gly Ser
1               5                   10                  15

Ser Val Lys Val Ser Cys Lys Ala Phe Gly Gly Thr Phe Ser Ser Tyr
            20                  25                  30

Ala Ile Thr Trp Val Arg Gln Ala Pro Gly Gln Gly Leu Glu Trp Met
        35                  40                  45

Gly Gly Ile Ile Pro Ile Leu Gly Thr Thr Asp Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Pro Pro Thr His Gly Gly Asp Phe Asn Tyr Tyr Tyr Tyr
            100                 105                 110

Gly Val Ala Val Trp Gly Gln Gly Thr Thr Val Thr Val Ser Ser
        115                 120                 125
```

<210> SEQ ID NO 18
<211> LENGTH: 106
<212> TYPE: PRT
<213> ORGANISM: Homo sapiens

<400> SEQUENCE: 18

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Asn Asn Tyr Leu
            20                  25                  30

Ala Trp Tyr Gln Gln Lys Pro Gly Gln Ala Pro Arg Leu Leu Ile Tyr
```

```
        35                  40                  45

Gly Ala Ser Ile Arg Ala Thr Gly Ile Pro Asp Arg Phe Ser Gly Ser
    50                  55                  60

Gly Ser Gly Thr Asp Phe Thr Leu Thr Ile Ser Arg Leu Ala Pro Glu
65                  70                  75                  80

Asp Phe Ala Val Tyr Tyr Cys Gln Gln Tyr Gly Ser Ser Pro Leu Thr
                85                  90                  95

Phe Gly Pro Gly Thr Lys Val Asp Ile Lys
            100                 105


<210> SEQ ID NO 19
<211> LENGTH: 117
<212> TYPE: PRT
<213> ORGANISM: Artificial Sequence
<220> FEATURE:
<223> OTHER INFORMATION: synthetic sequence

<400> SEQUENCE: 19

Glu Val Gln Leu Val Glu Ser Gly Gly Asp Leu Val Gln Pro Gly Gly
1               5                   10                  15

Ser Leu Thr Pro Ser Cys Val Ile Ser Glu Phe Thr Phe Ser Thr Ser
            20                  25                  30

Trp Met Gly Trp Val Arg Gln Ala Pro Gly Lys Gly Leu Glu Cys Val
        35                  40                  45

Ala Ser Ile Lys Thr Asp Gly Ser Glu Lys Tyr Tyr Val Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Val Ala Asp Thr Ala Val Tyr Tyr Cys
                85                  90                  95

Ala Arg His Gly Ala Tyr Thr Tyr Asp Ser Trp Gly Pro Gly Thr Leu
            100                 105                 110

Val Thr Val Ser Ser
        115


<210> SEQ ID NO 20
<211> LENGTH: 113
<212> TYPE: PRT
<213> ORGANISM: Artificial Sequence
<220> FEATURE:
<223> OTHER INFORMATION: synthetic sequence

<400> SEQUENCE: 20

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Ile Leu Tyr Ser
            20                  25                  30

Ser Asp Asn Lys Asn Tyr Leu Ser Trp Ile Gln Gln Lys Pro Gly Gln
        35                  40                  45

Pro Pro Lys Val Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Arg Thr Pro Ile Thr Phe Gly Gln Gly Thr Arg Leu Glu Ile
            100                 105                 110
```

Lys

<210> SEQ ID NO 21
<211> LENGTH: 122
<212> TYPE: PRT
<213> ORGANISM: Artificial Sequence
<220> FEATURE:
<223> OTHER INFORMATION: synthetic sequence

<400> SEQUENCE: 21

```
Gln Val Gln Leu Gln Glu Ser Gly Pro Gly Leu Val Lys Pro Ser Asp
1               5                   10                  15

Thr Leu Ser Leu Thr Cys Ser Val Ser Gly Asp Ser Ile Ser Ser Ser
            20                  25                  30

Tyr Trp Ser Trp Ile Arg Gln Pro Pro Gly Lys Gly Leu Glu Trp Ile
        35                  40                  45

Gly Ala Ile His Tyr Ser Gly Ser Thr Asn Tyr Asn Pro Ser Leu Lys
    50                  55                  60

Ser Arg Val Ala Met Ser Val Asp Thr Ala Gln Asn His Phe Ser Leu
65                  70                  75                  80

Lys Leu Ser Ser Leu Thr Ala Ala Asp Thr Ala Val Tyr Tyr Cys Ala
                85                  90                  95

Arg Thr Gly Cys Thr Asn Gly Val Cys Tyr Pro Ser Phe Asp Tyr Trp
            100                 105                 110

Gly Gln Gly Thr Leu Val Thr Val Ser Ser
        115                 120
```

<210> SEQ ID NO 22
<211> LENGTH: 107
<212> TYPE: PRT
<213> ORGANISM: Artificial Sequence
<220> FEATURE:
<223> OTHER INFORMATION: synthetic sequence

<400> SEQUENCE: 22

```
Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys
            100                 105
```

<210> SEQ ID NO 23
<211> LENGTH: 122
<212> TYPE: PRT
<213> ORGANISM: Artificial Sequence
<220> FEATURE:
<223> OTHER INFORMATION: synthetic sequence

<400> SEQUENCE: 23

```
Gln Val Gln Leu Gln Glu Ser Gly Pro Gly Leu Val Lys Pro Ser Asp
1               5                   10                  15
```

```
Thr Leu Ser Leu Thr Cys Ser Val Ser Gly Asp Ser Ile Ser Ser Ser
            20                  25                  30

Tyr Trp Ser Trp Ile Arg Gln Pro Pro Gly Lys Gly Leu Glu Trp Ile
        35                  40                  45

Gly Ala Ile His Tyr Ser Gly Ser Thr Asn Tyr Asn Pro Ser Leu Lys
    50                  55                  60

Ser Arg Val Ala Ile Ser Val Asp Thr Ala Gln Asn His Phe Ser Leu
65                  70                  75                  80

Lys Leu Ser Ser Leu Thr Ala Ala Asp Thr Ala Val Tyr Tyr Cys Ala
                85                  90                  95

Arg Thr Gly Cys Thr Asn Gly Val Cys Tyr Pro Ser Phe Asp Tyr Trp
            100                 105                 110

Gly Gln Gly Thr Leu Val Thr Val Ser Ser
        115                 120


<210> SEQ ID NO 24
<211> LENGTH: 112
<212> TYPE: PRT
<213> ORGANISM: Artificial Sequence
<220> FEATURE:
<223> OTHER INFORMATION: synthetic sequence

<400> SEQUENCE: 24

Glu Ile Val Leu Thr Gln Ser Pro Leu Ser Leu Thr Val Thr Leu Gly
1               5                   10                  15

Gln Pro Ala Ser Ile Ser Cys Arg Ser Ser Gln Ser Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr Gly Trp Pro Trp Thr Phe Gly Gln Gly Thr Lys Val Glu Ile Arg
            100                 105                 110


<210> SEQ ID NO 25
<211> LENGTH: 122
<212> TYPE: PRT
<213> ORGANISM: Artificial Sequence
<220> FEATURE:
<223> OTHER INFORMATION: synthetic sequence

<400> SEQUENCE: 25

Gln Val Gln Leu Gln Glu Ser Gly Pro Gly Leu Val Lys Pro Ser Asp
1               5                   10                  15

Thr Leu Ser Leu Thr Cys Ser Val Ser Gly Asp Ser Ile Ser Ser Ser
            20                  25                  30

Tyr Trp Ser Trp Ile Arg Gln Pro Pro Gly Lys Gly Leu Glu Trp Ile
        35                  40                  45

Gly Ala Ile His Tyr Ser Gly Ser Thr Asn Tyr Asn Pro Ser Leu Lys
    50                  55                  60

Ser Arg Val Ala Ile Ser Val Asp Thr Ala Gln Asn His Phe Ser Leu
65                  70                  75                  80

Lys Leu Ser Ser Leu Thr Ala Ala Asp Thr Ala Val Tyr Tyr Cys Ala
```

```
                85                  90                  95

Arg Thr Gly Cys Thr Asn Gly Val Cys Tyr Pro Ser Phe Asp Tyr Trp
            100                 105                 110

Gly Arg Gly Thr Leu Val Thr Val Ser Ser
        115                 120


<210> SEQ ID NO 26
<211> LENGTH: 107
<212> TYPE: PRT
<213> ORGANISM: Artificial Sequence
<220> FEATURE:
<223> OTHER INFORMATION: synthetic sequence

<400> SEQUENCE: 26

Asp Ile Gln Leu Thr Gln Ser Pro Ser Ser Val Ser Ala Ser Val Gly
1               5                   10                  15

Asp Arg Val Thr Ile Thr Cys Arg Ala Ser Gln Gly Ile Thr Asn Leu
            20                  25                  30

Leu Gly Trp Tyr Gln His Lys Pro Gly Glu Ala Pro Lys Leu Leu Ile
        35                  40                  45

Tyr Thr Ser Ser Thr Leu Gln Pro Gly Val Pro Ser Arg Phe Arg Gly
    50                  55                  60

Ser Gly Ser Gly Thr Asp Phe Ser Leu Thr Ile Thr Ser Leu Gln Pro
65                  70                  75                  80

Glu Asp Phe Ala Thr Tyr Phe Cys Gln Gln Ala His Ser Phe Pro Leu
                85                  90                  95

Thr Phe Gly Gly Gly Thr Lys Val Glu Ile Arg
            100                 105


<210> SEQ ID NO 27
<211> LENGTH: 988
<212> TYPE: PRT
<213> ORGANISM: Chikungunya virus

<400> SEQUENCE: 27

Met Ser Leu Ala Ile Pro Val Met Cys Leu Leu Ala Asn Thr Thr Phe
1               5                   10                  15

Pro Cys Ser Gln Pro Pro Cys Ile Pro Cys Cys Tyr Glu Lys Glu Pro
            20                  25                  30

Glu Glu Thr Leu Arg Met Leu Glu Asp Asn Val Met Arg Pro Gly Tyr
        35                  40                  45

Tyr Gln Leu Leu Gln Ala Ser Leu Thr Cys Ser Pro His Arg Gln Arg
    50                  55                  60

Arg Ser Thr Lys Asp Asn Phe Asn Val Tyr Lys Ala Thr Arg Pro Tyr
65                  70                  75                  80

Leu Ala His Cys Pro Asp Cys Gly Glu Gly His Ser Cys His Ser Pro
                85                  90                  95

Val Ala Leu Glu Arg Ile Arg Asn Glu Ala Thr Asp Gly Thr Leu Lys
            100                 105                 110

Ile Gln Val Ser Leu Gln Ile Gly Ile Gly Thr Asp Asp Ser His Asp
        115                 120                 125

Trp Thr Lys Leu Arg Tyr Met Asp Asn His Ile Pro Ala Asp Ala Gly
    130                 135                 140

Arg Ala Gly Leu Phe Val Arg Thr Ser Ala Pro Cys Thr Ile Thr Gly
145                 150                 155                 160

Thr Met Gly His Phe Ile Leu Ala Arg Cys Pro Lys Gly Glu Thr Leu
                165                 170                 175
```

```
Thr Val Gly Phe Thr Asp Ser Arg Lys Ile Ser His Ser Cys Thr His
            180                 185                 190

Pro Phe His His Asp Pro Pro Val Ile Gly Arg Glu Lys Phe His Ser
        195                 200                 205

Arg Pro Gln His Gly Lys Glu Leu Pro Cys Ser Thr Tyr Val Gln Ser
    210                 215                 220

Asn Ala Ala Thr Ala Glu Glu Ile Glu Val His Met Pro Pro Asp Thr
225                 230                 235                 240

Pro Asp Arg Thr Leu Leu Ser Gln Gln Ser Gly Asn Val Lys Ile Thr
                245                 250                 255

Val Asn Ser Gln Thr Val Arg Tyr Lys Cys Asn Cys Gly Gly Ser Asn
            260                 265                 270

Glu Gly Leu Ile Thr Thr Asp Lys Val Ile Asn Asn Cys Lys Val Asp
        275                 280                 285

Gln Cys His Ala Ala Val Thr Asn His Lys Lys Trp Gln Tyr Asn Ser
    290                 295                 300

Pro Leu Val Pro Arg Asn Ala Glu Leu Gly Asp Arg Lys Gly Lys Ile
305                 310                 315                 320

His Ile Pro Phe Pro Leu Ala Asn Val Thr Cys Met Val Pro Lys Ala
                325                 330                 335

Arg Asn Pro Thr Val Thr Tyr Gly Lys Asn Gln Val Ile Met Leu Leu
            340                 345                 350

Tyr Pro Asp His Pro Thr Leu Leu Ser Tyr Arg Ser Met Gly Glu Glu
        355                 360                 365

Pro Asn Tyr Gln Glu Glu Trp Val Thr His Lys Lys Glu Val Val Leu
    370                 375                 380

Thr Val Pro Thr Glu Gly Leu Glu Val Thr Trp Gly Asn Asn Glu Pro
385                 390                 395                 400

Tyr Lys Tyr Trp Pro Gln Leu Ser Ala Asn Gly Thr Ala His Gly His
                405                 410                 415

Pro His Glu Ile Ile Leu Tyr Tyr Tyr Glu Leu Tyr Pro Thr Met Thr
            420                 425                 430

Val Val Val Val Ser Val Ala Ser Phe Ile Leu Leu Ser Met Val Gly
        435                 440                 445

Met Ala Val Gly Met Cys Met Cys Ala Arg Arg Arg Cys Ile Thr Pro
    450                 455                 460

Tyr Glu Leu Thr Pro Gly Ala Thr Val Pro Phe Leu Leu Ser Leu Ile
465                 470                 475                 480

Cys Cys Ile Arg Thr Ala Lys Ala Ala Thr Tyr Gln Glu Ala Ala Val
                485                 490                 495

Tyr Leu Trp Asn Glu Gln Gln Pro Leu Phe Trp Leu Gln Ala Leu Ile
            500                 505                 510

Pro Leu Ala Ala Leu Ile Val Leu Cys Asn Cys Leu Arg Leu Leu Pro
        515                 520                 525

Cys Cys Cys Lys Thr Leu Ala Phe Leu Ala Val Met Ser Ile Gly Ala
    530                 535                 540

His Thr Val Ser Ala Tyr Glu His Val Thr Val Ile Pro Asn Thr Val
545                 550                 555                 560

Gly Val Pro Tyr Lys Thr Leu Val Asn Arg Pro Gly Tyr Ser Pro Met
                565                 570                 575

Val Leu Glu Met Glu Leu Leu Ser Val Thr Leu Glu Pro Thr Leu Ser
            580                 585                 590
```

```
Leu Asp Tyr Ile Thr Cys Glu Tyr Lys Thr Val Ile Pro Ser Pro Tyr
        595                 600                 605

Val Lys Cys Cys Gly Thr Ala Glu Cys Lys Asp Lys Asn Leu Pro Asp
    610                 615                 620

Tyr Ser Cys Lys Val Phe Thr Gly Val Tyr Pro Phe Met Trp Gly Gly
625                 630                 635                 640

Ala Tyr Cys Phe Cys Asp Ala Glu Asn Thr Gln Leu Ser Glu Ala His
                645                 650                 655

Val Glu Lys Ser Glu Ser Cys Lys Thr Glu Phe Ala Ser Ala Tyr Arg
            660                 665                 670

Ala His Thr Ala Ser Ala Ser Ala Lys Leu Arg Val Leu Tyr Gln Gly
        675                 680                 685

Asn Asn Ile Thr Val Thr Ala Tyr Ala Asn Gly Asp His Ala Val Thr
    690                 695                 700

Val Lys Asp Ala Lys Phe Ile Val Gly Pro Met Ser Ser Ala Trp Thr
705                 710                 715                 720

Pro Phe Asp Asn Lys Ile Val Val Tyr Lys Gly Asp Val Tyr Asn Met
                725                 730                 735

Asp Tyr Pro Pro Phe Gly Ala Gly Arg Pro Gly Gln Phe Gly Asp Ile
            740                 745                 750

Gln Ser Arg Thr Pro Glu Ser Lys Asp Val Tyr Ala Asn Thr Gln Leu
        755                 760                 765

Val Leu Gln Arg Pro Ala Ala Gly Thr Val His Val Pro Tyr Ser Gln
    770                 775                 780

Ala Pro Ser Gly Phe Lys Tyr Trp Leu Lys Glu Arg Gly Ala Ser Leu
785                 790                 795                 800

Gln His Thr Ala Pro Phe Gly Cys Gln Ile Ala Thr Asn Pro Val Arg
                805                 810                 815

Ala Met Asn Cys Ala Val Gly Asn Met Pro Ile Ser Ile Asp Ile Pro
            820                 825                 830

Asp Ala Ala Phe Thr Arg Val Val Asp Ala Pro Ser Leu Thr Asp Met
        835                 840                 845

Ser Cys Glu Val Pro Ala Cys Thr His Ser Ser Asp Phe Gly Gly Val
    850                 855                 860

Ala Ile Ile Lys Tyr Ala Val Ser Lys Lys Gly Lys Cys Ala Val His
865                 870                 875                 880

Ser Met Thr Asn Ala Val Thr Ile Arg Glu Ala Glu Ile Glu Val Glu
                885                 890                 895

Gly Asn Ser Gln Leu Gln Ile Ser Phe Ser Thr Ala Leu Ala Ser Ala
            900                 905                 910

Glu Phe Arg Val Gln Val Cys Ser Thr Gln Val His Cys Ala Ala Glu
        915                 920                 925

Cys His Pro Pro Lys Asp His Ile Val Asn Tyr Pro Ala Ser His Thr
    930                 935                 940

Thr Leu Gly Val Gln Asp Ile Ser Ala Thr Ala Met Ser Trp Val Gln
945                 950                 955                 960

Lys Ile Thr Gly Gly Val Gly Leu Val Val Ala Val Ala Ala Leu Ile
                965                 970                 975

Leu Ile Val Val Leu Cys Val Ser Phe Ser Arg His
            980                 985
```

<210> SEQ ID NO 28
<211> LENGTH: 2964
<212> TYPE: DNA

<213> ORGANISM: Chikungunya virus

<400> SEQUENCE: 28

```
atgtcactag ccatccctgt gatgtgtctg ctcgccaaca caactttccc atgctctcag     60
ccaccctgta taccctgctg ctatgagaaa gaacctgagg agaccctgcg catgctggag    120
gacaatgtta tgaggccagg ctactaccaa ctattgcagg caagtttgac ctgctcacca    180
cataggcagc gccgatccac aaaagataac ttcaacgttt acaaagctac tcgaccctat    240
ttggcccact gcccggattg tggggaagga cactcctgcc actctcccgt ggccctcgaa    300
cgaattagga acgaggctac tgacggaacc ctaaagattc aggtatcact ccagatcgga    360
atagggacag acgactctca cgattggaca aaactcagat atatggataa ccacatcccc    420
gccgacgctg gcagagccgg tcttttcgtt cgcacatccg ctccctgcac aataacgggt    480
accatggggc atttcattct ggcgcggtgc ccgaagggag agacccttac agtgggcttt    540
accgactccc gcaagatttc tcatagctgt acccatccct tccatcacga tcctcctgta    600
atcggccggg agaaattcca ctcccggccg caacatggca aagagctgcc ctgttctacc    660
tatgtacaaa gcaacgccgc gactgccgag gaaatagagg tgcacatgcc accagatacc    720
cccgatcgaa cacttctttc tcaacaaagt ggcaacgtaa aaatcacagt taacagccag    780
actgtgcggt ataagtgcaa ctgtgggggt tccaatgaag gcctcatcac gactgacaag    840
gtgatcaata actgcaaggt cgaccagtgt cacgccgcgg tgacgaatca caaaaagtgg    900
cagtataact ctccgcttgt gccacgtaac gccgagctgg gggatagaaa ggggaagatc    960
cacatcccct ttccactggc taatgtcacg tgcatggtgc cgaaggctag aaatcctaca   1020
gtaacttacg gaaagaatca agtgatcatg ttattatatc ctgaccatcc gactctcctg   1080
agttatagat caatgggcga agaacctaac taccaagaag agtgggtcac ccacaagaag   1140
gaggtggttt taacagtgcc aaccgaaggt cttgaagtga cctggggcaa taacgaaccc   1200
tacaagtatt ggccacagct gtccgctaat ggcacggccc acggtcaccc ccacgagatc   1260
atactgtact actatgaact ataccctact atgaccgtgg tggtggtgag cgtggcctcc   1320
ttcattctcc tcagcatggt ggggatggct gtcggaatgt gcatgtgcgc gcgccggcga   1380
tgtattacgc cttacgagct gactcccggc gccaccgttc cgtttctgct aagcttgatc   1440
tgttgtatca ggacggccaa ggcagctacc tatcaggagg cggctgtata cctctggaac   1500
gagcagcagc cactcttctg gcttcaggcc ctgatcccct tggcagccct catagtgctg   1560
tgcaactgtc tgcgtctgct cccatgttgt tgcaagacac tggccttcct ggcagtgatg   1620
agcattggcg cgcacactgt ttcagcctat gaacatgtga ccgtaattcc taacactgtc   1680
ggggtgccct acaagacctt ggttaaccgc ccggggtata gccccatggt tctcgagatg   1740
gaacttctgt cggtaacgtt ggagccgacc ctttcccttg actatattac atgtgagtac   1800
aagacggtga ttccatctcc ctacgtgaag tgctgcggta ctgctgaatg caaggacaaa   1860
aatctccctg attactcgtg caaggtattc actggagtgt acccatttat gtggggaggc   1920
gcttattgtt tctgtgatgc tgaaaacacc caattatctg aagcccatgt ggagaaaagc   1980
gagtcctgta aaactgagtt cgccagcgcc tatcgtgcgc acaccgcttc tgcctccgcc   2040
aagcttaggg tgctatacca gggcaataat ataaccgtta ctgcatatgc gaacggagac   2100
catgcagtta ctgtaaaaga tgcaaaattt atagtgggcc ccatgagttc ggcttggaca   2160
cccttcgaca ataagatagt cgtgtacaag ggcgacgtgt acaatatgga ctacccacct   2220
ttcggcgctg gccgtcctgg tcagttcgga gacatccaaa gccggacacc tgagtccaag   2280
```

```
gacgtctacg caaacacaca gcttgtcctg cagcggccag cagccgggac agttcacgtg   2340

ccttacagcc aggcgcccag tggctttaag tattggctaa aggaaagggg ggcgagtctc   2400

cagcatactg ccccccttcgg ctgccagatt gcaactaacc ccgtgcgagc tatgaattgc   2460

gcagtcggca acatgcctat ctctattgat atcccggacg ccgcttttac tcgtgtcgtg   2520

gacgctccca gcctgacgga catgtcctgc gaagttcctg catgcaccca ctcatccgat   2580

tttggaggtg tggcaataat caaatatgca gtcagtaaaa agggtaagtg tgccgtccac   2640

tcgatgacga atgccgtgac tatcagagag gcagagatcg aagtggaagg aaatagccag   2700

ttgcaaatct ctttcagcac agcccttgca agtgccgagt ttcgcgtcca agtgtgtagc   2760

acgcaggttc actgtgcagc cgaatgtcat ccgcctaaag accacatagt caattacccc   2820

gcttcccaca ccacattggg agttcaggac ataagtgcta ctgctatgag ctgggtccaa   2880

aagatcaccg gaggtgtagg gctcgtcgtg gccgtcgccg ctctaattct gatcgtggtt   2940

ctgtgcgtca gtttttcccg tcac                                           2964
```

```
<210> SEQ ID NO 29
<211> LENGTH: 439
<212> TYPE: PRT
<213> ORGANISM: Chikungunya virus

<400> SEQUENCE: 29

Tyr Glu His Val Thr Val Ile Pro Asn Thr Val Gly Val Pro Tyr Lys
1               5                   10                  15

Thr Leu Val Asn Arg Pro Gly Tyr Ser Pro Met Val Leu Glu Met Glu
            20                  25                  30

Leu Leu Ser Val Thr Leu Glu Pro Thr Leu Ser Leu Asp Tyr Ile Thr
        35                  40                  45

Cys Glu Tyr Lys Thr Val Ile Pro Ser Pro Tyr Val Lys Cys Cys Gly
    50                  55                  60

Thr Ala Glu Cys Lys Asp Lys Asn Leu Pro Asp Tyr Ser Cys Lys Val
65                  70                  75                  80

Phe Thr Gly Val Tyr Pro Phe Met Trp Gly Gly Ala Tyr Cys Phe Cys
                85                  90                  95

Asp Ala Glu Asn Thr Gln Leu Ser Glu Ala His Val Glu Lys Ser Glu
            100                 105                 110

Ser Cys Lys Thr Glu Phe Ala Ser Ala Tyr Arg Ala His Thr Ala Ser
        115                 120                 125

Ala Ser Ala Lys Leu Arg Val Leu Tyr Gln Gly Asn Asn Ile Thr Val
    130                 135                 140

Thr Ala Tyr Ala Asn Gly Asp His Ala Val Thr Val Lys Asp Ala Lys
145                 150                 155                 160

Phe Ile Val Gly Pro Met Ser Ser Ala Trp Thr Pro Phe Asp Asn Lys
                165                 170                 175

Ile Val Val Tyr Lys Gly Asp Val Tyr Asn Met Asp Tyr Pro Pro Phe
            180                 185                 190

Gly Ala Gly Arg Pro Gly Gln Phe Gly Asp Ile Gln Ser Arg Thr Pro
        195                 200                 205

Glu Ser Lys Asp Val Tyr Ala Asn Thr Gln Leu Val Leu Gln Arg Pro
    210                 215                 220

Ala Ala Gly Thr Val His Val Pro Tyr Ser Gln Ala Pro Ser Gly Phe
225                 230                 235                 240

Lys Tyr Trp Leu Lys Glu Arg Gly Ala Ser Leu Gln His Thr Ala Pro
```

```
                245                 250                 255

Phe Gly Cys Gln Ile Ala Thr Asn Pro Val Arg Ala Met Asn Cys Ala
            260                 265                 270

Val Gly Asn Met Pro Ile Ser Ile Asp Ile Pro Asp Ala Ala Phe Thr
        275                 280                 285

Arg Val Val Asp Ala Pro Ser Leu Thr Asp Met Ser Cys Glu Val Pro
    290                 295                 300

Ala Cys Thr His Ser Ser Asp Phe Gly Gly Val Ala Ile Ile Lys Tyr
305                 310                 315                 320

Ala Val Ser Lys Lys Gly Lys Cys Ala Val His Ser Met Thr Asn Ala
                325                 330                 335

Val Thr Ile Arg Glu Ala Glu Ile Glu Val Glu Gly Asn Ser Gln Leu
            340                 345                 350

Gln Ile Ser Phe Ser Thr Ala Leu Ala Ser Ala Glu Phe Arg Val Gln
        355                 360                 365

Val Cys Ser Thr Gln Val His Cys Ala Ala Glu Cys His Pro Pro Lys
    370                 375                 380

Asp His Ile Val Asn Tyr Pro Ala Ser His Thr Thr Leu Gly Val Gln
385                 390                 395                 400

Asp Ile Ser Ala Thr Ala Met Ser Trp Val Gln Lys Ile Thr Gly Gly
                405                 410                 415

Val Gly Leu Val Val Ala Val Ala Ala Leu Ile Leu Ile Val Val Leu
            420                 425                 430

Cys Val Ser Phe Ser Arg His
        435
```

<210> SEQ ID NO 30
<211> LENGTH: 1317
<212> TYPE: DNA
<213> ORGANISM: Chikungunya virus

<400> SEQUENCE: 30

```
tatgaacatg tgaccgtaat tcctaacact gtcggggtgc cctacaagac cttggttaac     60

cgcccggggt atagccccat ggttctcgag atggaacttc tgtcggtaac gttggagccg    120

acccttttccc ttgactatat tacatgtgag tacaagacgg tgattccatc tccctacgtg    180

aagtgctgcg gtactgctga atgcaaggac aaaaatctcc ctgattactc gtgcaaggta    240

ttcactggag tgtacccatt tatgtgggga ggcgcttatt gtttctgtga tgctgaaaac    300

acccaattat ctgaagccca tgtggagaaa agcgagtcct gtaaaactga gttcgccagc    360

gcctatcgtg cgcacaccgc ttctgcctcc gccaagctta gggtgctata ccagggcaat    420

aatataaccg ttactgcata tgcgaacgga gaccatgcag ttactgtaaa agatgcaaaa    480

tttatagtgg gccccatgag ttcggcttgg acacccttcg acaataagat agtcgtgtac    540

aagggcgacg tgtacaatat ggactaccca cctttcggcg ctggccgtcc tggtcagttc    600

ggagacatcc aaagccggac acctgagtcc aaggacgtct acgcaaacac acagcttgtc    660

ctgcagcggc cagcagccgg gacagttcac gtgccttaca gccaggcgcc cagtggcttt    720

aagtattggc taaaggaaag gggggcgagt ctccagcata ctgcccccctt cggctgccag    780

attgcaacta accccgtgcg agctatgaat tgcgcagtcg gcaacatgcc tatctctatt    840

gatatcccgg acgccgcttt tactcgtgtc gtggacgctc ccagcctgac ggacatgtcc    900

tgcgaagttc ctgcatgcac ccactcatcc gattttggag gtgtggcaat aatcaaatat    960

gcagtcagta aaaagggtaa gtgtgccgtc cactcgatga cgaatgccgt gactatcaga   1020
```

```
gaggcagaga tcgaagtgga aggaaatagc cagttgcaaa tctctttcag cacagccctt   1080

gcaagtgccg agtttcgcgt ccaagtgtgt agcacgcagg ttcactgtgc agccgaatgt   1140

catccgccta aagaccacat agtcaattac cccgcttccc acaccacatt gggagttcag   1200

gacataagtg ctactgctat gagctgggtc caaaagatca ccggaggtgt agggctcgtc   1260

gtggccgtcg ccgctctaat tctgatcgtg gttctgtgcg tcagtttttc ccgtcac      1317


<210> SEQ ID NO 31
<211> LENGTH: 423
<212> TYPE: PRT
<213> ORGANISM: Chikungunya virus

<400> SEQUENCE: 31

Ser Thr Lys Asp Asn Phe Asn Val Tyr Lys Ala Thr Arg Pro Tyr Leu
1               5                   10                  15

Ala His Cys Pro Asp Cys Gly Glu Gly His Ser Cys His Ser Pro Val
            20                  25                  30

Ala Leu Glu Arg Ile Arg Asn Glu Ala Thr Asp Gly Thr Leu Lys Ile
        35                  40                  45

Gln Val Ser Leu Gln Ile Gly Ile Gly Thr Asp Asp Ser His Asp Trp
    50                  55                  60

Thr Lys Leu Arg Tyr Met Asp Asn His Ile Pro Ala Asp Ala Gly Arg
65                  70                  75                  80

Ala Gly Leu Phe Val Arg Thr Ser Ala Pro Cys Thr Ile Thr Gly Thr
                85                  90                  95

Met Gly His Phe Ile Leu Ala Arg Cys Pro Lys Gly Glu Thr Leu Thr
            100                 105                 110

Val Gly Phe Thr Asp Ser Arg Lys Ile Ser His Ser Cys Thr His Pro
        115                 120                 125

Phe His His Asp Pro Pro Val Ile Gly Arg Glu Lys Phe His Ser Arg
    130                 135                 140

Pro Gln His Gly Lys Glu Leu Pro Cys Ser Thr Tyr Val Gln Ser Asn
145                 150                 155                 160

Ala Ala Thr Ala Glu Glu Ile Glu Val His Met Pro Pro Asp Thr Pro
                165                 170                 175

Asp Arg Thr Leu Leu Ser Gln Gln Ser Gly Asn Val Lys Ile Thr Val
            180                 185                 190

Asn Ser Gln Thr Val Arg Tyr Lys Cys Asn Cys Gly Gly Ser Asn Glu
        195                 200                 205

Gly Leu Ile Thr Thr Asp Lys Val Ile Asn Asn Cys Lys Val Asp Gln
    210                 215                 220

Cys His Ala Ala Val Thr Asn His Lys Lys Trp Gln Tyr Asn Ser Pro
225                 230                 235                 240

Leu Val Pro Arg Asn Ala Glu Leu Gly Asp Arg Lys Gly Lys Ile His
                245                 250                 255

Ile Pro Phe Pro Leu Ala Asn Val Thr Cys Met Val Pro Lys Ala Arg
            260                 265                 270

Asn Pro Thr Val Thr Tyr Gly Lys Asn Gln Val Ile Met Leu Leu Tyr
        275                 280                 285

Pro Asp His Pro Thr Leu Leu Ser Tyr Arg Ser Met Gly Glu Glu Pro
    290                 295                 300

Asn Tyr Gln Glu Glu Trp Val Thr His Lys Lys Glu Val Val Leu Thr
305                 310                 315                 320
```

```
Val Pro Thr Glu Gly Leu Glu Val Thr Trp Gly Asn Asn Glu Pro Tyr
                325                 330                 335

Lys Tyr Trp Pro Gln Leu Ser Ala Asn Gly Thr Ala His Gly His Pro
            340                 345                 350

His Glu Ile Ile Leu Tyr Tyr Tyr Glu Leu Tyr Pro Thr Met Thr Val
        355                 360                 365

Val Val Val Ser Val Ala Ser Phe Ile Leu Leu Ser Met Val Gly Met
    370                 375                 380

Ala Val Gly Met Cys Met Cys Ala Arg Arg Arg Cys Ile Thr Pro Tyr
385                 390                 395                 400

Glu Leu Thr Pro Gly Ala Thr Val Pro Phe Leu Leu Ser Leu Ile Cys
                405                 410                 415

Cys Ile Arg Thr Ala Lys Ala
            420
```

<210> SEQ ID NO 32
<211> LENGTH: 1269
<212> TYPE: DNA
<213> ORGANISM: Chikungunya virus

<400> SEQUENCE: 32

```
tccacaaaag ataacttcaa cgtttacaaa gctactcgac cctatttggc ccactgcccg      60

gattgtgggg aaggacactc ctgccactct cccgtggccc tcgaacgaat taggaacgag     120

gctactgacg gaaccctaaa gattcaggta tcactccaga tcggaatagg gacagacgac     180

tctcacgatt ggacaaaact cagatatatg gataaccaca tccccgccga cgctggcaga     240

gccggtcttt tcgttcgcac atccgctccc tgcacaataa cgggtaccat ggggcatttc     300

attctggcgc ggtgcccgaa gggagagacc cttacagtgg gctttaccga ctcccgcaag     360

atttctcata gctgtaccca tcccttccat cacgatcctc ctgtaatcgg ccgggagaaa     420

ttccactccc ggccgcaaca tggcaaagag ctgccctgtt ctacctatgt acaaagcaac     480

gccgcgactg ccgaggaaat agaggtgcac atgccaccag ataccccgga tcgaacactt     540

ctttctcaac aaagtggcaa cgtaaaaatc acagttaaca gccagactgt gcggtataag     600

tgcaactgtg gggggttccaa tgaaggcctc atcacgactg acaaggtgat caataactgc     660

aaggtcgacc agtgtcacgc cgcggtgacg aatcacaaaa agtggcagta taactctccg     720

cttgtgccac gtaacgccga gctgggggat agaaagggga agatccacat ccccttttcca     780

ctggctaatg tcacgtgcat ggtgccgaag gctagaaatc ctacagtaac ttacggaaag     840

aatcaagtga tcatgttatt atatcctgac catccgactc tcctgagtta tagatcaatg     900

ggcgaagaac ctaactacca agaagagtgg gtcacccaca agaaggaggt ggttttaaca     960

gtgccaaccg aaggtcttga agtgacctgg ggcaataacg aaccctacaa gtattggcca    1020

cagctgtccg ctaatggcac ggcccacggt cacccccacg agatcatact gtactactat    1080

gaactatacc ctactatgac cgtggtggtg gtgagcgtgg cctccttcat tctcctcagc    1140

atggtgggga tggctgtcgg aatgtgcatg tgcgcgcgcc ggcgatgtat tacgccttac    1200

gagctgactc ccggcgccac cgttccgttt ctgctaagct tgatctgttg tatcaggacg    1260

gccaaggca                                                            1269
```

<210> SEQ ID NO 33
<211> LENGTH: 65
<212> TYPE: PRT
<213> ORGANISM: Chikungunya virus

<400> SEQUENCE: 33

```
Met Ser Leu Ala Ile Pro Val Met Cys Leu Leu Ala Asn Thr Thr Phe
1               5                   10                  15

Pro Cys Ser Gln Pro Pro Cys Ile Pro Cys Cys Tyr Glu Lys Glu Pro
            20                  25                  30

Glu Glu Thr Leu Arg Met Leu Glu Asp Asn Val Met Arg Pro Gly Tyr
        35                  40                  45

Tyr Gln Leu Leu Gln Ala Ser Leu Thr Cys Ser Pro His Arg Gln Arg
    50                  55                  60

Arg
65
```

<210> SEQ ID NO 34
<211> LENGTH: 195
<212> TYPE: DNA
<213> ORGANISM: Chikungunya virus

<400> SEQUENCE: 34

```
atgtcactag ccatccctgt gatgtgtctg ctcgccaaca caactttccc atgctctcag     60

ccaccctgta taccctgctg ctatgagaaa gaacctgagg agaccctgcg catgctggag    120

gacaatgtta tgaggccagg ctactaccaa ctattgcagg caagtttgac ctgctcacca    180

cataggcagc gccga                                                     195
```

<210> SEQ ID NO 35
<211> LENGTH: 61
<212> TYPE: PRT
<213> ORGANISM: Chikungunya virus

<400> SEQUENCE: 35

```
Ala Thr Tyr Gln Glu Ala Ala Val Tyr Leu Trp Asn Glu Gln Gln Pro
1               5                   10                  15

Leu Phe Trp Leu Gln Ala Leu Ile Pro Leu Ala Ala Leu Ile Val Leu
            20                  25                  30

Cys Asn Cys Leu Arg Leu Leu Pro Cys Cys Cys Lys Thr Leu Ala Phe
        35                  40                  45

Leu Ala Val Met Ser Ile Gly Ala His Thr Val Ser Ala
    50                  55                  60
```

<210> SEQ ID NO 36
<211> LENGTH: 183
<212> TYPE: DNA
<213> ORGANISM: Chikungunya virus

<400> SEQUENCE: 36

```
gctacctatc aggaggcggc tgtatacctc tggaacgagc agcagccact cttctggctt     60

caggccctga tccccttggc agccctcata gtgctgtgca actgtctgcg tctgctccca    120

tgttgttgca agacactggc cttcctggca gtgatgagca ttggcgcgca cactgtttca    180

gcc                                                                  183
```